(12) United States Patent
Kim et al.

(10) Patent No.: US 11,746,344 B2
(45) Date of Patent: Sep. 5, 2023

(54) METHOD FOR PRODUCING ISOPRENE USING TRANSFORMED E. COLI

(71) Applicant: INDUSTRY-ACADEMIC COOPERATION FOUNDATION GYEONGSANG NATIONAL UNIVERSITY, Gyeongsangnam-do (KR)

(72) Inventors: Seon Won Kim, Gyeongsangnam-do (KR); Jung Hun Kim, Gyeongsangnam-do (KR); Myeong Seok Cha, Gyeongsangnam-do (KR); Hui Jeong Jang, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 1041 days.

(21) Appl. No.: 16/073,073

(22) PCT Filed: Jan. 26, 2017

(86) PCT No.: PCT/KR2017/000990
§ 371 (c)(1),
(2) Date: Jul. 26, 2018

(87) PCT Pub. No.: WO2017/131488
PCT Pub. Date: Aug. 3, 2017

(65) Prior Publication Data
US 2021/0324362 A1 Oct. 21, 2021

(30) Foreign Application Priority Data
Jan. 26, 2016 (KR) .......... 10-2016-0009568
Jan. 26, 2017 (KR) .......... 10-2017-0012696

(51) Int. Cl.
*C12N 9/88* (2006.01)
*C12N 9/10* (2006.01)
*C12N 9/12* (2006.01)
*C12N 9/90* (2006.01)
*C12P 5/00* (2006.01)

(52) U.S. Cl.
CPC .......... *C12N 9/88* (2013.01); *C12N 9/1025* (2013.01); *C12N 9/1029* (2013.01); *C12N 9/1205* (2013.01); *C12N 9/1229* (2013.01); *C12N 9/90* (2013.01); *C12P 5/007* (2013.01); *C12Y 203/01194* (2013.01); *C12Y 203/0301* (2013.01); *C12Y 207/01036* (2013.01); *C12Y 207/04002* (2013.01); *C12Y 401/01033* (2013.01); *C12Y 402/03027* (2013.01)

(58) Field of Classification Search
None
See application file for complete search history.

(56) References Cited

U.S. PATENT DOCUMENTS

| | | | | |
|---|---|---|---|---|
| 5,543,307 A | * | 8/1996 | Ikeda ...... | C12N 15/68 424/200.1 |
| 2012/0276603 A1 | | 11/2012 | Beck et al. | |
| 2013/0122562 A1 | * | 5/2013 | Aldor ...... | C12P 5/007 435/254.22 |

FOREIGN PATENT DOCUMENTS

| | | |
|---|---|---|
| JP | 3563432 B2 | 9/2004 |
| JP | 2007-49987 A | 3/2007 |
| JP | WO 2013/020118 | 2/2013 |
| KR | 10-2015-0100666 A | 9/2015 |
| WO | WO 2012/149469 A1 | 11/2012 |

OTHER PUBLICATIONS

Chica et al. Curr Opin Biotechnol. Aug. 2005;16(4):378-84 (Year: 2005).*
Singh et al. Curr Protein Pept Sci. 2017, 18, 1-11 (Year: 2017).*
Phue et al. Biotechnol Bioeng. Nov. 1, 2008;101(4):831-6. (Year: 2008).*
Accession V00328. Apr. 18, 2005 (Year: 2005).*
Kalderon et al. PLoS One. Dec. 3, 2014;9(12):e114380, pp. 1-14 (Year: 2014).*
International Search Report for PCT/KR2017/000990 dated Apr. 27, 2017.
George, K. W. et al., "Metabolic engineering for the high-yield production of isoprenoid-based C5 alcohols in *E. coli*", Scientific Reports, , vol. 5, document No. 11128, pp. 1-12, 2015.

* cited by examiner

*Primary Examiner* — Christian L Fronda
(74) *Attorney, Agent, or Firm* — The PL Law Group, PLLC

(57) ABSTRACT

A method for producing isoprene includes culturing *E. coli*, which has isoprene productivity and in which a gene encoding a recA protein is attenuated or deleted, in a medium containing a carbon source. Therefore, a great amount of isoprene may be produced within a short period of time, and thereby considerably decreasing isoprene production unit costs.

31 Claims, 16 Drawing Sheets
Specification includes a Sequence Listing.

———— GENE REMOVED FOR PREPARING AceCo STRAIN

SEQUENCE LISTING

<160> NUMBER OF SEQ ID NOS: 93

<210> SEQ ID NO 1
<211> LENGTH: 1683
<212> TYPE: DNA
<213> ORGANISM: Populus trichocarpa

<400> SEQUENCE: 1

```
atggcttgct ctgtatccac tgagaacgta tctttcactg agactgaaac tgagacccgt      60
cgctctgcga actatgagcc aaactcttgg gattacgatt atctgctgtc ctctgacact     120
gacgaaagca ttgaagttta caaggacaaa gcgaaaaagc tggaagcgga ggttcgtcgc     180
gaaatcaaca acgagaaagc tgaattcctg actctgctgg agctgatcga caacgtacag     240
cgtctgggtc tgggttaccg tttcgagtct gacatccgcc gtgctctgga tcgcttcgtt     300
tccagcggcg gtttcgatgc agtgaccaag actagcctgc atgcgaccgc gctgtctttc     360
cgtctgctgc gtcagcacgg ttttgaagtt tctcaggaag cgttctctgg cttcaaggac     420
cagaacggta atttcctgga aaacctgaag gaggacatta aggcgattct gtccctgtac     480
gaagcgtctt ttctggcgct ggaaggcgag aacatcctgg acgaagcgaa agtattcgca     540
atctcccacc tgaaagaact gagcgaagaa aaaatcggta agatctggc ggaacaggtg     600
aaccacgctc tggaactgcc tctgcatcgt cgtacccagc gtctggaggc tgtgctgtcc     660
attgaagcat accgtaagaa agaagatgca gatcaggttc tgctggaact ggcgatcctg     720
gactacaaca tgattcagtc tgtgtaccag cgtgacctgc gtgaaacctc tcgctggtgg     780
cgccgtgtgg gtctggcaac caaactgcac ttcgcacgcg atcgtctgat tgaatccttc     840
tactgggctg taggcgtggc cttcgaaccg cagtactccg attgccgtaa ctctgttgct     900
aaaatgttct ctttcgttac cattatcgat gacatctatg acgtttatgg taccctggat     960
gaactggagc tgttcaccaa cgcagttgaa cgctgggacg ttaacgcgat tgatgacctg    1020
cctgactaca tgaaactgtg cttcctggcg ctgtataaca ctatcaacga gatcgcgtat    1080
gataacctga agaaaaagg tgaaaacatt ctgccgtatc tgaccaaagc ctgggccgac    1140
ctgtgtaacg cattcctgca ggaggccaaa tggctgtaca ataagtctac tcctactttc    1200
gacgattact cggtaacgc ttggaaatct agctctggcc cgctgcaact ggtcttcgcc    1260
tatttcgcgg tagtgcaaaa catcaaaaag gaagagatcg agaatctgca gaaatatcac    1320
gacattatct cccgcccgag ccacatcttc cgcctgtgta acgacctggc ctccgcatcc    1380
gcagaaattg cacgcggcga aaccgccaac tccgtatcct gctatatgcg taccaaaggc    1440
atcagcgaag aactggctac cgaatccgtg atgaacctga tcgatgaaac ttggaagaag    1500
atgaacaaag aaaaactggg cggttctctg ttcgccaaac cattcgttga aaccgcgatt    1560
aacctggcgc gccaatctca ctgcacctat cataacggtg acgcacacac ctccccggat    1620
gaactgaccc gtaagcgtgt gctgtccgtt attaccgaac caattctgcc gttcgaacgc    1680
taa                                                                 1683
```

<210> SEQ ID NO 2
<211> LENGTH: 1197
<212> TYPE: DNA
<213> ORGANISM: Enterococcus faecalis

<400> SEQUENCE: 2

```
atggagttga aaacagtagt tattattgat gcattacgaa caccaattgg aaaatataaa      60
ggcagcttaa gtcaagtaag tgccgtagac ttaggaacac atgttacaac acaacttta     120
aaaagacatt ccactatttc tgaagaaatt gatcaagtaa tctttggaaa tgttttacaa     180
gctggaaatg ccaaaatcc cgcacgacaa atagcaataa acagcggttt gtctcatgaa     240
attcccgcaa tgacggttaa tgaggtctgc ggatcaggaa tgaaggccgt tattttggcg     300
aaacaattga ttcaattagg agaagcggaa gttttaattg ctggtgggat tgagaatatg     360
tcccaagcac ctaaattaca acgatttaat tacgaaacag aaagctacga tgcgcctttt     420
tctagtatga tgtacgatgg gttaacggat gcctttagtg gtcaggcaat gggcttaact     480
gctgaaaatg tggccgaaaa gtatcatgta actagagaag agcaagatca attttctgta     540
cattcacaat aaaagcagc tcaagcacaa gcagaaggga tattcgctga cgaaatagcc     600
ccattagaag tgtcaggaac gcttgtggag aaagatgaag ggattcgccc taattcgagc     660
gttgagaagc taggaacgct taaaacagtt tttaagaag acggtactgt aacagcaggg     720
aatgcatcaa ccattaatga tggggcttct gctttgatta ttgcttcaca gaatatgcc     780
gaagcacacg gtcttcctta tttagctatt attcgagaca gtgtggaagt cggtattgat     840
ccagcctata tgggaatttc gccgattaaa gccattcaaa aactgttagc gcggaatcaa     900
cttactacgg aagaaattga tctgtatgaa atcaacgaag catttgcagc aacttcaatc     960
gtggtccaaa gagaactggc tttaccagag gaaaaggtca acatttatgg tggcggtatt    1020
tcattaggtc atgcgattgg tgccacaggt gctcgtttat taacgagttt aagttatcaa    1080
ttaaatcaaa agaaaagaa atatggcgtg gcttctttat gtatcggcgg tggcttagga    1140
ctcgctatgc tactagagag acctcagcaa aaaaaaacag ccgattttat caaataa      1197
```

<210> SEQ ID NO 3
<211> LENGTH: 1152
<212> TYPE: DNA
<213> ORGANISM: Enterococcus faecalis

<400> SEQUENCE: 3

```
atgacaattg ggattgataa aattagtttt tttgtgcccc cttattatat tgatatgacg      60
gcactggctg aagccagaaa tgtagaccct ggaaaatttc atattggtat tgggcaagac     120
caaatggcgg tgaacccaat cagccaagat attgtgacat ttgcagccaa tgccgcagaa     180
gcgatcttga ccaaagaaga taagagggcc attgatatgg tgattgtcgg gactgagtcc     240
agtatcgatg agtcaaaagc ggccgcagtt gtcttacatc gtttaatggg gattcaacct     300
ttcgctcgct ctttcgaaat caaggaagct tgttacggag caacagcagg cttacagtta     360
gctaagaatc acgtagcctt acatccagat aaaaaagtct tggtcgtagc agcagatatt     420
gcaaaatatg gcttaaattc tggcggtgag cctacacaag gagctgggggc ggttgcaatg     480
ttagttgcta gtgaaccgcg cattttggct ttaaaagagg ataatgtgat gctgacgcaa     540
gatatctatg acttttggcg tccaacaggc catccatatc ctatggtcga tggtcctttg     600
tcaaacgaaa cctacatcca atcttttgcc caagtctggg atgaacataa aaaacgaacc     660
ggtcttgatt ttgcagatta tgatgcttta gcgttccata ttccttacac aaaaatgggc     720
aaaaaagcct tattagcaaa aatctccgac caaactgaag cagaacagga acgaatttta     780
gcccgttatg aagaaagcat catctatagt cgtcgcgtag gaaacttgta tacgggttca     840
```

```
ctttatctgg gactcatttc cctttagaa aatgcaacga ctttaaccgc aggcaatcaa      900
attgggttat tcagttatgg ttctggtgct gtcgctgaat ttttcactgg tgaattagta      960
gctggttatc aaaatcattt acaaaagaa actcatttag cactgctgga taatcggaca     1020
gaactttcta tcgctgaata tgaagccatg tttgcagaaa ctttagacac agacattgat     1080
caaacgttag aagatgaatt aaaatatagt atttctgcta ttaataatac cgttcgttct     1140
tatcgaaact aa                                                         1152
```

<210> SEQ ID NO 4
<211> LENGTH: 879
<212> TYPE: DNA
<213> ORGANISM: Streptococcus pneumoniae

<400> SEQUENCE: 4

```
atgacaaaaa aagttggtgt cggtcaggca catagtaaga taattttaat aggggaacat       60
gcggtcgttt acggttatcc tgccatttcc ctgcctcttt tggaggtgga ggtgacctgt      120
aaggtagttc ctgcagagag tccttggcgc ctttatgagg aggataccct gtccatggcg      180
gtttatgcct cactggagta tttggatatc acagaagcct gcattcgttg tgagattgac      240
tcggctatcc ctgagaaacg ggggatgggt tcgtcagcgg ctatcagcat gcggccatt       300 cgtgcggtat ttgactacta tcaggctgat ctgcctcatg atgtactaga aatcttggtc      360
aatcgagctg aaatgattgc ccatatgaat cctagtggtt tggatgctaa gacctgtctc      420
agtgaccaac ctattcgctt tatcaagaac gtaggattta cagaacttga gatggattta      480
tccgcctatt tggtgattgc cgatacgggt gtttatggtc atactcgtga agccatccaa      540
gtggttcaaa ataagggcaa ggatgcccta ccgttttgc atgccttggg agaattaacc      600
cagcaagcag aagttgcgat tcacaaaaaa gatgctgaag gactgggaca aatcctcagt      660
caagcgcatt tacatttaaa agaaattgga gtcagtagcc ctgaggcaga ctttttggtt      720
gaaacgactc ttagccatgg tgctctgggt gccaagatga gcggtggtgg gctaggaggt      780
tgtatcatag ccttggtaac caatttgaca cacgcacaag aactagcaga aagattagaa      840
gagaaaggag ctgttcagac atggatagag agcctgtaa                             879
```

<210> SEQ ID NO 5
<211> LENGTH: 954
<212> TYPE: DNA
<213> ORGANISM: Streptococcus pneumoniae

<400> SEQUENCE: 5

```
atggatagag agcctgtaac agtacgttcc tacgcaaata ttgctattat caaatattgg       60
ggaaagaaaa aagaaaaaga gatggtgcct gctactagca gtatttctct aactttggaa      120
aatatgtata cagagacgac cttgtcgcct ttaccagcca atgtaacagc tgacgaattt      180
tacatcaatg gtcagctaca aaatgaggtc gagcatgcca agatgagtaa gattattgac      240
cgttatcgtc cagctggtga gggctttgtc cgtatcgata ctcaaaacaa tatgcctact      300
gcagcgggcc tgtcctcaag ttctagtggt ttgtccgccc tggtcaaggc ttgtaatgct      360
tatttcaagc ttggattgga tagaagtcag ttggcacagg aagccaaatt tgcctcaggc      420
tcttcttctc ggagttttta tggaccacta ggagcctggg ataaggatag tggagaaatt      480
taccctgtag agacagactt gaaactagct atgattatgt tggtgctaga ggacaagaaa      540
aaaccaatct ctagccgtga cgggatgaaa ctttgtgtgg aaacctcgac gacttttgac      600
gactgggttc gtcagtctga gaaggactat caggatatgc tgatttatct caaggaaaat      660
```

| | | |
|---|---|---|
| gattttgcca agattggaga attaacggag aaaaatgccc tggctatgca tgctacgaca | | 720 |
| aagactgcta gtccagcctt ttcttatctg acgatgcctc cttatgaggc tatggacttt | | 780 |
| gttcgccagc ttcgtgagaa aggagaggcc tgctacttta ccatggatgc tggtcccaat | | 840 |
| gttaaggtct tctgtcagga gaaagacttg gagcatttat cagaaatttt cggtcatcgt | | 900 |
| tatcgcttga ttgtgtcaaa acaaaggat ttgagtcaag atgattgctg ttaa | | 954 |

<210> SEQ ID NO 6
<211> LENGTH: 1008
<212> TYPE: DNA
<213> ORGANISM: Streptococcus pneumoniae

<400> SEQUENCE: 6

| | | |
|---|---|---|
| atgattgctg ttaaaacttg cggaaaactc tattgggcag gtgaatatgc tattttagag | | 60 |
| ccagggcagt tagctttgat aaaggatatt cccatctata tgagggctga gattgctttt | | 120 |
| tctgacagct accgtatcta ttcagatatg tttgatttcg cagtggactt aaggcctaat | | 180 |
| cctgactaca gcttgattca agaaacgatt gctttgatgg gagacttcct cgctgttcgt | | 240 |
| ggtcagaatt taagaccttt ttctctagaa atctgtggca aaatgaacg agaagggaaa | | 300 |
| aagtttggtc taggttctag tggcagcgtc gttgtcttgg ttgtcaaggc tttactggct | | 360 |
| ctgtatgatg tttctgttga tcaggagctc ttgttcaagc tgactagcgc tgtcttgctc | | 420 |
| aagcgaggag acaatggttc catgggcgac cttgcctgta ttgtggcaga ggatttggtt | | 480 |
| ctctaccagt catttgatcg ccagaaggtg gctgctggt tagaagaaga aaacttggcg | | 540 |
| acagttctgg agcgtgattg gggctttca atttcacaag tgaaaccaac tttagaatgt | | 600 |
| gatttcttag tgggatggac caaggaagtg gctgtatcga gtcacatggt ccagcaaatc | | 660 |
| aagcaaaata tcaatcaaaa ttttttaagt tcctcaaaag aaacggtggt ttctttggtc | | 720 |
| gaagccttgg aacaggggaa atcagaaaag attatcgagc aagtagaagt agccagcaag | | 780 |
| cttttagaag gcttgagtac agatatttac acgcctttgc ttagacagtt gaaagaagcc | | 840 |
| agtcaagatt tgcaggccgt tgccaagagt agtggtgctg gtggtggtga ctgtggcatc | | 900 |
| gccctgagtt ttgatgcgca atcaaccaaa accttaaaaa atcgttgggc cgatctgggg | | 960 |
| attgagctct tatatcaaga aaggatagga catgacgaca aatcgtaa | | 1008 |

<210> SEQ ID NO 7
<211> LENGTH: 549
<212> TYPE: DNA
<213> ORGANISM: Escherichia coli MG1655

<400> SEQUENCE: 7

| | | |
|---|---|---|
| atgcaaacgg aacacgtcat tttattgaat gcacagggag ttcccacggg tacgctggaa | | 60 |
| aagtatgccg cacacacggc agacacccgc ttacatctcg cgttctccag ttggctgttt | | 120 |
| aatgccaaag acaattatt agttacccgc cgcgcactga gcaaaaaagc atggcctggc | | 180 |
| gtgtggacta actcggtttg tgggcaccca caactgggag aaagcaacga agacgcagtg | | 240 |
| atccgccgtt gccgttatga gcttggcgtg gaaattacgc ctcctgaatc tatctatcct | | 300 |
| gactttcgct accgcgccac cgatccgagt ggcattgtgg aaaatgaagt gtgtccggta | | 360 |
| tttgccgcac gcaccactag tgcgttacag atcaatgatg atgaagtgat ggattatcaa | | 420 |
| tggtgtgatt tagcagatgt attacacggt attgatgcca cgccgtgggc gttcagtccg | | 480 |
| tggatggtga tgcaggcgac aaatcgcgaa gccagaaaac gattatctgc atttacccag | | 540 | cttaaataa                                                                549

<210> SEQ ID NO 8
<211> LENGTH: 1050
<212> TYPE: DNA
<213> ORGANISM: Synechocystis sp. PCC6803

<400> SEQUENCE: 8
atggatagca cccccaccg taagtccgat catatccgca ttgtcctaga agaagatgtg     60
gtgggcaaag gcatttccac cggctttgaa agattgatgc tggaacactg cgctcttcct    120
gcggtggatc tggatgcagt ggatttggga ctgaccctct ggggtaaatc cttgacttac    180
ccttggttga tcagcagtat gaccggcggc acgccagagg ccaagcaaat taatctattt    240
ttagccgagg tggcccaggc tttgggcatc gccatgggtt tgggttccca acgggccgcc    300
attgaaaatc ctgatttagc cttcacctat caagtccgct ccgtcgcccc agatatttta    360
cttttgcca acctgggatt agtgcaatta aattacggtt acggtttgga gcaagcccag    420
cgggcggtgg atatgattga agccgatgcg ctgattttgc atctcaatcc cctccaggaa    480
gcggtgcaac ccgatggcga tcgcctgtgg tcgggactct ggtctaagtt agaagcttta    540
gtagaggctt tggaagtgcc ggtaattgtc aaagaagtgg gcaatggcat tagcggtccg    600
gtggccaaaa gattgcagga atgtggggtc ggggcgatcg atgtggctgg agctgggggc    660
accagttgga gtgaagtgga agcccatcga caaaccgatc gccaagcgaa ggaagtggcc    720
cataactttg ccgattgggg attacccaca gcctggagtt tgcaacaggt agtgcaaaat    780
actgagcaga tcctggtttt cgccagcggc ggcattcgtt ccggcattga cggggccaag    840
gcgatcgccc tggggccac cctggtgggt agtgcggcac cggtattagc agaagcgaaa    900
atcaacgccc aaagggttta tgaccattac caggcacggc taagggaact gcaaatcgcc    960
gccttttgtt gtgatgccgc caatctgacc caactggccc aagtccccct tgggacaga   1020
caatcgggac aaaggttaac taaaccttaa                                   1050

<210> SEQ ID NO 9
<211> LENGTH: 1011
<212> TYPE: DNA
<213> ORGANISM: Streptococcus pneumoniae

<400> SEQUENCE: 9
atgacgacaa atcgtaagga cgagcatatc ctctatgccc ttgagcagaa aagttcctat     60
aatagctttg atgaggtgga gctgattcat tcttccttgc ctctttacaa tctggatgaa    120
atcgatcttt cgacagagtt tgctggtcga aagtgggact tcctttttta tatcaatgcc    180
atgactggtg gaagtaataa gggaagagaa atcaatcaaa agctggctca ggtggcggaa    240
tcctgtggta tttatattgt aacgggttct tatagcgcag ccctcaaaaa tccaacggat    300
gattcttttt ctgtcaagtc tagtcatccc aatctcctcc ttggaaccaa tattggattg    360
gacaagcctg tcgagttagg acttcagact gtagaagaga tgaatcctgt tctattgcaa    420
gtgcatgtca atgtcatgca ggaattactc atgcccgagg gagaaaggaa gtttagaagc    480
tggcaatcgc atctagcaga ttatagcaag caaattcccg ttcctattgt cctcaaggaa    540
gtgggctttg aatggatgc caagacaatc gaaagagcct atgaattcgg tgttcgtaca    600
gtggacctat cggtcgtgg tggcaccagc tttgcctata tcgaaaaccg tcgtagtggc    660
cagcgtgatt acctcaatca atgggtcag tctaccatgc aggccttct caatgcccaa    720
gaatggaaag ataaggtcga actcttggtt agtggagggg ttcggaatcc gctggatatg    780

| attaagtgct tggttttttgg tgctaaggct gtgggattgt cacgaaccgt tctggaattg | 840 |
| gttgaaacct acacagttga agaagtgatt ggcattgtcc aaggctggaa agcagatcta | 900 |
| cgcttgatta tgtgttccct taactgtgcc accatagcag atctacaaaa agtagactat | 960 |
| cttctttatg gaaaattaaa agaagcaaag gatcagatga aaaaggcgta a | 1011 |

```
<210> SEQ ID NO 10
<211> LENGTH: 918
<212> TYPE: DNA
<213> ORGANISM: Haematococcus plavialis

<400> SEQUENCE: 10
```

| atgcttcgtt cgttgctcag aggcctcacg catatccccc gcgtgaactc cgcccagcag | 60 |
| cccagctgtg cacacgcgcg actccagttt aagctcagga gcatgcagat gacgctcatg | 120 |
| cagcccagca tctcagccaa tctgtcgcgc gccgaggacc gcacagacca catgaggggt | 180 |
| gcaagcacct gggcaggcgg gcagtcgcag gatgagctga tgctgaagga cgagtgcatc | 240 |
| ttggtggatg ttgaggacaa catcacaggc catgccagca agctggagtg tcacaagttc | 300 |
| ctaccacatc agcctgcagg cctgctgcac cgggccttct ctgtgttcct gtttgacgat | 360 |
| caggggcgac tgctgctgca acagcgtgca cgctcaaaaa tcaccttccc aagtgtgtgg | 420 |
| acgaacacct gctgcagcca ccctttacat gggcagaccc cagatgaggt ggaccaacta | 480 |
| agccaggtgg ccgacggaac agtacctggc gcaaaggctg ctgccatccg caagttggag | 540 |
| cacgagctgg ggataccagc gcaccagctg ccggcaagcg cgtttcgctt cctcacgcgt | 600 |
| ttgcactact gtgccgcgga cgtgcagcca gctgcgacac aatcagcgct ctggggcgag | 660 |
| cacgaaatgg actacatctt gttcatccgg gccaacgtca ccttggcgcc caaccctgac | 720 |
| gaggtggacg aagtcaggta cgtgacgcaa gaggagctgc ggcagatgat gcagccggac | 780 |
| aacgggctgc aatggtcgcc gtggtttcgc atcatcgccg cgcgcttcct tgagcgttgg | 840 |
| tgggctgacc tggacgcggc cctaaacact gacaaacacg aggattgggg aacggtgcat | 900 |
| cacatcaacg aagcgtaa | 918 |

```
<210> SEQ ID NO 11
<211> LENGTH: 2259
<212> TYPE: DNA
<213> ORGANISM: Artificial Sequence
<220> FEATURE:
<223> OTHER INFORMATION: gene coding fusion protein of isoprene synthase
      and isoprenyl pyrophosphate isomerase

<400> SEQUENCE: 11
```

| atggcttgct ctgtatccac tgagaacgta tctttcactg agactgaaac tgagacccgt | 60 |
| cgctctgcga actatgagcc aaactcttgg gattacgatt atctgctgtc ctctgacact | 120 |
| gacgaaagca ttgaagttta caaggacaaa gcgaaaaagc tggaagcgga ggttcgtcgc | 180 |
| gaaatcaaca acgagaaagc tgaattcctg actctgctgg agctgatcga caacgtacag | 240 |
| cgtctgggtc tgggttaccg tttcgagtct gacatccgcc gtgctctgga tcgcttcgtt | 300 |
| tccagcggcg gtttcgatgc agtgaccaag actagcctgc atgcgaccgc gctgtctttc | 360 |
| cgtctgctgc gtcagcacgg ttttgaagtt tctcaggaag cgttctctgg cttcaaggac | 420 |
| cagaacggta atttcctgga aaacctgaag gaggacatta aggcgattct gtccctgtac | 480 |
| gaagcgtctt tctggcgcgt ggaaggcgag aacatcctgg acgaagcgaa agtattcgca | 540 |
| atctcccacc tgaaagaact gagcgaagaa aaaatcggta agatctggc ggaacaggtg | 600 |

```
aaccacgctc tggaactgcc tctgcatcgt cgtacccagc gtctggaggc tgtgctgtcc      660
attgaagcat accgtaagaa agaagatgca gatcaggttc tgctggaact ggcgatcctg      720
gactacaaca tgattcagtc tgtgtaccag cgtgacctgc gtgaaacctc tcgctggtgg      780
cgccgtgtgg gtctggcaac caaactgcac ttcgcacgcg atcgtctgat tgaatccttc      840
tactgggctg taggcgtggc cttcgaaccg cagtactccg attgccgtaa ctctgttgct      900
aaaatgttct ctttcgttac cattatcgat gacatctatg acgtttatgg taccctggat      960
gaactggagc tgttcaccaa cgcagttgaa cgctgggacg ttaacgcgat tgatgacctg     1020
cctgactaca tgaaactgtg cttcctggcg ctgtataaca ctatcaacga gatcgcgtat     1080
gataacctga agaaaaagg tgaaaacatt ctgccgtatc tgaccaaagc ctgggccgac     1140
ctgtgtaacg cattcctgca ggaggccaaa tggctgtaca taagtctac tcctactttc     1200 gacgattact tcggtaacgc ttggaaatct agctctggcc cgctgcaact ggtcttcgcc     1260
tatttcgcgg tagtgcaaaa catcaaaaag gaagagatcg agaatctgca gaaatatcac     1320
gacattatct cccgcccgag ccacatcttc cgcctgtgta cgacctggc ctccgcatcc     1380 gcagaaattg cacgcggcga aaccgccaac tccgtatcct gctatatgcg taccaaaggc     1440
atcagcgaag aactggctac cgaatccgtg atgaacctga tcgatgaaac ttggaagaag     1500
atgaacaaag aaaaactggg cggttctctg ttcgccaaac cattcgttga accgcgatt     1560 aacctggcgc gccaatctca ctgcacctat cataacggtg acgcacacac ctccccggat     1620
gaactgaccc gtaagcgtgt gctgtccgtt attaccgaac caattctgcc gttcgaacgc     1680
ggtggcggtg gctcgggtgg cggcggatcc atgcaaacgg aacacgtcat tttattgaat     1740
gcacagggag ttcccacggg tacgctggaa aagtatgccg cacacacggc agacacccgc     1800
ttacatctcg cgttctccag ttggctgttt aatgccaaag acaattatt agttacccgc     1860 cgcgcactga gcaaaaaagc atggcctggc gtgtggacta ctcggtttg tgggcaccca     1920 caactgggag aaagcaacga agacgcagtg atccgccgtt gccgttatga gcttggcgtg     1980
gaaattacgc ctcctgaatc tatctatcct gactttcgct accgcgccac cgatccgagt     2040
ggcattgtgg aaaatgaagt gtgtccggta tttgccgcac gcaccactag tgcgttacag     2100
atcaatgatg atgaagtgat ggattatcaa tggtgtgatt tagcagatgt attcacggt     2160 attgatgcca cgccgtgggc gttcagtccg tggatggtga tgcaggcgac aaatcgcgaa     2220
gccagaaaac gattatctgc atttacccag cttaaataa                            2259
```

<210> SEQ ID NO 12
<211> LENGTH: 2259
<212> TYPE: DNA
<213> ORGANISM: Artificial Sequence
<220> FEATURE:
<223> OTHER INFORMATION: gene coding fusion protein of isoprene synthase
and isoprenyl pyrophosphate isomerase

<400> SEQUENCE: 12

```
atgcaaacgg aacacgtcat tttattgaat gcacagggag ttcccacggg tacgctggaa       60
aagtatgccg cacacacggc agacacccgc ttacatctcg cgttctccag ttggctgttt      120
aatgccaaag acaattatt agttacccgc cgcgcactga gcaaaaaagc atggcctggc      180
gtgtggacta ctcggtttg tgggcaccca caactgggag aaagcaacga agacgcagtg      240
atccgccgtt gccgttatga gcttggcgtg gaaattacgc ctcctgaatc tatctatcct      300
gactttcgct accgcgccac cgatccgagt ggcattgtgg aaaatgaagt gtgtccggta      360
```

```
tttgccgcac gcaccactag tgcgttacag atcaatgatg atgaagtgat ggattatcaa      420
tggtgtgatt tagcagatgt attacacggt attgatgcca cgccgtgggc gttcagtccg      480
tggatggtga tgcaggcgac aaatcgcgaa gccagaaaac gattatctgc atttacccag      540
cttaaaggtg gcggtggctc gggtggcggc ggatccatgg cttgctctgt atccactgag      600
aacgtatctt tcactgagac tgaaactgag accgtcgct ctgcgaacta tgagccaaac       660
tcttgggatt acgattatct gctgtcctct gacactgacg aaagcattga agtttacaag      720
gacaaagcga aaagctgga agcggaggtt cgtcgcgaaa tcaacaacga gaaagctgaa       780
ttcctgactc tgctggagct gatcgacaac gtacagcgtc tgggtctggg ttaccgtttc      840
gagtctgaca tccgccgtgc tctggatcgc ttcgttcca gcggcggttt cgatgcagtg       900
accaagacta gcctgcatgc gaccgcgctg tcttccgtc tgctgcgtca gcacggtttt       960
gaagtttctc aggaagcgtt ctctggcttc aaggaccaga acggtaattt cctggaaaac     1020
ctgaaggagg acattaaggc gattctgtcc ctgtacgaag cgtctttct ggcgctggaa      1080 ggcgagaaca tcctggacga agcgaaagta ttcgcaatct cccacctgaa agaactgagc     1140
gaagaaaaaa tcggtaaaga tctggcgaa caggtgaacc acgctctgga actgcctctg       1200
catcgtcgta cccagcgtct ggaggctgtg ctgtccattg aagcataccg taagaaagaa     1260
gatgcagatc aggttctgct ggaactggcg atcctggact acaacatgat tcagtctgtg     1320
taccagcgtg acctgcgtga aacctctcgc tggtggcgcc gtgtgggtct ggcaaccaaa     1380
ctgcacttcg cacgcgatcg tctgattgaa tccttctact gggctgtagg cgtggccttc     1440
gaaccgcagt actccgattg ccgtaactct gttgctaaaa tgttctcttt cgttaccatt     1500
atcgatgaca tctatgacgt ttatggtacc ctggatgaac tggagctgtt caccaacgca     1560
gttgaacgct gggacgttaa cgcgattgat gacctgcctg actacatgaa actgtgcttc     1620
ctggcgctgt ataacactat caacgagatc gcgtatgata acctgaaaga aaaaggtgaa     1680
aacattctgc cgtatctgac caaagcctgg gccgacctgt gtaacgcatt cctgcaggag     1740
gccaaatggc tgtacaataa gtctactcct actttcgacg attacttcgg taacgcttgg     1800
aaatctagct ctggcccgct gcaactggtc ttcgcctatt tcgcggtagt gcaaaacatc     1860
aaaaaggaag agatcgagaa tctgcagaaa tatcacgaca ttatctcccg cccgagccac     1920
atcttccgcc tgtgtaacga cctggcctcc gcatccgcag aaattgcacg cggcgaaacc     1980
gccaactccg tatcctgcta tgcgtaccc aaaggcatca gcgaagaact ggctaccgaa     2040
tccgtgatga acctgatcga tgaaacttgg aagaagatga caaagaaaa actgggcggt      2100 tctctgttcg ccaaaccatt cgttgaaacc gcgattaacc tggcgcgcca atctcactgc     2160
acctatcata acggtgacgc acacacctcc ccggatgaac tgacccgtaa gcgtgtgctg     2220
tccgttatta ccgaaccaat tctgccgttc gaacgctaa                             2259
```

<210> SEQ ID NO 13
<211> LENGTH: 2760
<212> TYPE: DNA
<213> ORGANISM: Artificial Sequence
<220> FEATURE:
<223> OTHER INFORMATION: gene coding fusion protein of isoprene synthase
     and isoprenyl pyrophosphate isomerase

<400> SEQUENCE: 13

```
atggcttgct ctgtatccac tgagaacgta tctttcactg agactgaaac tgagacccgt       60
cgctctgcga actatgagcc aaactcttgg gattacgatt atctgctgtc ctctgacact      120
```

```
gacgaaagca ttgaagttta caaggacaaa gcgaaaaagc tggaagcgga ggttcgtcgc    180
gaaatcaaca acgagaaagc tgaattcctg actctgctgg agctgatcga caacgtacag    240
cgtctgggtc tgggttaccg tttcgagtct gacatccgcc gtgctctgga tcgcttcgtt    300
tccagcggcg gtttcgatgc agtgaccaag actagcctgc atgcgaccgc gctgtctttc    360
cgtctgctgc gtcagcacgg ttttgaagtt tctcaggaag cgttctctgg cttcaaggac    420
cagaacggta atttcctgga aaacctgaag gaggacatta aggcgattct gtccctgtac    480
gaagcgtctt ttctggcgct ggaaggcgag aacatcctgg acgaagcgaa agtattcgca    540
atctcccacc tgaaagaact gagcgaagaa aaaatcggta agatctggc ggaacaggtg     600
aaccacgctc tggaactgcc tctgcatcgt cgtacccagc gtctggaggc tgtgctgtcc    660
attgaagcat accgtaagaa agaagatgca gatcaggttc tgctggaact ggcgatcctg    720
gactacaaca tgattcagtc tgtgtaccag cgtgacctgc gtgaaacctc tcgctggtgg    780
cgccgtgtgg gtctggcaac caaactgcac ttcgcacgcg atcgtctgat tgaatccttc    840
tactgggctg taggcgtggc cttcgaaccg cagtactccg attgccgtaa ctctgttgct    900
aaaatgttct ctttcgttac cattatcgat gacatctatg acgtttatgg tacccctggat   960
gaactggagc tgttcaccaa cgcagttgaa cgctgggacg ttaacgcgat tgatgacctg   1020
cctgactaca tgaaactgtg cttcctggcg ctgtataaca ctatcaacga gatcgcgtat   1080
gataacctga agaaaaagg tgaaaacatt ctgccgtatc tgaccaaagc ctgggccgac    1140
ctgtgtaacg cattcctgca ggaggccaaa tggctgtaca ataagtctac tcctactttc   1200
gacgattact tcggtaacgc ttggaaatct agctctggcc cgctgcaact ggtcttcgcc   1260
tatttcgcgg tagtgcaaaa catcaaaaag gaagagatcg agaatctgca gaaatatcac   1320
gacattatct cccgcccgag ccacatcttc cgcctgtgta acgacctggc ctccgcatcc   1380
gcagaaattg cacgcggcga aaccgccaac tccgtatcct gctatatgcg taccaaaggc   1440
atcagcgaag aactggctac cgaatccgtg atgaacctga tcgatgaaac ttggaagaag   1500
atgaacaaag aaaaactggg cggttctctg ttcgccaaac cattcgttga accgcgatt    1560
aacctggcgc gccaatctca ctgcacctat cataacggtg acgcacacac ctccccggat   1620
gaactgaccc gtaagcgtgt gctgtccgtt attaccgaac caattctgcc gttcgaacgc   1680
ggtggcggtg gctcgggtgg cggcggatcc atggatagca cccccaccg taagtccgat   1740
catatccgca ttgtcctaga agaagatgtg gtgggcaaag gcatttccac cggctttgaa   1800
agattgatgc tggaacactg cgctcttcct gcggtggatc tggatgcagt ggatttggga   1860
ctgaccctct ggggtaaatc cttgacttac ccttggttga tcagcagtat gaccggcggc   1920
acgccagagg ccaagcaaat taatctattt ttagccgagg tggcccaggc tttgggcatc   1980
gccatgggtt tgggttccca acgggccgcc attgaaaatc ctgatttagc cttcacctat   2040
caagtccgct ccgtcgcccc agatatttta ctttttgcca acctgggatt agtgcaatta   2100
aattacggtt acggtttgga gcaagcccag cgggcggtgg atatgattga agccgatgcg   2160
ctgattttgc atctcaatcc cctccaggaa gcggtgcaac ccgatggcga tcgcctgtgg   2220
tcgggactct ggtctaagtt agaagcttta gtagaggctt tggaagtgcc ggtaattgtc   2280
aaagaagtgg gcaatggcat tagcggtccg gtggccaaaa gattgcagga atgtgggtc    2340
ggggcgatcg atgtggctgg agctggggc accagttgga gtgaagtgga agcccatcga    2400
caaaccgatc gccaagcgaa ggaagtggcc cataactttg ccgattgggg attacccaca   2460
```

```
gcctggagtt tgcaacaggt agtgcaaaat actgagcaga tcctggtttt cgccagcggc    2520
ggcattcgtt ccggcattga cggggccaag gcgatcgccc tggggccac  cctggtgggt    2580 agtgcggcac cggtattagc agaagcgaaa atcaacgccc aaagggttta tgaccattac    2640
caggcacggc taagggaact gcaaatcgcc gccttttgtt gtgatgccgc caatctgacc    2700
caactggccc aagtcccct  ttgggacaga caatcgggac aaaggttaac taaaccttaa    2760
```

<210> SEQ ID NO 14
<211> LENGTH: 2760
<212> TYPE: DNA
<213> ORGANISM: Artificial Sequence
<220> FEATURE:
<223> OTHER INFORMATION: gene coding fusion protein of isoprene synthase
      and isoprenyl pyrophosphate isomerase

<400> SEQUENCE: 14

```
atggatagca ccccccaccg taagtccgat catatccgca ttgtcctaga agaagatgtg      60
gtgggcaaag gcatttccac cggctttgaa agattgatgc tggaacactg cgctcttcct     120
gcggtggatc tggatgcagt ggatttggga ctgaccctct ggggtaaatc cttgacttac     180
ccttggttga tcagcagtat gaccggcggc acgccagagg ccaagcaaat taatctattt     240
ttagccgagg tggcccaggc tttgggcatc gccatgggtt tgggttccca acgggccgcc     300
attgaaaatc ctgatttagc cttcacctat caagtccgct ccgtcgcccc agatatttta     360 cttttttgcca acctgggatt agtgcaatta aattacggtt acggtttgga gcaagcccag     420
cgggcggtgg atatgattga agccgatgcg ctgattttgc atctcaatcc cctccaggaa     480
gcggtgcaac ccgatggcga tcgcctgtgg tcgggactct ggtctaagtt agaagcttta     540
gtagaggctt tggaagtgcc ggtaattgtc aaagaagtgg gcaatggcat tagcggtccg     600
gtggccaaaa gattgcagga atgtgggtc ggggcgatcg atgtggctgg agctgggggc     660
accagttgga gtgaagtgga agcccatcga caaaccgatc gccaagcgaa ggaagtggcc     720
cataactttg ccgattgggg attacccaca gcctggagtt tgcaacaggt agtgcaaaat     780
actgagcaga tcctggtttt cgccagcggc ggcattcgtt ccggcattga cggggccaag     840
gcgatcgccc tggggccac  cctggtgggt agtgcggcac cggtattagc agaagcgaaa     900
atcaacgccc aaagggttta tgaccattac caggcacggc taagggaact gcaaatcgcc     960
gccttttgtt gtgatgccgc caatctgacc caactggccc aagtcccct  ttgggacaga    1020 caatcgggac aaaggttaac taaacctggt ggcggtggct cgggtggcgg cggatccatg    1080
gcttgctctg tatccactga gaacgtatct ttcactgaga ctgaaactga cccgtcgc      1140 tctgcgaact atgagccaaa ctcttgggat tacgattatc tgctgtcctc tgacactgac    1200
gaaagcattg aagtttacaa ggacaaagcg aaaaagctgg aagcggaggt tcgtcgcgaa    1260
atcaacaacg agaaagctga attcctgact ctgctggagc tgatcgacaa cgtacagcgt    1320
ctgggtctgg gttaccgttt cgagtctgac atcgccgtg  ctctggatcg cttcgtttcc    1380
agcggcggtt tcgatgcagt gaccaagact agcctgcatg cgaccgcgct gtctttccgt    1440
ctgctgcgtc agcacggttt tgaagtttct caggaagcgt tctctggctt caaggaccag    1500
aacggtaatt tcctggaaaa cctgaaggag gacattaagg cgattctgtc cctgtacgaa    1560
gcgtcttttc tggcgctgga aggcgagaac atcctggacg aagcgaaagt attcgcaatc    1620
tcccacctga aagaactgag cgaagaaaaa atcggtaaag atctggcgga acaggtgaac    1680
cacgctctgg aactgcctct gcatcgtcgt acccagcgtc tggaggctgt gctgtccatt    1740
```

```
gaagcatacc gtaagaaaga agatgcagat caggttctgc tggaactggc gatcctggac   1800
tacaacatga ttcagtctgt gtaccagcgt gacctgcgtg aaacctctcg ctggtggcgc   1860
cgtgtgggtc tggcaaccaa actgcacttc gcacgcgatc gtctgattga atccttctac   1920
tgggctgtag gcgtggcctt cgaaccgcag tactccgatt gccgtaactc tgttgctaaa   1980
atgttctctt tcgttaccat tatcgatgac atctatgacg tttatggtac cctggatgaa   2040
ctggagctgt tcaccaacgc agttgaacgc tgggacgtta acgcgattga tgacctgcct   2100
gactacatga aactgtgctt cctggcgctg tataacacta tcaacgagat cgcgtatgat   2160
aacctgaaag aaaaaggtga aacattctg ccgtatctga ccaaagcctg gccgacctg    2220 tgtaacgcat tcctgcagga ggccaaatgg ctgtacaata agtctactcc tactttcgac   2280
gattacttcg gtaacgcttg gaaatctagc tctggcccgc tgcaactggt cttcgcctat   2340
ttcgcggtag tgcaaaacat caaaaaggaa gagatcgaga atctgcagaa atatcacgac   2400
attatctccc gcccgagcca catcttccgc ctgtgtaacg acctggcctc cgcatccgca   2460
gaaattgcac gcggcgaaac cgccaactcc gtatcctgct atatgcgtac caaaggcatc   2520
agcgaagaac tggctaccga atccgtgatg aacctgatcg atgaaacttg gaagaagatg   2580
aacaaagaaa actgggcgg ttctctgttc gccaaaccat tcgttgaaac cgcgattaac    2640
ctggcgcgcc aatctcactg cacctatcat aacggtgacg cacacacctc cccggatgaa   2700
ctgacccgta gcgtgtgct gtccgttatt accgaaccaa ttctgccgtt cgaacgctaa   2760
```

<210> SEQ ID NO 15
<211> LENGTH: 4179
<212> TYPE: DNA
<213> ORGANISM: Artificial Sequence
<220> FEATURE:
<223> OTHER INFORMATION: pTrc99SN vector

<400> SEQUENCE: 15

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg caaatattc     180 tgaaatgagc tgttgacaat taatcatccg gctcgtataa tgtgtggaat tgtgagcgga    240
taacaatttc acacaggagg taataaacca tggaattcga gctcggtacc cggggatcct    300
ctagagtcga cctgcaggca tgcaagcttg gctgttttgg cggatgagag aagattttca    360
gcctgataca gattaaatca gaacgcagaa gcggtctgat aaaacagaat ttgcctggcg    420
gcagtagcgc ggtggtccca cctgacccca tgccgaactc agaagtgaaa cgccgtagcg    480
ccgatggtag tgtggggtct ccccatgcga gagtagggaa ctgccaggca tcaaataaaa    540
cgaaaggctc agtcgaaaga ctgggccttt cgttttatct gttgtttgtc ggtgaacgct    600
ctcctgagta ggacaaatcc gccgggagcg gatttgaacg ttgcgaagca acggcccgga    660
gggtggcggg caggacgccc gccataaact gccaggcatc aaattaagca gaaggccatc    720
ctgacggatg gcctttttgc gtttctacaa actctttttg tttatttttc taaatacatt    780
caaatatgta tccgctcatg agacaataac cctgataaat gcttcaataa tattgaaaaa    840
ggaagagtat gagtattcaa catttccgtg tcgcccttat tcccttttt gcggcatttt    900 gccttcctgt ttttgctcac ccagaaacgc tggtgaaagt aaaagatgct gaagatcagt    960
tgggtgcacg agtgggttac atcgaactgg atctcaacag cggtaagatc cttgagagtt   1020
ttcgccccga agaacgtttt ccaatgatga gcacttttaa agttctgcta tgtggcgcgg   1080
```

```
tattatcccg tgttgacgcc gggcaagagc aactcggtcg ccgcatacac tattctcaga    1140
atgacttggt tgagtactca ccagtcacag aaaagcatct tacggatggc atgacagtaa    1200
gagaattatg cagtgctgcc ataaccatga gtgataacac tgcggccaac ttacttctga    1260
caacgatcgg aggaccgaag gagctaaccg cttttttgca caacatgggg gatcatgtaa    1320
ctcgccttga tcgttgggaa ccggagctga atgaagccat accaaacgac gagcgtgaca    1380
ccacgatgcc tacagcaatg gcaacaacgt tgcgcaaact attaactggc gaactactta    1440
ctctagcttc ccggcaacaa ttaatagact ggatggaggc ggataaagtt gcaggaccac    1500
ttctgcgctc ggcccttccg gctggctggt ttattgctga taaatctgga gccggtgagc    1560
gtgggtctcg cggtatcatt gcagcactgg ggccagatgg taagccctcc cgtatcgtag    1620
ttatctacac gacggggagt caggcaacta tggatgaacg aaatagacag atcgctgaga    1680
taggtgcctc actgattaag cattggtaac tgtcagacca agtttactca tatatacttt    1740
agattgattt aaaacttcat ttttaattta aaaggatcta ggtgaagatc ctttttgata    1800
atctcatgac caaaatccct taacgtgagt tttcgttcca ctgagcgtca gaccccgtag    1860
aaaagatcaa aggatcttct tgagatcctt ttttctgcg cgtaatctgc tgcttgcaaa    1920
caaaaaaacc accgctacca gcggtggttt gtttgccgga tcaagagcta ccaactcttt    1980
ttccgaaggt aactggcttc agcagagcgc agataccaaa tactgtcctt ctagtgtagc    2040
cgtagttagg ccaccacttc aagaactctg tagcaccgcc tacatacctc gctctgctaa    2100
tcctgttacc agtggctgct gccagtggcg ataagtcgtg tcttaccggg ttggactcaa    2160
gacgatagtt accggataag gcgcagcggt cgggctgaac ggggggttcg tgcacacagc    2220
ccagcttgga gcgaacgacc tacaccgaac tgagatacct acagcgtgag ctatgagaaa    2280
gcgccacgct tcccgaaggg agaaaggcgg acaggtatcc ggtaagcggc agggtcggaa    2340
caggagagcg cacgagggag cttccagggg gaaacgcctg gtatctttat agtcctgtcg    2400
ggtttcgcca cctctgactt gagcgtcgat ttttgtgatg ctcgtcaggg gggcggagcc    2460
tatgaaaaaa cgccagcaac gcggcctttt tacggttcct ggccttttgc tggccttttg    2520
ctcacatgtt ctttcctgcg ttatcccctg attctgtgga taaccgtatt accgcctttg    2580
agtgagctga taccgctcgc cgcagccgaa cgaccgagcg cagcgagtca gtgagcgagg    2640
aagcggaaga gcgcctgatg cggtattttc tccttacgca tctgtgcggt atttcacacc    2700
gcatatggtg cactctcagt acaatctgct ctgatgccgc atagttaagc cagtatacac    2760
tccgctatcg ctacgtgact gggtcatggc tgcgccccga cacccgccaa cacccgctga    2820
cgcgccctga cgggcttgtc tgctcccggc atccgcttac agacaagctg tgaccgtctc    2880
cgggagctgc atgtgtcaga ggttttcacc gtcatcaccg aaacgcgcga ggcagcagat    2940
caattcgcgc gcgaaggcga agcggcatgc atttacgttg acaccatcga atggtgcaaa    3000
acctttcgcg gtatggcatg atagcgcccg gaagagagtc aattcagggt ggtgaatgtg    3060
aaaccagtaa cgttatacga tgtcgcagag tatgccggtg tctcttatca gaccgtttcc    3120
cgcgtggtga accaggccag ccacgtttct gcgaaaacgc gggaaaaagt ggaagcggcg    3180
atggcggagc tgaattacat tcccaaccgc gtggcacaac aactggcggg caaacagtcg    3240
ttgctgattg gcgttgccac ctccagtctg gccctgcacg cgccgtcgca aattgtcgcg    3300
gcgattaaat ctcgcgccga tcaactgggt gccagcgtgg tggtgtcgat ggtagaacga    3360
agcggcgtcg aagcctgtaa agcggcggtg cacaatcttc tcgcgcaacg cgtcagtggg    3420
```

```
ctgatcatta actatccgct ggatgaccag gatgccattg ctgtggaagc tgcctgcact    3480
aatgttccgg cgttatttct tgatgtctct gaccagacac ccatcaacag tattattttc    3540
tcccatgaag acggtacgcg actgggcgtg gagcatctgg tcgcattggg tcaccagcaa    3600
atcgcgctgt tagcgggccc attaagttct gtctcggcgc gtctgcgtct ggctggctgg    3660
cataaatatc tcactcgcaa tcaaattcag ccgatagcgg aacgggaagg cgactggagt    3720
gccatgtccg gttttcaaca aaccatgcaa atgctgaatg agggcatcgt tcccactgcg    3780
atgctggttg ccaacgatca gatggcgctg ggcgcaatgc gcgccattac cgagtccggg    3840
ctgcgcgttg gtgcggatat ctcggtagtg ggatacgacg ataccgaaga cagctcatgt    3900
tatatcccgc cgttaaccac catcaaacag gattttcgcc tgctggggca aaccagcgtg    3960
gaccgcttgc tgcaactctc tcagggccag gcggtgaagg caatcagct gttgcccgtc    4020 tcactggtga aagaaaaac caccctggcg cccaatacgc aaaccgcctc tccccgcgcg    4080
ttggccgatt cattaatgca gctggcacga caggtttccc gactggaaag cgggcagtga    4140
gcgcaacgca attaatgtga gttagcgcga attgatctg                          4179
```

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16

```
gccatggctt gctctgtatc cac                                             23
```

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17

```
ctctagatta gcgttcgaac ggcagaattg                                      30
```

<210> SEQ ID NO 18
<211> LENGTH: 861
<212> TYPE: DNA
<213> ORGANISM: Artificial Sequence
<220> FEATURE:
<223> OTHER INFORMATION: ampicillin resistance gene

<400> SEQUENCE: 18

```
atgagtattc aacatttccg tgtcgccctt attcccttt ttgcggcatt ttgccttcct      60
gtttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtgttgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctacagcaa tggcaacaac gttgcgcaaa ctattaactg gcgaactact tactctagct    600
```

```
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatgatgaa cgaaatagac agatcgctga gataggtgcc     840
tcactgatta agcattggta a                                              861

<210> SEQ ID NO 19
<211> LENGTH: 816
<212> TYPE: DNA
<213> ORGANISM: Artificial Sequence
<220> FEATURE:
<223> OTHER INFORMATION: kanamycin resistance gene

<400> SEQUENCE: 19
atgagccata ttcaacggga aacgtcttgc tctaggccgc gattaaattc caacatggat     60
gctgatttat atgggtataa atgggctcgc gataatgtcg ggcaatcagg tgcgacaatc    120
tatcgattgt atgggaagcc cgatgcgcca gagttgtttc tgaaacatgg caaaggtagc    180
gttgccaatg atgttacaga tgagatggtc agactaaact ggctgacgga atttatgcct    240
cttccgacca tcaagcattt tatccgtact cctgatgatg catggttact caccactgcg    300
atccccggga aaacagcatt ccaggtatta gaagaatatc ctgattcagg tgaaaatatt    360
gttgatgcgc tggcagtgtt cctgcgccgg ttgcattcga ttcctgtttg taattgtcct    420
tttaacagcg accgcgtatt tcgtctcgct caggcgcaat cacgaatgaa taacggtttg    480
gttgatgcga gtgattttga tgacgagcgt aatggctggc ctgttgaaca agtctggaaa    540
gaaatgcata acttttgcc attctcaccg gattcagtcg tcactcatgg tgatttctca     600
cttgataacc ttatttttga cgaggggaaa ttaataggtt gtattgatgt tggacgagtc    660
ggaatcgcag accgatacca ggatcttgcc atcctatgga actgcctcgg tgagttttct    720
ccttcattac agaaacggct ttttcaaaaa tatggtattg ataatcctga tatgaataaa    780
ttgcagtttc atttgatgct cgatgagttt ttctaa                              816

<210> SEQ ID NO 20
<211> LENGTH: 72
<212> TYPE: DNA
<213> ORGANISM: Artificial Sequence
<220> FEATURE:
<223> OTHER INFORMATION: primer

<400> SEQUENCE: 20
tggctccctg acgttttttt agccacgtat caattatagg tacttccatg aattaacccct   60 cactaaaggg cg                                                         72

<210> SEQ ID NO 21
<211> LENGTH: 73
<212> TYPE: DNA
<213> ORGANISM: Artificial Sequence
<220> FEATURE:
<223> OTHER INFORMATION: primer

<400> SEQUENCE: 21
gcagcgcaaa gctgcggatg atgacgagat tactgctgct gtgcagactg taatacgact     60
cactataggg ctc                                                        73

<210> SEQ ID NO 22
```

```
<211> LENGTH: 20
<212> TYPE: DNA
<213> ORGANISM: Artificial Sequence
<220> FEATURE:
<223> OTHER INFORMATION: primer

<400> SEQUENCE: 22
tgtcatcatg cgctacgctc                                                      20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cagttaagca agataatcag                                                      20

<210> SEQ ID NO 24
<211> LENGTH: 72
<212> TYPE: DNA
<213> ORGANISM: Artificial Sequence
<220> FEATURE:
<223> OTHER INFORMATION: primer

<400> SEQUENCE: 24
gatgaactaa acttgttacc gttatcacat tcaggagatg gagaaccatg aattaaccct          60
cactaaaggg cg                                                              72

<210> SEQ ID NO 25
<211> LENGTH: 73
<212> TYPE: DNA
<213> ORGANISM: Artificial Sequence
<220> FEATURE:
<223> OTHER INFORMATION: primer

<400> SEQUENCE: 25
ccttattatg acgggaaatg ccacccttt taccttagcc agtttgtttt taatacgact           60
cactataggg ctc                                                             73

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
ttacgtactg gcctgctcct gc                                                   22

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
gtcgggtaac ggtatcactg cg                                                   22

<210> SEQ ID NO 28
<211> LENGTH: 72
<212> TYPE: DNA
<213> ORGANISM: Artificial Sequence
```

-continued

```
<220> FEATURE:
<223> OTHER INFORMATION: primer

<400> SEQUENCE: 28 attttagta gcttaaatgt gattcaacat cactggagaa agtcttatga aattaaccct    60
cactaaaggg cg                                                      72

<210> SEQ ID NO 29
<211> LENGTH: 73
<212> TYPE: DNA
<213> ORGANISM: Artificial Sequence
<220> FEATURE:
<223> OTHER INFORMATION: primer

<400> SEQUENCE: 29 ctccctgga atgcagggga gcggcaagat taaaccagtt cgttcgggca taatacgact    60
cactataggg ctc                                                     73

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tcatcagcag cgtcaacggc                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cgctggtcac gggcttaccg                                              20

<210> SEQ ID NO 32
<211> LENGTH: 72
<212> TYPE: DNA
<213> ORGANISM: Artificial Sequence
<220> FEATURE:
<223> OTHER INFORMATION: primer

<400> SEQUENCE: 32
cgagcagatg atttactaaa aaagtttaac attatcagga gagcattatg aattaaccct    60
cactaaaggg cg                                                      72

<210> SEQ ID NO 33
<211> LENGTH: 73
<212> TYPE: DNA
<213> ORGANISM: Artificial Sequence
<220> FEATURE:
<223> OTHER INFORMATION: primer

<400> SEQUENCE: 33
ccgtttatgt tgccagacag cgctactgat taagcggatt ttttcgcttt taatacgact    60
cactataggg ctc                                                     73

<210> SEQ ID NO 34
<211> LENGTH: 20
<212> TYPE: DNA
```

```
<213> ORGANISM: Artificial Sequence
<220> FEATURE:
<223> OTHER INFORMATION: primer

<400> SEQUENCE: 34
ccgcactgac tatactctcg                                                   20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tgatcggcat tgcccagaag                                                   20

<210> SEQ ID NO 36
<211> LENGTH: 72
<212> TYPE: DNA
<213> ORGANISM: Artificial Sequence
<220> FEATURE:
<223> OTHER INFORMATION: primer

<400> SEQUENCE: 36
ctattgcctg actgtaccca caacggtgta tgcaagaggg ataaaaaatg aattaacccct      60 cactaaaggg cg                                                           72

<210> SEQ ID NO 37
<211> LENGTH: 74
<212> TYPE: DNA
<213> ORGANISM: Artificial Sequence
<220> FEATURE:
<223> OTHER INFORMATION: primer

<400> SEQUENCE: 37
acgcgtcata aaacgcgata tgcgaccaat cataaatcac cccgttgcgt ttaatacgac      60
tcactatagg gctc                                                         74

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
tggcgaggta aaaacagccc c                                                 21

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
aagcgcgatc acgaatgtta gc                                                22

<210> SEQ ID NO 40
<211> LENGTH: 72
<212> TYPE: DNA
<213> ORGANISM: Artificial Sequence
<220> FEATURE:
<223> OTHER INFORMATION: primer
```

-continued

<400> SEQUENCE: 40
cgctattcta gtttgtgata ttttttcgcc accacaagga gtggaaaatg aattaaccct    60
cactaaaggg cg    72

<210> SEQ ID NO 41
<211> LENGTH: 73
<212> TYPE: DNA
<213> ORGANISM: Artificial Sequence
<220> FEATURE:
<223> OTHER INFORMATION: primer

<400> SEQUENCE: 41
ggatggcgat actctgccat ccgtaatttt tactccactt cctgccagtt taatacgact    60
cactataggg ctc    73

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
cagactcacc gcgattccta ctg    23

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
cggtaaagtg atgcctgtgc c    21

<210> SEQ ID NO 44
<211> LENGTH: 72
<212> TYPE: DNA
<213> ORGANISM: Artificial Sequence
<220> FEATURE:
<223> OTHER INFORMATION: primer

<400> SEQUENCE: 44
agaaatgtgt ttctcaaacc gttcatttat cacaaaagga ttgttcgatg aattaaccct    60
cactaaaggg cg    72

<210> SEQ ID NO 45
<211> LENGTH: 74
<212> TYPE: DNA
<213> ORGANISM: Artificial Sequence
<220> FEATURE:
<223> OTHER INFORMATION: primer

<400> SEQUENCE: 45
cggcgactaa acgccgccgg ggatttattt tatttcttca gttcagccag ttaatacgac    60
tcactatagg gctc    74

<210> SEQ ID NO 46
<211> LENGTH: 20
<212> TYPE: DNA
<213> ORGANISM: Artificial Sequence
<220> FEATURE:

<223> OTHER INFORMATION: primer

<400> SEQUENCE: 46
gcagatttgc gcaacgctgg                                                   20

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
ctgccgtatg gatgaggctg g                                                 21

<210> SEQ ID NO 48
<211> LENGTH: 3348
<212> TYPE: DNA
<213> ORGANISM: Escherichia coli MG1655

<400> SEQUENCE: 48

| | | | | | |
|---|---|---|---|---|---|
| atgtcgagta | agttagtact | ggttctgaac | tgcggtagtt | cttcactgaa | atttgccatc | 60 |
| atcgatgcag | taaatggtga | agagtacctt | tctggtttag | ccgaatgttt | ccacctgccc | 120 |
| gaagcacgta | tcaaatggaa | aatggacggc | aataaacagg | aagcggcttt | aggtgcaggc | 180 |
| gccgctcaca | gcgaagcgct | caactttatc | gttaatacta | ttctggcaca | aaaaccagaa | 240 |
| ctgtctgcgc | agctgactgc | tatcggtcac | cgtatcgtac | acggcggcga | aaagtatacc | 300 |
| agctccgtag | tgatcgatga | gtctgttatt | cagggtatca | aagatgcagc | ttctttttgca | 360 |
| ccgctgcaca | acccggctca | cctgatcggt | atcgaagaag | ctctgaaatc | tttcccacag | 420 |
| ctgaaagaca | aaaacgttgc | tgtatttgac | accgcgttcc | accagactat | gccggaagag | 480 |
| tcttacctct | acgccctgcc | ttacaacctg | tacaaagagc | acggcatccg | tcgttacggc | 540 |
| gcgcacggca | ccagccactt | ctatgtaacc | caggaagcgg | caaaaatgct | gaacaaaccg | 600 |
| gtagaagaac | tgaacatcat | cacctgccac | ctgggcaacg | gtggttccgt | ttctgctatc | 660 |
| cgcaacggta | aatgcgttga | cacctctatg | ggcctgaccc | cgctggaagg | tctggtcatg | 720 |
| ggtacccgtt | ctggtgatat | cgatccggcg | atcatcttcc | acctgcacga | caccctgggc | 780 |
| atgagcgttg | acgcaatcaa | caaactgctg | accaaagagt | ctggcctgct | gggtctgacc | 840 |
| gaagtgacca | gcgactgccg | ctatgttgaa | gacaactacg | cgacgaaaga | agacgcgaag | 900 |
| cgcgcaatgg | acgtttactg | ccaccgcctg | gcgaaataca | tcggtgccta | cactgcgctg | 960 |
| atggatggtc | gtctggacgc | tgttgtattc | actggtggta | tcggtgaaaa | tgccgcaatg | 1020 |
| gttcgtgaac | tgtctctggg | caaactgggc | gtgctgggct | tgaagttga | tcatgaacgc | 1080 |
| aacctggctg | cacgtttcgg | caaatctggt | ttcatcaaca | aagaaggtac | ccgtcctgcg | 1140 |
| gtggttatcc | caaccaacga | gaactggtt | atcgcgcaag | acgcgagccg | cctgactgcc | 1200 |
| tgagtgtccc | gtattattat | gctgatccct | accggaacca | gcgtcggtct | gaccagcgtc | 1260 |
| agccttggcg | tgatccgtgc | aatggaacgc | aaaggcgttc | gtctgagcgt | tttcaaacct | 1320 |
| atcgctcagc | cgcgtaccgg | tggcgatgcg | cccgatcaga | ctacgactat | cgtgcgtgcg | 1380 |
| aactcttcca | ccacgacggc | cgctgaaccg | ctgaaaatga | gctacgttga | aggtctgctt | 1440 |
| tccagcaatc | agaaagatgt | gctgatgaa | gagatcgtcg | caaactacca | cgctaacacc | 1500 |
| aaagacgctg | aagtcgttct | ggttgaaggt | ctggtcccga | cacgtaagca | ccagtttgcc | 1560 |
| cagtctctga | actacgaaat | cgctaaaacg | ctgaatgcgg | aaatcgtctt | cgttatgtct | 1620 |

```
cagggcactg acaccccgga acagctgaaa gagcgtatcg aactgacccg caacagcttc    1680
ggcggtgcca aaaacaccaa catcaccggc gttatcgtta acaaactgaa cgcaccggtt    1740
gatgaacagg gtcgtactcg cccggatctg tccgagattt cgacgactc ttccaaagct    1800 aaagtaaaca atgttgatcc ggcgaagctg caagaatcca gcccgctgcc ggttctcggc    1860
gctgtgccgt ggagctttga cctgatcgcg actcgtgcga tcgatatggc tcgccacctg    1920
aatgcgacca tcatcaacga aggcgacatc aatactcgcc gcgttaaatc cgtcactttc    1980
tgcgcacgca gcattccgca catgctggag cacttccgtg ccggttctct gctggtgact    2040
tccgcagacc gtcctgacgt gctggtggcc gcttgcctgg cagccatgaa cggcgtagaa    2100
atcggtgccc tgctgctgac tggcggttac gaaatggacg cgcgcatttc taaactgtgc    2160
gaacgtgctt cgctaccgg cctgccggta tttatggtga acaccaacac ctggcagacc    2220
tctctgagcc tgcagagctt caacctggaa gttccggttg acgatcacga acgtatcgag    2280
aaagttcagg aatacgttgc taactacatc aacgctgact ggatcgaatc tctgactgcc    2340
acttctgagc gcagccgtcg tctgtctccg cctgcgttcc gttatcagct gactgaactt    2400
gcgcgcaaag cgggcaaacg tatcgtactg ccggaaggtg acgaaccgcg taccgttaaa    2460
gcagccgcta tctgtgctga acgtggtatc gcaacttgcg tactgctggg taatccggca    2520
gagatcaacc gtgttgcagc gtctcagggt gtagaactgg gtgcagggat tgaaatcgtt    2580
gatccagaag tggttcgcga aagctatgtt ggtcgtctgg tcgaactgcg taagaacaaa    2640
ggcatgaccg aaaccgttgc ccgcgaacag ctggaagaca acgtggtgct cggtacgctg    2700
atgctggaac aggatgaagt tgatggtctg gtttccggtg ctgttcacac taccgcaaac    2760
accatccgtc cgccgctgca gctgatcaaa actgcaccgg gcagctccct ggtatcttcc    2820
gtgttcttca tgctgctgcc ggaacaggtt tacgtttacg gtgactgtgc gatcaacccg    2880
gatccgaccg ctgaacagct ggcagaaatc gcgattcagt ccgctgattc cgctgcggcc    2940
ttcggtatcg aaccgcgcgt tgctatgctc tcctactcca ccggtacttc tggtgcaggt    3000
agcgacgtag aaaagttcg cgaagcaact cgtctggcgc aggaaaaacg tcctgacctg    3060
atgatcgacg gtccgctgca gtacgacgct gcggtaatgg ctgacgttgc gaaatccaaa    3120
gcgccgaact ctccggttgc aggtcgcgct accgtgttca tcttcccgga tctgaacacc    3180
ggtaacacca cctacaaagc ggtacagcgt tctgccgacc tgatctccat cgggccgatg    3240
ctgcagggta tgcgcaagcc ggttaacgac ctgtcccgtg gcgcactggt tgacgatatc    3300
gtctacacca tcgcgctgac tgcgattcag tctgcacagc agcagtaa               3348

<210> SEQ ID NO 49
<211> LENGTH: 1719
<212> TYPE: DNA
<213> ORGANISM: Escherichia coli MG1655

<400> SEQUENCE: 49
atgaaacaaa cggttgcagc ttatatcgcc aaaacactcg aatcggcagg ggtgaaacgc      60
atctggggag tcacaggcga ctctctgaac ggtcttagtg acagtcttaa tcgcatgggc     120
accatcgagt ggatgtccac ccgccacgaa gaagtggcgg cctttgccgc tggcgctgaa     180
gcacaactta gcggagaact ggcggtctgc gccggatcgt gcggccccgg caacctgcac     240
ttaatcaacg gcctgttcga ttgccaccgc aatcacgttc cggtactggc gattgccgct     300
catattccct ccagcgaaat tggcagcggc tatttccagg aaacccaccc acaagagcta     360
```

```
ttccgcgaat gtagtcacta ttgcgagctg gtttccagcc cggagcagat cccacaagta    420
ctggcgattg ccatgcgcaa agcggtgctt aaccgtggcg tttcggttgt cgtgttacca    480
ggcgacgtgg cgttaaaaacc tgcgccagaa ggggcaacca tgcactggta tcatgcgcca    540
caaccagtcg tgacgccgga agaagaagag ttacgcaaac tggcgcaact gctgcgttat    600
tccagcaata tcgccctgat gtgtggcagc ggctgcgcgg gggcgcataa agagttagtt    660
gagtttgccg ggaaaattaa agcgcctatt gttcatgccc tgcgcggtaa agaacatgtc    720
gaatacgata atccgtatga tgttggaatg accgggttaa tcggcttctc gtcaggtttc    780
cataccatga tgaacgccga cacgttagtg ctactcggca cgcaatttcc ctaccgcgcc    840
ttctacccga ccgatgccaa aatcattcag attgatatca acccagccag catcggcgct    900
cacagcaagg tggatatggc actggtcggc gatatcaagt cgactctgcg tgcattgctt    960
ccattggtgg aagaaaaagc cgatcgcaag tttctggata aagcgctgga agattaccgc   1020
gacgcccgca aagggctgga cgatttagct aaaccgagcg agaaagccat tcacccgcaa   1080
tatctggcgc agcaaattag tcattttgcc gccgatgacg ctattttcac ctgtgacgtt   1140
ggtacgccaa cggtgtgggc ggcacgttat ctaaaaatga acggcaagcg tcgcctgtta   1200
ggttcgttta ccaccggttc gatggctaac gccatgccgc aggcgctggg tgcgcaggcg   1260
acagagccag aacgtcaggt ggtcgccatg tgcggcgatg gcggttttag catgttgatg   1320
ggcgatttcc tctcagtagt gcagatgaaa ctgccagtga aaattgtcgt ctttaacaac   1380
agcgtgctgg gctttgtggc gatggagatg aaagctggtg gctatttgac tgacggcacc   1440
gaactacacg acacaaactt tgcccgcatt gccgaagcgt gcggcattac gggtatccgt   1500
gtagaaaaag cgtctgaagt tgatgaagcc ctgcaacgcg ccttctccat cgacggtccg   1560
gtgttggtgg atgtggtggt cgccaaagaa gagttagcca ttccaccgca gatcaaactc   1620
gaacaggcca aggtttcag cctgtatatg ctgcgcgcaa tcatcagcgg acgcggtgat   1680
gaagtgatcg aactggcgaa acaaactgg ctaaggtaa                           1719

<210> SEQ ID NO 50
<211> LENGTH: 1812
<212> TYPE: DNA
<213> ORGANISM: Escherichia coli MG1655

<400> SEQUENCE: 50
atggctgtta ctaatgtcgc tgaacttaac gcactcgtag agcgtgtaaa aaaagcccag     60
cgtgaatatg ccagttttcac tcaagagcaa gtagacaaaa tcttccgcgc cgccgctctg    120
gctgctgcag atgctcgaat cccactcgcg aaaatggccg ttgccgaatc cggcatgggt    180
atcgtcgaag ataaagtgat caaaaaccac tttgcttctg aatatatcta caacgcctat    240
aaagatgaaa aaacctgtgg tgttctgtct gaagacgaca cttttggtac catcactatc    300
gctgaaccaa tcggtattat ttgcggtatc gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga aagatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
```

```
gctgtacgtg aacgttttgc aacccacggc ggctatctgt tgcagggtaa agagctgaaa      840
gctgttcagg atgttatcct gaaaaacggt gcgctgaacg cggctatcgt tggtcagcca      900
gcctataaaa ttgctgaact ggcaggcttc tctgtaccag aaaacaccaa gattctgatc      960
ggtgaagtga ccgttgttga tgaaagcgaa ccgttcgcac atgaaaaact gtccccgact     1020
ctggcaatgt accgcgctaa agatttcgaa gacgcggtag aaaaagcaga gaaactggtt     1080
gctatgggcg gtatcggtca tacctcttgc ctgtacactg accaggataa ccaaccggct     1140
cgcgtttctt acttcggtca gaaaatgaaa acggcgcgta tcctgattaa caccccagcg     1200
tctcagggtg gtatcggtga cctgtataac ttcaaactcg caccttccct gactctgggt     1260
tgtggttctt ggggtggtaa ctccatctct gaaaacgttg gtccgaaaca cctgatcaac     1320
aagaaaaccg ttgctaagcg agctgaaaac atgttgtggc acaaacttcc gaaatctatc     1380
tacttccgcc gtggctccct gccaatcgcg ctggatgaag tgattactga tggccacaaa     1440
cgtgcgctca tcgtgactga ccgcttcctg ttcaacaatg ttatgctga tcagatcact      1500 tccgtactga aagcagcagg cgttgaaact gaagtcttct tcgaagtaga agcggacccg     1560 acccctgagca tcgttcgtaa aggtgcagaa ctggcaaact ccttcaaacc agacgtgatt    1620
atcgcgctgg gtggtggttc cccgatggac gccgcgaaga tcatgtgggt tatgtacgaa    1680
catccggaaa ctcacttcga gagctggcg ctgcgcttta tggatatccg taaacgtatc     1740
tacaagttcc cgaaaatggg cgtgaaagcg aaaatgatcg ctgtcaccac cacttctggt    1800
acaggttctg aa                                                         1812

<210> SEQ ID NO 51
<211> LENGTH: 990
<212> TYPE: DNA
<213> ORGANISM: Escherichia coli MG1655

<400> SEQUENCE: 51
atgaaactcg ccgtttatag cacaaaacag tacgacaaga agtacctgca acaggtgaac       60
gagtcctttg gctttgagct ggaattttt gactttctgc tgacggaaaa aaccgctaaa      120
actgccaatg gctgcgaagc ggtatgtatt ttcgtaaacg atgacggcag ccgcccggtg     180
ctggaagagc tgaaaaagca cggcgttaaa tatatcgccc tgcgctgtgc cggttttcaat     240 aacgtcgacc ttgacgcggc aaaagaactg gggctgaaag tagtccgtgt tccagcctat    300
gatccagagg ccgttgctga cacgccatc ggtatgatga tgacgctgaa ccgccgtatt     360
caccgcgcgt atcagcgtac ccgtgatgct aacttctctc tggaaggtct gaccggcttt    420
actatgtatg gcaaaacggc aggcgttatc ggtaccggta aaatcggtgt ggcgatgctg     480
cgcattctga aggttttgg tatgcgtctg ctggcgttcg atccgtatcc aagtgcagcg     540
gcgctggaac tcggtgtgga gtatgtcgat ctgccaaccc tgttctctga atcagacgtt    600
atctctctgc actgcccgct gacaccggaa aactatcatc tgttgaacga agccgccttc    660
gaacagatga aaaatggcgt gatgatcgtc aataccagtc gcggtgcatt gattgattct    720
caggcagcaa ttgaagcgct gaaaaatcag aaaattggtt cgttgggtat ggacgtgtat    780
gagaacgaac gcgatctatt ctttgaagat aaatccaacg acgtgatcca ggatgacgta    840
ttccgtcgcc tgtctgcctg ccacaacgtg ctgtttaccg ggcaccaggc attcctgaca    900
gcagaagctc tgaccagtat ttctcagact acgctgcaaa acttaagcaa tctggaaaaa    960
ggcgaaacct gcccgaacga actggtttaa                                     990
```

<210> SEQ ID NO 52
<211> LENGTH: 1716
<212> TYPE: DNA
<213> ORGANISM: Escherichia coli MG1655

<400> SEQUENCE: 52

```
atgtcttcca tgacaacaac tgataataaa gccttttga atgaacttgc tcgtctggtg      60
ggttcttcac acctgctcac cgatcccgca aaaacggccc gctatcgcaa gggcttccgt    120
tctggtcagg gcgacgcgct ggctgtcgtt ttccctggct cactactaga attgtggcgg    180
gtgctgaaag cctgcgtcac cgccgacaaa attattctga tgcaggccgc caatacaggc    240
ctgaccgaag atcgacgcc aaacggtaac gattatgatc gcgatgtcgt tatcatcagc    300
accctgcgtc tcgacaagct gcacgttctt ggcaagggcg aacaggtgct ggcctatccg    360
ggcaccacgc tctattcgct ggaaaaagcc ctcaaaccgc tgggacgcga accgcactca    420
gtgattggat catcgtgtat aggcgcatcg gtcatcggcg gtatttgtaa caactccggc    480
ggctcgctgg tgcaacgtgg cccggcgtat accgaaatgt cgttattcgc gcgtataaat    540
gaagacggca aactgacgct ggtgaaccat ctggggattg atctgggcga acgccggag    600
cagatcctta gcaagctgga tgatgatcgc atcaaagatg acgatgtgcg tcacgatggt    660
cgtcacgccc acgattatga ctatgtccac cgcgttcgtg atattgaagc cgacacgccc    720
gcacgttata acgccgatcc tgatcggtta tttgaatctt ctggttgcgc cgggaagctg    780
gcggtctttg cagtacgtct tgataccttc gaagcggaaa aaatcagca ggtgttttat     840
atcggcacca accagccgga agtgctgacc gaaatccgcc gtcatattct ggctaacttc    900
gaaaatctgc cggttgccgg ggaatatatg caccgggata tctacgatat tgcggaaaaa    960
tacggcaaag acaccttcct gatgattgat aagttaggca ccgacaagat gccgttcttc   1020
tttaatctca agggacgcac cgatgcgatg ctggagaaag tgaaattctt ccgtccgcat   1080
tttactgacc gtgcgatgca aaaattcggt cacctgttcc ccagccattt accgccgcgc   1140
atgaaaaact ggcgcgataa atacgagcat catctgctgt aaaaatggc gggcgatggc    1200
gtgggcgaag ccaaatcgtg gctggtggat tatttcaaac aggccgaagg cgatttcttt   1260
gtctgtacgc cggaggaagg cagcaaagcg ttttacacc gtttcgccgc tgcgggcgca    1320
gcaattcgtt atcaggcggt gcattccgat gaagtcgaag acattctggc gttggatatc   1380
gctctgcggc gtaacgacac cgagtggtat gagcatttac cgccggagat cgacagccag   1440
ctggtgcaca gctctatta cggccatttt atgtgctatg tcttccatca ggattacata    1500
gtgaaaaaag gcgtggatgt gcatgcgtta aaagaacaga tgctggaact gctacagcag   1560
cgcggcgcgc agtaccctgc cgagcataac gtcggtcatt tgtataaagc accggagacg   1620
ttgcagaagt tctatcgcga aacgatccg accaacagca tgaatccggg gatcggtaaa    1680
accagtaaac ggaaaaactg gcaggaagtg gagtaa                              1716
```

<210> SEQ ID NO 53
<211> LENGTH: 1313
<212> TYPE: DNA
<213> ORGANISM: Escherichia coli MG1655

<400> SEQUENCE: 53

```
atgaaaacaa aattgatgac attacaagac gccaccggct tctttcgtga cggcatgacc      60
atcatggtgg gcggatttat ggggattggc actccatccc gctggttga agcattactg    120
gaatctggtg ttcgcgacct gacattgata gccaatgata ccgcgtttgt tgataccggc    180
```

```
atcggtccgc tcatcgtcaa tggtcgagtc cgcaaagtga ttgcttcaca tatcggcacc      240
aacccggaaa caggtcggcg catgatatct ggtgagatgg acgtcgttct ggtgccgcaa      300
ggtacgctaa tcgagcaaat tcgctgtggt ggagctggac ttggtggttt tctcaccccca     360 acgggtgtcg gcaccgtcgt agaggaaggc aaacagacac tgacactcga cggtaaaacc      420
tggctgctcg aacgcccact gcgcgccgac ctggcgctaa ttcgcgctca tcgttgcgac      480
acacttggca acctgaccta tcaacttagc gcccgcaact ttaaccccct gatagccctt      540
gcggctgata tcacgctggt agagccagat gaactggtcg aaaccggcga gctgcaacct      600
gaccatattg tcaccctgg tgccgttatc gaccacatca tcgtttcaca ggagagcaaa       660
taatggatgc gaaacaacgt attgcgcgcc gtgtggcgca agagcttcgt gatggtgaca      720
tcgttaactt agggatcggt ttacccacaa tggtcgccaa ttatttaccg gagggtattc      780
atatcactct gcaatcggaa acggcttcc tcggtttagg cccggtcacg acagcgcatc      840
cagatctggt gaacgctggc gggcaaccgt gcggtgtttt acccggtgca gccatgtttg     900
atagcgccat gtcatttgcg ctaatccgtg gcggtcatat tgatgcctgc gtgctcggcg     960
gtttgcaagt agacgaagaa gcaaaacctcg cgaactgggt agtgcctggg aaaatggtgc    1020
ccggtatggg tggcgcgatg gatctggtga ccgggtcgcg caaagtgatc atcgccatgg    1080
aacattgcgc caaagatggt tcagcaaaaa ttttgcgccg ctgcaccatg ccactcactg     1140
cgcaacatgc ggtgcatatg ctggttactg aactggctgt ctttcgtttt attgacggca    1200
aaatgtggct caccgaaatt gccgacgggt gtgatttagc caccgtgcgt gccaaaacag     1260
aagctcggtt tgaagtcgcc gccgatctga atacgcaacg gggtgattta tga            1313

<210> SEQ ID NO 54
<211> LENGTH: 2379
<212> TYPE: DNA
<213> ORGANISM: Escherichia coli MG1655

<400> SEQUENCE: 54
atgtccaaca atggctcgtc accgctggtg ctttggtata accaactcgg catgaatgat       60
gtagacaggg ttggggcaa aaatgcctcc ctgggtgaaa tgattactaa tctttccgga      120
atgggtgttt ccgttccgaa tggtttcgcc acaaccgccg acgcgtttaa ccagtttctg      180
gaccaaagcg gcgtaaacca gcgcatttat gaactgctgg ataaaacgga tattgacgat      240
gttactcagc ttgcgaaagc gggcgcgcaa atccgccagt ggattatcga cactcccttc      300
cagcctgagc tggaaaacgc catccgcgaa gcctatgcac agctttccgc cgatgacgaa      360
aacgcctctt ttgcggtgcg ctcctccgcc accgcagaag atatgccgga cgcttctttt     420
gccggtcagc aggaaaacctt cctcaacgtt cagggttttg acgccgttct cgtggcagtg      480
aaacatgtat ttgcttctct gttttaacgat cgcgccatct cttatcgtgt gcaccagggt      540
tacgatcacc gtggtgtggc gctctccgcc ggtgttcaac ggatggtgcg ctctgacctc      600
gcatcatctg gcgtgatgtt ctccattgat accgaatccg gctttgacca ggtggtgttt      660
atcacttccg catggggcct tggtgagatg gtcgtgcagg gtgcggttaa cccggatgag      720
ttttacgtgc ataaaccgac actggcggcg aatcgcccgg ctatcgtgcg ccgcaccatg      780
gggtcgaaaa aaatccgcat ggtttacgcg ccgacccagg agcacggcaa gcaggttaaa      840
atcgaagacg taccgcagga acagcgtgac atcttctctcgc tgaccaacga agaagtgcag    900
gaactggcaa acaggccgt acaaattgag aaacactacg gtcgcccgat ggatattgag     960
```

```
tgggcgaaag atggccacac cggtaaactg ttcattgtgc aggcgcgtcc ggaaaccgtg      1020
cgctcacgcg gtcaggtcat ggagcgttat acgctgcatt cacagggtaa gattatcgcc      1080
gaaggccgtg ctatcggtca tcgcatcggt gcgggtccgg tgaaagtcat ccatgacatc      1140
agcgaaatga accgcatcga acctggcgac gtgctggtta ctgacatgac cgacccggac      1200
tgggaaccga tcatgaagaa agcatctgcc atcgtcacca accgtggcgg tcgtacctgt      1260
cacgcggcga tcatcgctcg tgaactgggc attccggcgg tagtgggctg tggagatgca      1320
acagaacgga tgaaagacgg tgagaacgtc actgtttctt gtgccgaagg tgataccggt      1380
tacgtctatg cggagttgct ggaatttagc gtgaaaagct ccagcgtaga acgatgccg       1440 gatctgccgt tgaaagtgat gatgaacgtc ggtaacccgg accgtgcttt cgacttcgcc      1500
tgcctaccga acgaaggcgt gggccttgcg cgtctggaat ttatcatcaa ccgtatgatt      1560
ggcgtccacc cacgcgcact gcttgagttt gacgatcagg aaccgcagtt gcaaaacgaa      1620
atccgcgaga tgatgaaagg ttttgattct ccgcgtgaat tttacgttgg tcgtctgact      1680
gaagggatcg cgacgctggg tgccgcgttt tatccgaagc gcgtcattgt ccgtctctct      1740
gattttaaat cgaacgaata tgccaacctg gtcggtggtg agcgttacga gccagatgaa      1800
gagaacccga tgctcggctt ccgtggcgcg ggccgctatg tttccgacag cttccgcgac      1860
tgtttcgcgc tggagtgtga agcagtgaaa cgtgtgcgca acgacatggg actgaccaac      1920
gttgagatca tgatcccgtt cgtgcgtacc gtagatcagg cgaaagcggt ggttgaagaa      1980
ctggcgcgtc aggggctgaa acgtggcgag aacgggctga aaatcatcat gatgtgtgaa      2040
atcccgtcca acgccttgct ggccgagcag ttcctcgaat atttcgacgg cttctcaatt      2100
ggctcaaacg atatgacgca gctggcgctc ggtctggacc gtgactccgg cgtggtgtct      2160
gaattgttcg atgagcgcaa cgatgcgtg aaagcactgc tgtcgatggc tatccgtgcc       2220
gcgaagaaac agggcaaata tgtcgggatt tgcggtcagg gtccgtccga ccacgaagac      2280
tttgccgcat ggttgatgga agagggatc gatagcctgt ctctgaaccc ggacaccgtg       2340
gtgcaaacct ggttaagcct ggctgaactg aagaaataa                              2379
```

<210> SEQ ID NO 55
<211> LENGTH: 3368
<212> TYPE: DNA
<213> ORGANISM: Artificial Sequence
<220> FEATURE:
<223> OTHER INFORMATION: promoter, marker, FRT site, terminator

<400> SEQUENCE: 55

```
cgaggcagca gatcaattcg cgcgcgaagg cgaagcggca tgcatttacg ttgacaccat        60
cgaatggtgc aaaacctttc gcggtatggc atgatagcgc ccggaagaga gtcaattcag       120
ggtggtgaat gtgaaaccag taacgttata cgatgtcgca gagtatgccg gtgtctctta      180
tcagaccgtt tcccgcgtgg tgaaccaggc cagccacgtt tctgcgaaaa cgcgggaaaa      240
agtggaagcg gcgatggcgg agctgaatta cattcccaac cgcgtggcac aacaactggc      300
gggcaaacag tcgttgctga ttggcgttgc cacctccagt ctggccctgc acgcgccgtc       360
gcaaattgtc gcggcgatta aatctcgcgc cgatcaactg ggtgccagcg tggtggtgtc      420
gatggtagaa cgaagcggcg tcgaagcctg taaagcggcg gtgcacaatc ttctcgcgca      480
acgcgtcagt gggctgatca ttaactatcc gctggatgac caggatgcca ttgctgtgga      540
agctgcctgc actaatgttc cggcgttatt tcttgatgtc tctgaccaga cacccatcaa      600
cagtattatt ttctcccatg aagacggtac gcgactgggc gtggagcatc tggtcgcatt       660
```

```
gggtcaccag caaatcgcgc tgttagcggg cccattaagt tctgtctcgg cgcgtctgcg    720
tctggctggc tggcataaat atctcactcg caatcaaatt cagccgatag cggaacggga    780
aggcgactgg agtgccatgt ccggttttca acaaaccatg caaatgctga atgagggcat    840
cgttcccact gcgatgctgg ttgccaacga tcagatggcg ctgggcgcaa tgcgcgccat    900
taccgagtcc gggctgcgcg ttggtgcgga tatctcggta gtgggatacg acgataccga    960
agacagctca tgttatatcc cgccgttaac caccatcaaa caggattttc gcctgctggg   1020
gcaaaccagc gtggaccgct tgctgcaact ctctcagggc caggcggtga agggcaatca   1080
gctgttgccc gtctcactgg tgaaaagaaa aaccaccctg cgcccaata cgcaaaccgc    1140 ctctccccgc gcgttggccg attcattaat gcagctggca cgacaggttt cccgactgga   1200
aagcgggcag tgagcgcaac gcaattaatg tgagttagcg cgaattgatc tggtttgaca   1260
gcttatcatc gactgcacgg tgcaccaatg cttctggcgt caggcagcca tcggaagctg   1320
tggtatggct gtgcaggtcg taaatcactg cataattcgt gtcgctcaag gcgcactccc   1380
gttctggata atgttttttg cgccgacatc ataacggttc tggcaaatat tctgaaatga   1440
gctgttgaca attaatcatc cggctcgtat aatgtgtgga attgtgagcg gataacaatt   1500
tcacacagga aacagaccat ggaattcgag ctcggtaccc ggggatcctc tagagtcgac   1560
ctgcaggcat gcaagcttgg ctgttttggc ggatgagaga agattttcag cctgatacag   1620
attaaatcag aacgcagaag cggtctgata aacagaatt tgcctggcgg cagtagcgcg   1680
gtggtcccac ctgaccccat gccgaactca gaagtgaaac gccgtagcgc cgatggtagt   1740
gtggggtctc cccatgcgag agtagggaac tgccaggcat caaataaaac gaaaggctca   1800
gtcgaaagac tgggcctttc gttttatctg ttgtttgtcg gtgaacgctc tcctgagtag   1860
gacaaatccg ccgggagcgg atttgaacgt tgcgaagcaa cggcccggag ggtggcgggc   1920
aggacgcccg ccataaactg ccaggcatca aattaagcag aaggccatcc tgacggatgg   1980
cctttttgcg tttctacaaa ctcttttgt ttattttct aaatacattc aaatatgtat    2040
ccgctcatga caataaacc ccaattcgat ggggatccgt cgacctgcag ttcgaagttc    2100
ctattctcta gaaagtatag gaacttcaga gcgcttttga agctcacgct gccgcaagca   2160
ctcagggcgc aagggctgct aaaggaagcg gaacacgtag aaagccagtc gcagaaacg    2220 gtgctgaccc cggatgaatg tcagctactg ggctatctgg acaagggaaa acgcaagcgc   2280
aaagagaaag caggtagctt gcagtgggct tacatggcga tagctagact gggcggtttt   2340
atggacagca agcgaaccgg aattgccagc tggggcgccc tctggtaagg ttgggaagcc   2400
ctgcaaagta aactggatgg ctttcttgcc gccaaggatc tgatggcgca ggggatcaag   2460
atctgatcaa gagacaggat gaggatcgtt tcgcatgatt gaacaagatg gattgcacgc   2520
aggttctccg gccgcttggg tggagaggct attcggctat gactgggcac aacagacaat   2580
cggctgctct gatgccgccg tgttccggct gtcagcgcag gggcgcccgg ttcttttgt    2640 caagaccgac ctgtccggtg ccctgaatga actgcaggac gaggcagcgc ggctatcgtg   2700
gctggccacg acgggcgttc cttgcgcagc tgtgctcgac gttgtcactg aagcgggaag   2760
ggactggctg ctattgggcg aagtgccggg gcaggatctc ctgtcatctc accttgctcc   2820
tgccgagaaa gtatccatca tggctgatgc aatgcggcgg ctgcatacgc ttgatccggc   2880
tacctgccca ttcgaccacc aagcgaaaca tcgcatcgag cgagcacgta tcggatgga   2940 agccggtctt gtcgatcagg atgatctgga cgaagagcat caggggctcg cgccagccga   3000
```

```
actgttcgcc aggctcaagg cgcgcatgcc cgacggcgag gatctcgtcg tgacccatgg    3060
cgatgcctgc ttgccgaata tcatggtgga aaatggccgc ttttctggat tcatcgactg    3120
tggccggctg ggtgtggcgg accgctatca ggacatagcg ttggctaccc gtgatattgc    3180
tgaagagctt ggcggcgaat gggctgaccg cttcctcgtg ctttacggta tcgccgctcc    3240
cgattcgcag cgcatcgcct tctatcgcct tcttgacgag ttcttctaat aagggggatct    3300 tgaagttcct attccgaagt tcctattctc tagaaagtat aggaacttcg aagcagctcc    3360
agcctaca                                                             3368
```

<210> SEQ ID NO 56
<211> LENGTH: 38
<212> TYPE: DNA
<213> ORGANISM: Artificial Sequence
<220> FEATURE:
<223> OTHER INFORMATION: primer

<400> SEQUENCE: 56
cgaattcagg aggagaaatt atgcaaacgg aacacgtc                            38

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
cctgcaggtc gaaattctta tttaagctgg gtaaa                               35

<210> SEQ ID NO 58
<211> LENGTH: 42
<212> TYPE: DNA
<213> ORGANISM: Artificial Sequence
<220> FEATURE:
<223> OTHER INFORMATION: primer

<400> SEQUENCE: 58
ggaattcagg aggtaataaa atatgcttcg ttcgttgctc ag                       42

<210> SEQ ID NO 59
<211> LENGTH: 34
<212> TYPE: DNA
<213> ORGANISM: Artificial Sequence
<220> FEATURE:
<223> OTHER INFORMATION: primer

<400> SEQUENCE: 59
caagcttgat cactagttac gcttcgttga tgtg                                34

<210> SEQ ID NO 60
<211> LENGTH: 39
<212> TYPE: DNA
<213> ORGANISM: Artificial Sequence
<220> FEATURE:
<223> OTHER INFORMATION: primer

<400> SEQUENCE: 60
ggaattcagg aggattcact gatggatagc accccccac                           39

<210> SEQ ID NO 61
<211> LENGTH: 35
<212> TYPE: DNA
<213> ORGANISM: Artificial Sequence

```
<220> FEATURE:
<223> OTHER INFORMATION: primer

<400> SEQUENCE: 61
cctgcaggtc gactctagtt aaggtttagt taacc                              35

<210> SEQ ID NO 62
<211> LENGTH: 36
<212> TYPE: DNA
<213> ORGANISM: Artificial Sequence
<220> FEATURE:
<223> OTHER INFORMATION: primer

<400> SEQUENCE: 62
tctagaggag gataggacat gacgacaaat cgtaag                             36

<210> SEQ ID NO 63
<211> LENGTH: 32
<212> TYPE: DNA
<213> ORGANISM: Artificial Sequence
<220> FEATURE:
<223> OTHER INFORMATION: primer

<400> SEQUENCE: 63
gtcgactcta gttacgcctt tttcatctga tc                                 32

<210> SEQ ID NO 64
<211> LENGTH: 44
<212> TYPE: DNA
<213> ORGANISM: Artificial Sequence
<220> FEATURE:
<223> OTHER INFORMATION: primer

<400> SEQUENCE: 64
gaattcgagc tcaggaggta ataaatatgg cttgctctgt atcc                    44

<210> SEQ ID NO 65
<211> LENGTH: 50
<212> TYPE: DNA
<213> ORGANISM: Artificial Sequence
<220> FEATURE:
<223> OTHER INFORMATION: primer

<400> SEQUENCE: 65
ggatccgccg ccacccgagc caccgccacc gcgttcgaac ggcagaattg              50

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
ggatccatgg cttgctctgt atccactgag                                    30

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
ctgcaggtcg acttagcgtt cgaacggcag                                    30
```

<210> SEQ ID NO 68
<211> LENGTH: 44
<212> TYPE: DNA
<213> ORGANISM: Artificial Sequence
<220> FEATURE:
<223> OTHER INFORMATION: primer

<400> SEQUENCE: 68
gaattcgagc tcaggaggta ataaatatgc aaacggaaca cgtc                44

<210> SEQ ID NO 69
<211> LENGTH: 48
<212> TYPE: DNA
<213> ORGANISM: Artificial Sequence
<220> FEATURE:
<223> OTHER INFORMATION: primer

<400> SEQUENCE: 69
ggatccgccg ccacccgagc caccgccacc tttaagctgg gtaaatgc             48

<210> SEQ ID NO 70
<211> LENGTH: 33
<212> TYPE: DNA
<213> ORGANISM: Artificial Sequence
<220> FEATURE:
<223> OTHER INFORMATION: primer

<400> SEQUENCE: 70
ggatccatgc aaacggaaca cgtcatttta ttg                             33

<210> SEQ ID NO 71
<211> LENGTH: 32
<212> TYPE: DNA
<213> ORGANISM: Artificial Sequence
<220> FEATURE:
<223> OTHER INFORMATION: primer

<400> SEQUENCE: 71
ctgcaggtcg acttatttaa gctgggtaaa tg                              32

<210> SEQ ID NO 72
<211> LENGTH: 46
<212> TYPE: DNA
<213> ORGANISM: Artificial Sequence
<220> FEATURE:
<223> OTHER INFORMATION: primer

<400> SEQUENCE: 72
gaattcgagc tcaggaggta ataaatatgg atagcacccc ccaccg               46

<210> SEQ ID NO 73
<211> LENGTH: 50
<212> TYPE: DNA
<213> ORGANISM: Artificial Sequence
<220> FEATURE:
<223> OTHER INFORMATION: primer

<400> SEQUENCE: 73
ggatccgccg ccacccgagc caccgccacc aggtttagtt aacctttgtc           50

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
ggatccatgg atagcacccc ccaccgtaag                                30

<210> SEQ ID NO 75
<211> LENGTH: 33
<212> TYPE: DNA
<213> ORGANISM: Artificial Sequence
<220> FEATURE:
<223> OTHER INFORMATION: primer

<400> SEQUENCE: 75
ctgcaggtcg acttaaggtt tagttaacct ttg                             33

<210> SEQ ID NO 76
<211> LENGTH: 1062
<212> TYPE: DNA
<213> ORGANISM: Escherichia coli MG1655

<400> SEQUENCE: 76
atggctatcg acgaaaacaa acagaaagcg ttggcggcag cactgggcca gattgagaaa      60
caatttggta aaggctccat catgcgcctg ggtgaagacc gttccatgga tgtggaaacc     120
atctctaccg gttcgctttc actggatatc gcgcttgggg caggtggtct gccgatgggc     180
cgtatcgtcg aaatctacgg accggaatct tccggtaaaa ccacgctgac gctgcaggtg     240
atcgccgcag cgcagcgtga aggtaaaacc tgtgcgttta tcgatgctga acacgcgctg     300
gacccaatct acgcacgtaa actgggcgtc gatatcgaca acctgctgtg ctcccagccg     360
gacaccggcg agcaggcact ggaaatctgt gacgccctgg cgcgttctgg cgcagtagac     420
gttatcgtcg ttgactccgt ggcggcactg acgccgaaag cggaaatcga aggcgaaatc     480
ggcgactctc acatgggcct tgcggcacgt atgatgagcc aggcgatgcg taagctggcg     540
ggtaacctga gcagtccaa cacgctgctg atcttcatca accagatccg tatgaaaatt     600
ggtgtgatgt tcggtaaccc ggaaaccact accggtggta acgcgctgaa attctacgcc     660
tctgttcgtc tcgacatccg tcgtatcggc gcggtgaaag agggcgaaaa cgtggtgggt     720
agcgaaaccc gcgtgaaagt ggtgaagaac aaaatcgctg cgccgtttaa acaggctgaa     780
ttccagatcc tctacggcga aggtatcaac ttctacggcg aactggttga cctgggcgta     840
aaagagaagc tgatcgagaa agcaggcgcg tggtacagct acaaaggtga aagatcggt      900 cagggtaaag cgaatgcgac tgcctggctg aaagataacc cggaaaccgc gaaagagatc     960
gagaagaaag tacgtgagtt gctgctgagc aacccgaact caacgccgga tttctctgta    1020
gatgatagcg aaggcgtagc agaaactaac gaagattttt aa                       1062

<210> SEQ ID NO 77
<211> LENGTH: 453
<212> TYPE: DNA
<213> ORGANISM: Escherichia coli MG1655

<400> SEQUENCE: 77
gtgaaggata aagtgtataa gcgtcccgtt tcgatcttag tggtcatcta cgcacaagat      60
acgaaacggg tgctgatgtt gcagcggcgt gacgatcccg atttctggca gtcggtaacc     120
ggcagcgtgg aagagggtga aaccgcgccg caagctgcca tgcgcgaagt aaaggaagag     180
gtcaccattg atgttgtcgc tgaacaactg accttaattg actgtcagcg cacggtagag     240
tttgaaattt tttcacattt acgtcatcgc tatgcgccgg gcgtgacgcg taatacggaa     300

```
tcatggttct gtcttgcgct tccgcacgag cggcagatcg ttttcactga acatctggct    360
tacaagtggc ttgatgcgcc tgctgcggcg gcgctcacta agtcctggag caaccggcag    420
gcgattgaac agtttgtaat taacgctgcc tga                                 453
```

```
<210> SEQ ID NO 78
<211> LENGTH: 74
<212> TYPE: DNA
<213> ORGANISM: Artificial Sequence
<220> FEATURE:
<223> OTHER INFORMATION: nudB-F primer

<400> SEQUENCE: 78
```

```
ataactatgt gaatgggatg agcgaaggca gtcaacgaag aggcagcgtg catatttatt    60
acctccttgt aggc                                                      74
```

```
<210> SEQ ID NO 79
<211> LENGTH: 74
<212> TYPE: DNA
<213> ORGANISM: Artificial Sequence
<220> FEATURE:
<223> OTHER INFORMATION: nudB-R primer

<400> SEQUENCE: 79
```

```
taaaaatatc tccagatagc cctgcctgtt caggcagcgt taattacaaa catatgaata    60
tcctccttag ttcc                                                      74
```

```
<210> SEQ ID NO 80
<211> LENGTH: 23
<212> TYPE: DNA
<213> ORGANISM: Artificial Sequence
<220> FEATURE:
<223> OTHER INFORMATION: nudB-CF-F1 primer

<400> SEQUENCE: 80
```

```
caggaccgta accttcgtag atg                                            23
```

```
<210> SEQ ID NO 81
<211> LENGTH: 21
<212> TYPE: DNA
<213> ORGANISM: Artificial Sequence
<220> FEATURE:
<223> OTHER INFORMATION: nudB-CF-F2

<400> SEQUENCE: 81
```

```
caaactctac cgtgcgctga c                                              21
```

```
<210> SEQ ID NO 82
<211> LENGTH: 21
<212> TYPE: DNA
<213> ORGANISM: Artificial Sequence
<220> FEATURE:
<223> OTHER INFORMATION: nudB-CF-R primer

<400> SEQUENCE: 82
```

```
gaccgtctga ccatgctgct g                                              21
```

```
<210> SEQ ID NO 83
<211> LENGTH: 70
<212> TYPE: DNA
<213> ORGANISM: Artificial Sequence
<220> FEATURE:
<223> OTHER INFORMATION: flagella-F primer

<400> SEQUENCE: 83
```

```
ttccactttg ccaataacgc cgtccataat cagccacgag gtgcgcgatg ggggatccgt    60
cgacctgcag                                                          70
```

<210> SEQ ID NO 84
<211> LENGTH: 80
<212> TYPE: DNA
<213> ORGANISM: Artificial Sequence
<220> FEATURE:
<223> OTHER INFORMATION: flagella-R primer

<400> SEQUENCE: 84

```
agacgcggat tacggtgcta cctctgacgt taggcgaaaa tatcaacgcc catatttatt    60
acctccttgt aggctggagc                                               80
```

<210> SEQ ID NO 85
<211> LENGTH: 21
<212> TYPE: DNA
<213> ORGANISM: Artificial Sequence
<220> FEATURE:
<223> OTHER INFORMATION: FlaCF-F primer

<400> SEQUENCE: 85

```
gagtgaattt ttctgcctgc g                                             21
```

<210> SEQ ID NO 86
<211> LENGTH: 22
<212> TYPE: DNA
<213> ORGANISM: Artificial Sequence
<220> FEATURE:
<223> OTHER INFORMATION: FlaCF-R primer

<400> SEQUENCE: 86

```
gcttgctttt cttgcttatc gc                                            22
```

<210> SEQ ID NO 87
<211> LENGTH: 1659
<212> TYPE: DNA
<213> ORGANISM: Escherichia coli

<400> SEQUENCE: 87

```
atgaatgcga ctgcagccca gacaaaatct cttgagtggc ttaatcgcct gcgtgcgaat    60
ccgaaaattc cattgattgt tgccggttcc gcggcagtgg cggtcatggt cgcactgatc   120
ctgtgggcga agcccccga ctaccgcaca ttattcagca atctttccga tcaggatggt   180
ggcgcaattg tcagccaact gacgcaaatg aatattcctt accgcttcag cgaagccagc   240
ggcgctattg aagttccggc agataaagtt cacgaactgc gtctgcgcct ggcacaacaa   300
ggtttgccaa aaggcggcgc ggtcggtttc gaactgcttg atcaggaaaa gtttggtatc   360
agccagttca gcgaacaggt gaattatcag cgggcgctgg aaggcgagct ttctcgtacc   420
atcgaaacta tcggcccggt aaaggggcg cgcgtacatc tggcaatgcc gaaaccgtct   480
ttattcgtcc gtgaacaaaa atccccttct gcatcggtga cggtaaatct gttacccggc   540
cgcgcactcg atgaagggca aattagcgcc attgtgcatc tggttttccag cgccgttgct   600 ggtctgccgc cgggaaacgt cacgctggtg atcagggcg acatctgtt aacccagtcc   660 aataccagcg gcgcgatct taatgacgct cagttgaaat atgccagcga tgtcgaaggc   720
cgtattcagc ggcgtattga agcgatcctg tcgcctattg ttggtaacgg taatattcac   780
gcccaggtta cggcgcagct ggacttcgcc agtaaagaac aaacggaaga acagtatcgc   840
```

```
cctaacggtg atgaatctca tgcggcgctt cgttcacgcc agcttaatga gagcgagcaa    900
agcggttccg gttatccggg cggcgtaccg ggggcgttgt cgaatcaacc ggcacctgcg    960
aataacgcgc caatcagcac gcctccggca aatcaaaata accgccagca gcaggcgagc   1020
accaccagca atagtgggcc gcgtagcaca cagcggaatg aaaccagtaa ctacgaagtc   1080
gatcgcacca ttcgtcatac caaaatgaac gtgggcgatg tgcaacgtct gtcagtcgcg   1140
gtcgtggtga attacaaaac cttgccagat ggcaaaccgt tgcctctcag caacgaacag   1200
atgaagcaaa ttgaagatct gacccgcgag gcgatgggct tttctgaaaa acgcggtgac   1260
tcgctcaatg tcgttaactc gccgttcaat agcagtgacg aaagcggcgg agaactgcca   1320
ttctggcaac agcaagcgtt tatcgatcag ttacttgctg ccggtcgctg gttgctggta   1380
ctgctggtgg cgtggctgct gtggcggaaa gcggtacgtc cgcagctaac acgtcgcgct   1440
gaggcgatga agctgtaca gcaacaggcg caggcccgcg aggaagtgga agatgcggtg   1500
gaagtccgcc tgagcaaaga cgaacaacta caacaacggc gcgctaacca acgtctgggg   1560
gcagaagtca tgagccagcg tatccgtgaa atgtctgata cgatccgcg cgtggtggcg   1620
ctggtcattc gccagtggat aaataacgat catgagtaa                          1659

<210> SEQ ID NO 88
<211> LENGTH: 996
<212> TYPE: DNA
<213> ORGANISM: Escherichia coli

<400> SEQUENCE: 88
atgagtaacc tgacaggcac cgataaaagc gtcatcctgc tgatgaccat tggcgaagac     60
cgggcggcag aggtgttcaa gcacctctcc cagcgtgaag tacaaaccct gagcgctgca    120
atggcgaact tcacgcagat ctccaacaag cagctaaccg atgtgctggc ggagtttgag    180
caagaagctg aacagtttgc cgcactgaat atcaacgcca acgattatct cgcctcggta    240
ttggtcaaag ctctgggtga agaacgtgcc gccagcctgc tggaagatat tctcgaaact    300
cgcgataccg ccagcggtat tgaaacgctc aactttatgg agccacagag cgccgccgat    360
ctgattcgcg atgagcatcc gcaaattatc gccaccattc tggtgcatct gaagcgcgcc    420
caagccgccg atattctggc gttgttcgat gaacgtctgc gccacgacgt gatgttgcgt    480
atcgccacct ttggcggcgt gcagccagcc gcgctggcgg agctgaccga agtactgaat    540
ggcttgctcg acggtcagaa tctcaagcgc agcaaaatgg gcggcgtgag aacggcagcc    600
gaaattatca acctgatgaa aactcagcag gaagaagccg ttattaccgc cgtgcgtgaa    660
ttcgacggcg agctggcgca gaaaatcatc gacgagatgt tcctgttcga gaatctggtg    720
gatgtcgacg atcgcagcat tcagcgtctg ttgcaggaag tggattccga atcgctgttg    780
atcgcgctga aaggagccga gcagccactg cgcgagaaat tcttgcgcaa tatgtcgcag    840
cgtgccgccg atattctgcg cgacgatctc gccaaccgtg gtccggtgcg tctgtcgcag    900
gtggaaaacg aacagaaagc gattctgctg attgtgcgcc gccttgccga aactggcgag    960
atggtaattg gcagcggcga ggataccat gtctga                              996

<210> SEQ ID NO 89
<211> LENGTH: 687
<212> TYPE: DNA
<213> ORGANISM: Escherichia coli

<400> SEQUENCE: 89
atgtctgata atctgccgtg gaaaacctgg acgccggacg atctcgcgcc accacaggca     60
```

```
gagtttgtgc ccatagtcga gccggaagaa accatcattg aagaggctga acccagcctt    120
gagcagcaac tggcgcaact gcaaatgcag gcccatgagc aaggttatca ggcgggtatt    180
gccgaaggtc gccagcaagg tcataagcag ggctatcagg aaggactggc ccaggggctg    240
gagcaaggtc tggcagaggc gaagtctcaa caagcgccaa ttcatgcccg gatgcagcaa    300
ctggtcagcg aatttcaaac tacccttgat gcacttgata gtgtgatagc gtcgcgcctg    360
atgcagatgg cgctggaggc ggcacgtcag gtcatcggtc agacgccaac ggtggataac    420
tcggcactga tcaaacagat ccaacagttg ttgcagcaag aaccgttatt cagcggtaaa    480
ccacagctgc gcgtgcaccc ggatgatctg caacgtgtgg atgatatgct cggcgctacc    540
ttaagtttgc atggctggcg cttgcggggc gatcccaccc tccatcctgg cggctgtaaa    600
gtctccgccg atgaaggcga tctcgacgcc agtgtcgcca ctcgctggca agaactctgc    660
cgtctggcag caccaggagt ggtgtaa                                         687
```

<210> SEQ ID NO 90
<211> LENGTH: 1374
<212> TYPE: DNA
<213> ORGANISM: Escherichia coli

<400> SEQUENCE: 90

```
atgaccacgc gcctgactcg ctggctaacc acgctggata actttgaagc caaaatggcg     60
cagttgcctg cggtacgtcg ctacgggcga ttaacccgcg ctaccgggct ggtgctggaa    120
gccaccggat tacaattgcc gctcggcgca acctgtgtca ttgagcgcca gaacggcagc    180
gaaacgcacg aagtagaaag cgaagtcgtt ggctttaacg gtcaacggct gttttttaatg    240 ccgctggagg aagtcgaagg tgtcctgccc ggcgcgcgtg tttatgccaa aaacatttcg    300
gcagaagggc tgcaaagcgg caagcagttg ccgctcggtc cggcgttatt aggtcgcgtt    360
ctggacggca gcggtaaacc gctcgatggc ctgccctccc ccgatacgac ggaaaaccggt    420 gcgctgatta ccccgccatt taacccgttg caacgtacac cgattgaaca tgtgctggac    480
accggcgtgc gcccaatcaa tgccctgctt accgttgggc gtgggcagcg tatgggcctg    540
tttgccgggt ccggcgttgg taaaagtgtg ctgctgggga tgatggcacg ttacacccgc    600
gccgatgtca ttgtcgtggg tttgattggt gaacgtgggc gcgaagtaaa agattttatt    660
gagaacatcc tcggtgccga agggcgtgca cgctcagtgg tgattgccgc tccggcggat    720
gtttctccgc tcctgcgaat gcagggtgcc gcctatgcca cgcgcattgc gaagattttt    780
cgcgatcgtg gtcagcatgt gttgctgatt atggactccc tcacccgcta cgcgatggcc    840
cagcgtgaaa ttcgctggc gattggcgaa ccccccgcca ccaaaggtta tccaccgtcg    900
gtgtttgcca aattaccggc actggtcgag cgtgccggaa atggcattag cggcggcggc    960
tcgattaccg cgttttatac cgtgctcact gaaggcgatg accagcagga tccgattgcc   1020
gactccgcgc gggcgatcct cgacggtcac attgtgctgt ctcgccgact ggcggaagcc   1080
gggcactatc cggctatcga tattgaagcg tcgatcagcc gcgcaatgac ggcgttgatc   1140
agtgagcaac attacgcgcg agtgcgcacc ttcaaacagc tgttgtcgag ttttcagcgt   1200
aaccgcgatc tggttagcgt cggcgcgtat gccaaaggca gcgatccgat gctcgataaa   1260
gccatcgccc tgtggccgca gctggagggc tatttgcaac aaggcatttt tgaacgcgcg   1320
gactgggaag cgtctctcca ggggctggag cgtatttccc gacagtgtc ataa          1374
```

<210> SEQ ID NO 91

<211> LENGTH: 444
<212> TYPE: DNA
<213> ORGANISM: Escherichia coli

<400> SEQUENCE: 91

```
atggcagaac atggtgcgct ggcgaccctg aaagatctgg cagaaaaaga ggtagaggat      60
gccgcgcgcc tgctgggtga atgcgtcgc ggatgtcagc aggcggaaga acagctcaaa     120
atgctgattg attatcagaa tgaatatcgc aataacctca acagcgatat gagtgccggg     180
ataaccagca accgctggat caactatcag cagtttatcc agacgctgga aaaagccatt     240
actcagcatc gccagcaact taatcagtgg acgcagaaag ttgacattgc cctgaacagt     300
tggcgagaaa aaaacaacg tttgcaggcc tggcagacac tgcaggaacg gcaatccacg      360
gcggcactgc ttgcagaaaa ccgcctcgat cagaaaaaga tggatgagtt cgcccagcgc     420
gccgccatga ggaaacctga atga                                            444
```

<210> SEQ ID NO 92
<211> LENGTH: 1128
<212> TYPE: DNA
<213> ORGANISM: Escherichia coli

<400> SEQUENCE: 92

```
atgattcgct tagcgccctt gattaccgcc gacgttgaca ccaccacatt gcctggcggc      60
aaagccagcg atgctgcaca agattttctc gcgttgttga gcgaagcatt agcaggcgag     120
acaactaccg acaaagcggc ccccagttg ctggtggcaa cagataagcc cacgacaaaa      180
ggcgagccgc tgatcagcga tattgtttcc gacgcgcaac aagctaattt actgatccct     240
gtggatgaaa caccgcctgt catcaacgac gaacaatcca catcaacacc gttaaccacc     300
gctcagcgta tggcgttggc tgcggtggct gacaaaaata cgacaaaaga cgaaaaagcg     360
gatgatctga atgaagacgt caccgcaagc ctgagcgccc tttttgcgat gttgccgggt     420
tttgacaata cgcccaaagt gactgatgcg ccgtcaaccg tgttaccgac agagaaacca     480
acgctcttca caaaactgac ttctgagcaa ctcacaacag cacagcctga tgacgccccc     540
ggcacaccag ctcagccatt aacaccgctg gtagcagaag cccagagtaa agcggaagtc     600
atcagcacac cttaccggt gaccgctgcc gccagcccgc taatcactcc acaccagaca      660
cagccactgc ccaccgtcgc cgcacctgtt ttgagtgcac cgctgggttc tcacgaatgg     720
caacaatcat taagccagca tatttcgctg ttcacccgcc aggggcaaca aagtgcagag     780
ttgcgtctgc acccgcagga tttaggtgaa gtgcaaatct ccctcaaagt ggatgataac     840
caggcgcaaa tccagatggt ttcaccgcat cagcatgtac gcgccgccct ggaagcagcg     900
ctgccggtac tgcgcacgca gctggccgaa agtggcattc agttagggca aagcaacatc     960
agtggcgaaa gctttagtgg tcagcagcag gccgcttccc agcaacagca aagccaacgc    1020
acagcaaacc atgaacctct ggcggggaa gacgacgata cgcttccggt tcccgtctct     1080
ttacaagggc gtgtaacagg caacagcggc gttgatattt cgcctaa                  1128
```

<210> SEQ ID NO 93
<211> LENGTH: 10979
<212> TYPE: DNA
<213> ORGANISM: Escherichia coli

<400> SEQUENCE: 93

```
ctacacctgc atgctcatca cttcctgata cgccgccacc agcttattac gcacctgaat      60
ccccatttgc atagaaactg aggctttttg catatcggtc atcacatcgt ttaacgccac     120
```

```
gccgggttca ccgagagtga attttttctgc ctgcgtgcgg gcagctgttt gtgtatcact    180
aatgcgatcg agcgcggcgt gcagctgccc ggcaaaacta atggtcggtt gcggcagtga    240
ttcctgcgca cgcgcactca tcgccgtagc ctgtaactgg ctgataaccc cttcaatccc    300
ctgtatcgct gacattctcg tctcccggat aatttctggt agcaaagcct accagtaagt    360
caataagaca aaggcgctaa atagcaacaa aaaaacgggt ttattggcgg atagaaaaaa    420
acgaaagcac aaataatggg agcgtcaatt tttcgagttt gctgacccgg gagtgagtct    480
tgttccactt tgccaataac gccgtccata atcagccacg aggtgcgcga tgaatgcgac    540
tgcagcccag acaaaatctc ttgagtggct taatcgcctg cgtgcgaatc cgaaaattcc    600
attgattgtt gccggttccg cggcagtggc ggtcatggtc gcactgatcc tgtgggcgaa    660
agcccccgac taccgcacat tattcagcaa tctttccgat caggatggtg gcgcaattgt    720
cagccaactg acgcaaatga atattcctta ccgcttcagc gaagccagcg gcgctattga    780
agttccggca gataaagttc acgaactgcg tctgcgcctg gcacaacaag gtttgccaaa    840
aggcggcgcg gtcggtttcg aactgcttga tcaggaaaag tttggtatca gccagttcag    900
cgaacaggtg aattatcagc gggcgctgga aggcgagctt tctcgtacca tcgaaactat    960
cggcccggta aaggggcgc gcgtacatct ggcaatgccg aaaccgtctt tattcgtccg   1020
tgaacaaaaa tcccttctg catcggtgac ggtaaatctg ttaccggcc gcgcactcga   1080 tgaagggcaa attagcgcca ttgtgcatct ggtttccagc gccgttgctg gtctgccgcc   1140
gggaaacgtc acgctggtgg atcagggcgg acatctgtta acccagtcca ataccagcgg   1200
gcgcgatctt aatgacgctc agttgaaata tgccagcgat gtcgaaggcc gtattcagcg   1260
gcgtattgaa gcgatcctgt cgcctattgt tggtaacggt aatattcacg cccaggttac   1320
ggcgcagctg gacttcgcca gtaaagaaca aacggaagaa cagtatcgcc ctaacggtga   1380
tgaatctcat gcggcgcttc gttcacgcca gcttaatgag agcgagcaaa gcggttccgg   1440
ttatccgggc ggcgtaccgg gggcgttgtc gaatcaaccg gcacctgcga ataacgcgcc   1500
aatcagcacg cctccggcaa atcaaaataa ccgccagcag caggcgagca ccaccagcaa   1560
tagtgggccg cgtagcacac agcggaatga accagtaacc tacgaagtcg atcgcaccat   1620
tcgtcatacc aaaatgaacg tgggcgatgt gcaacgtctg tcagtcgcgg tcgtggtgaa   1680
ttacaaaacc ttgccagatg gcaaaccgtt gcctctcagc aacgaacaga tgaagcaaat   1740
tgaagatctg acccgcgagg cgatgggctt ttctgaaaaa cgcggtgact cgctcaatgt   1800
cgttaactcg ccgttcaata gcagtgacga aagcggcgga gaactgccat tctggcaaca   1860
gcaagcgttt atcgatcagt tacttgctgc cggtcgctgg ttgctggtac tgctggtggc   1920
gtggctgctg tggcggaaag cggtacgtcc gcagctaaca cgtcgcgctg aggcgatgaa   1980
agctgtacag caacaggcgc aggcccgcga ggaagtggaa gatgcggtgg aagtccgcct   2040
gagcaaagac gaacaactac aacaacggcg cgctaaccaa cgtctggggg cagaagtcat   2100
gagccagcgt atccgtgaaa tgtctgataa cgatccgcgc gtggtggcgc tggtcattcg   2160
ccagtggata aataacgatc atgagtaacc tgacaggcac cgataaaagc gtcatcctgc   2220
tgatgaccat tggcgaagac cgggcggcag aggtgttcaa gcacctctcc cagcgtgaag   2280 tacaaacccct gagcgctgca atggcgaacg tcacgcagat ctccaacaag cagctaaccg   2340
atgtgctggc ggagtttgag caagaagctg aacagtttgc cgcactgaat atcaacgcca   2400
acgattatct gcgctcggta ttggtcaaag ctctgggtga agaacgtgcc gccagcctgc   2460
```

```
tggaagatat tctcgaaact cgcgataccg ccagcggtat tgaaacgctc aactttatgg    2520
agccacagag cgccgccgat ctgattcgcg atgagcatcc gcaaattatc gccaccattc    2580
tggtgcatct gaagcgcgcc caagccgccg atattctggc gttgttcgat gaacgtctgc    2640
gccacgacgt gatgttgcgt atcgccacct tggcggcgt gcagccagcc gcgctggcgg    2700
agctgaccga agtactgaat ggcttgctcg acggtcagaa tctcaagcgc agcaaaatgg    2760
gcggcgtgag aacggcagcc gaaattatca acctgatgaa aactcagcag gaagaagccg    2820
ttattaccgc cgtgcgtgaa ttcgacggcg agctggcgca gaaaatcatc gacgagatgt    2880
tcctgttcga gaatctggtg gatgtcgacg atcgcagcat tcagcgtctg ttgcaggaag    2940
tggattccga atcgctgttg atcgcgctga aaggagccga gcagccactg cgcgagaaat    3000
tcttgcgcaa tatgtcgcag cgtgccgccg atattctgcg cgacgatctc gccaaccgtg    3060
gtccggtgcg tctgtcgcag gtggaaaacg aacagaaagc gattctgctg attgtgcgcc    3120
gccttgccga aactggcgag atggtaattg gcagcggcga ggatacctat gtctgataat    3180
ctgccgtgga aaacctggac gccggacgat ctcgcgccac cacaggcaga gtttgtgccc    3240
atagtcgagc cggaagaaac catcattgaa gaggctgaac ccagccttga gcagcaactg    3300
gcgcaactgc aaatgcaggc ccatgagcaa ggttatcagg cgggtattgc cgaaggtcgc    3360
cagcaaggtc ataagcaggg ctatcaggaa ggactggccc aggggctgga gcaaggtctg    3420
gcagaggcga agtctcaaca agcgccaatt catgcccgga tgcagcaact ggtcagcgaa    3480
tttcaaacta cccttgatgc acttgatagt gtgatagcgt cgcgcctgat gcagatggcg    3540
ctggaggcgg cacgtcaggt catcggtcag acgccaacgg tggataactc ggcactgatc    3600
aaacagatcc aacagttgtt gcagcaagaa ccgttattca gcggtaaacc acagctgcgc    3660
gtgcacccgg atgatctgca acgtgtggat gatatgctcg cgctaccttt aagtttgcat    3720
ggctggcgct tgcggggcga tcccacccctc catcctggcg gctgtaaagt ctccgccgat    3780
gaaggcgatc tcgacgccag tgtcgccact cgctggcaag aactctgccg tctggcagca    3840
ccaggagtgg tgtaatgacc acgcgcctga ctcgctggct aaccacgctg gataactttg    3900
aagccaaaat ggcgcagttg cctgcggtac gtcgctacgg gcgattaacc cgcgctaccg    3960
ggctggtgct ggaagccacc ggattacaat tgccgctcgg cgcaacctgt gtcattgagc    4020
gccagaacgg cagcgaaacg cacgaagtag aaagcgaagt cgttggcttt aacggtcaac    4080
ggctgttttt aatgccgctg gaggaagtcg aaggtgtcct gcccggcgcg cgtgtttatg    4140
ccaaaaacat ttcggcagaa gggctgcaaa gcggcaagca gttgccgctc ggtccggcgt    4200
tattaggtcg cgttctggac ggcagcggta aaccgctcga tggcctgccc tccccgata    4260 cgacggaaac cggtgcgctg attacccgc catttaaccc gttgcaacgt acaccgattg    4320
aacatgtgct ggacaccggc gtgcgcccaa tcaatgccct gcttaccgtt gggcgtgggc    4380
agcgtatggg gctgttttgcc gggtccggcg ttggtaaaag tgtgctgctg gggatgatgg    4440
cacgttacac ccgcgccgat gtcattgtcg tgggtttgat tggtgaacgt gggcgcgaag    4500
taaaagattt tattgagaac atcctcggtg ccgaagggcg tgcacgctca gtggtgattg    4560
ccgctccggc ggatgttttct ccgctcctgc gaatgcaggg tgccgccttat gccacgcgca    4620 ttgccgaaga ttttcgcgat cgtggtcagc atgtgttgct gattatggac tccctcaccc    4680
gctacgcgat ggcccagcgt gaaattgcgc tggcgattgg cgaacccccc gccaccaaag    4740
gttatccacc gtcggtgttt gccaaattac cggcactggt cgagcgtgcc ggaaatggca    4800
ttagcggcgg cggctcgatt accgcgtttt ataccgtgct cactgaaggc gatgaccagc    4860
```

```
aggatccgat tgccgactcc gcgcgggcga tcctcgacgg tcacattgtg ctgtctcgcc    4920
gactggcgga agccgggcac tatccggcta tcgatattga agcgtcgatc agccgcgcaa    4980
tgacggcgtt gatcagtgag caacattacg cgcgagtgcg caccttcaaa cagctgttgt    5040
cgagttttca gcgtaaccgc gatctggtta gcgtcggcgc gtatgccaaa ggcagcgatc    5100
cgatgctcga taaagccatc gccctgtggc cgcagctgga gggctatttg caacaaggca    5160
tttttgaacg cgcggactgg gaagcgtctc tccaggggct ggagcgtatt ttcccgacag    5220
tgtcataacc caggagataa cggcagatgg cagaacatgg tgcgctggcg accctgaaag    5280
atctggcaga aaaagaggta gaggatgccg cgcgcctgct gggtgaaatg cgtcgcggat    5340
gtcagcaggc ggaagaacag ctcaaaatgc tgattgatta tcagaatgaa tatcgcaata    5400
acctcaacag cgatatgagt gccgggataa ccagcaaccg ctggatcaac tatcagcagt    5460
ttatccagac gctggaaaaa gccattactc agcatcgcca gcaacttaat cagtggacgc    5520
agaaagttga cattgccctg aacagttggc gagaaaaaaa acaacgtttg caggcctggc    5580
agacactgca ggaacggcaa tccacggcgg cactgcttgc agaaaaccgc ctcgatcaga    5640
aaaagatgga tgagttcgcc cagcgcgccg ccatgaggaa acctgaatga ttcgcttagc    5700
gcccttgatt accgccgacg ttgacaccac cacattgcct ggcggcaaag ccagcgatgc    5760
tgcacaagat tttctcgcgt tgttgagcga agcattagca ggcgagacaa ctaccgacaa    5820
agcggccccc cagttgctgg tggcaacaga taagcccacg acaaaaggcg agccgctgat    5880
cagcgatatt gtttccgacg cgcaacaagc taatttactg atccctgtgg atgaaacacc    5940
gcctgtcatc aacgacgaac aatccacatc aacaccgtta accaccgctc agacgatggc    6000
gttggctgcg gtggctgaca aaaatacgac aaaagacgaa aaagcggatg atctgaatga    6060
agacgtcacc gcaagcctga gcgccctttt tgcgatgttg ccgggttttg acaatacgcc    6120
caaagtgact gatgcgccgt caaccgtgtt accgacagag aaaccaacgc tcttcacaaa    6180
actgacttct gagcaactca caacagcaca gcctgatgac gccccggca caccagctca    6240 gccattaaca ccgctggtag cagaagccca gagtaaagcg gaagtcatca gcacaccttc    6300
accggtgacc gctgccgcca gcccgctaat cactccacac cagacacagc cactgcccac    6360
cgtcgccgca cctgttttga gtgcaccgct gggttctcac gaatggcaac aatcattaag    6420
ccagcatatt tcgctgttca cccgccaggg gcaacaaagt gcagagttgc gtctgcaccc    6480
gcaggattta ggtgaagtgc aaatctccct caaagtggat gataaccagg cgcaaatcca    6540
gatggtttca ccgcatcagc atgtacgcgc cgccctggaa gcagcgctgc cggtactgcg    6600
cacgcagctg gccgaaagtg gcattcagtt agggcaaagc aacatcagtg gcgaaagctt    6660
tagtggtcag cagcaggccg cttcccagca acagcaaagc caacgcacag caaaccatga    6720
acctctggcg ggggaagacg acgatacgct tccggttccc gtctctttac aagggcgtgt    6780
aacaggcaac agcggcgttg atattttcgc ctaacgtcag aggtagcacc gtaatccgcg    6840
tcttttcccc gctttgttgc gctcaagacg caggataatt agccgataag cagtagcgac    6900
acaggaagac cgcaacacat gactgattac gcgataagca agaaaagcaa gcgatcgctt    6960
tggatcccga ttctggtatt cattaccctc gcggcctgtg ccagcgcagg ttacagctac    7020
tggcattcgc atcaggttgc cgctgacgac aaagcgcagc aacgcgtcgt gccctcaccg    7080
gtcttctacg cgctggatac cttcacggtc aatttgggcg atgcggatcg cgtactttat    7140
atcggcataa ccctgcgcct gaaagatgaa gctacccgct cgcggctgag tgagtatttg    7200
```

```
ccggaagtcc gtagtcgctt gctgttactg ttttcgcgtc aggatgctgc cgtactggcg    7260
acagaagaag gcaagaaaaa cctgattgcc gagattaaaa ccacactttc caccccgctt    7320
gttgccgggc aaccgaaaca ggatgtcacc gacgtgctgt ataccgcttt tattctgcga    7380
taacgacatg ggcgatagta ttctttctca agctgaaatt gatgcgctgt tgaatggtga    7440
cagcgaagtc aaagacgaac cgacagccag tgttagcggc gaaagtgaca ttcgtccgta    7500
cgatccgaat acccaacgac gggttgtgcg cgaacgtttg caggcgctgg aaatcattaa    7560
tgagcgcttt gcccgccatt ttcgtatggg gctgttcaac ctgctgcgtc gtagcccgga    7620
tataaccgtc ggggccatcc gcattcagcc gtaccatgaa tttgcccgca acctgccggt    7680
gccgaccaac ctgaacctta tccatctgaa accgctgcgc ggcactgggc tggtggtgtt    7740
ctcaccgagt ctggtgttta cgccgtggga taacctgttt ggcggcgatg gacgcttccc    7800
gaccaaagtg gaaggtcgcg agtttaccca taccgaacag cgcgtcatca accgcatgtt    7860
gaaactggcg cttgaaggct atagcgacgc ctggaaggcg attaatccgc tggaagttga    7920
gtacgtgcgt tcggaaatgc aggtgaaatt taccaatatc accacctcgc cgaacgacat    7980
tgtggttaac acgccgttcc atgtggagat tggcaacctg accggcgaat ttaatatctg    8040
cctgccattc agcatgatcg agccgctacg ggaattgttg gttaacccgc cgctggaaaa    8100
ctcgcgtaat gaagatcaga actggcgcga taacctggtg cgccaggtgc agcattcaca    8160
gctggagctg gtcgccaact ttgccgatat ctcgctacgc ctgtcgcaga ttttaaaact    8220
gaaccccggc gacgtcctgc cgatagaaaa acccgatcgc atcatcgccc atgttgacgg    8280
cgtcccggtg ctgaccagtc agtatggcac cctcaacggt cagtatgcgt tacgcgataga    8340 acatttgatt aacccgattt taaattctct gaacgaggaa cagcccaaat gagtgacatg    8400
aataatccgg ccgatgacaa caacggcgca atggacgatc tgtgggctga agcgttgagc    8460
gaacaaaaat caaccagcag caaaagcgct gccgagacgg tgttccagca atttggcggt    8520
ggtgatgtca gcgaacgtt gcaggatatc gacctgatta tggatattcc ggtcaagctg    8580
accgtcgagc tgggccgtac gcggatgacc atcaaagagc tgttgcgtct gacgcaaggg    8640
tccgtcgtgg cgctggacgg tctggcgggc gaaccactgg atattctgat caacggttat    8700
ttaatcgccc agggcgaagt ggtggtcgtt gccgataaat atggcgtgcg gatcaccgat    8760
atcattactc cgtctgagcg aatgcgccgc ctgagccgtt agtgatgaat aaccacgcta    8820
ctgtgcaatc ttccgcgccg gtttctgctg cgccactgct gcaggtgagc ggcgcactca    8880
tcgccattat tgccctgatc ctcgctctg cctggctggt aaaacggttg ggatttgccc    8940
ctaaacgcac tggcgttaac ggtctgaaaa ttagcgccag tgcttcactg ggcgcgcgtg    9000
aaagggttgt ggtggtcgat gtggaagatg cacggctggt gctcggcgtt accgcaggtc    9060
aaatcaatct gctgcataaa cttccccctt ctgcaccaac ggaagagata ccgcagaccg    9120
attttcagtc ggtcatgaaa aatttgctta agcgtagcgg gagatcctga tgcgtcgttt    9180
attgtctgtc gcacctgtcc ttctctggct gattacgccc ctcgccttcg cgcaactgcc    9240
gggtatcacc agccagccgc tgcctggcgg tggacaaagc tggtcgctcc cggtgcagac    9300
gctggtgttc atcacctcgt tgacgtttat tccggcaatt ttactgatga tgaccagttt    9360
cacccgcatc atcattgttt ttggtttatt gcgtaacgcg ctgggaacac cctccgcgcc    9420
acctaaccag gtattgctgg ggctggcact gttttttgacc tttttttatta tgtcaccggt    9480 gatcgacaaa atttatgtag atgcgtacca gccattcagc gaagagaaaa tatcaatgca    9540
ggaggcgctg gaaaaagggg cgcagccgct gcgtgagttt atgctgcgtc agacccgtga    9600
```

```
ggcagattta gggttgtttg ccagactggc gaataccggc ccgttgcagg gacctgaagc    9660
cgtgccgatg cgcattttgc tcccggccta cgtgaccagc gagttgaaaa ccgcatttca    9720
gataggcttc acgattttca tcccttttt gattatcgac ctggtgatag ccagcgtgtt    9780
gatggcattg gggatgatga tggttccccc agccaccatt gctctgccct ttaaactgat    9840
gctgtttgta ctggtggatg gctggcaatt gctggtcggt tcgctggcgc agagcttta    9900 cagctagaga ggcaaaatga cacctgaatc ggtcatgatg atggggactg aagcgatgaa    9960
agtcgcgctg gcactggctg ccccgctatt gttggtagcg ttggtcacgg gccttatcat    10020
cagtattttg caggccgcca cgcagattaa cgaaatgacg ctgtcgttta ttccgaaaat    10080
catcgccgta tttatcgcca ttattattgc cggaccgtgg atgctcaatc tgttgctgga    10140
ttacgtccgc accttgttca ctaacctgcc gtatatcatc gggtagccgt actatgttgc    10200
aggtgacaag cgaacaatgg ctatcctggt taaacctgta cttctggccg ttactgcgcg    10260
tgctggcgct gatctccacc gcgccgattc tgagcgaacg cagcgtaccg aaacgggtaa    10320
aactgggtct ggcaatgatg atcacgttcg ccattgcccc atcattacct gccaacgatg    10380
ttcctgtttt ttcgttcttt gctctgtggc tggccgtgca gcagatcctg atcggcattg    10440
cgcttggttt taccatgcaa tttgcctttg ccgctgtgcg aaccgctggc gaaattatcg    10500
gtctgcaaat ggggctgtca tttgcgacgt ttgtcgatcc ggccagccat cttaatatgc    10560
ccgttttagc gcgtatcatg gatatgctgg cgttactgct gttcctgaca tttaacggtc    10620
atttatggtt gatttcactg ctggtcgata cctttcacac cctgccgatt ggtggcgaac    10680
cgttgaacag caatgcgttt ctggcactca ccaaagcagg gagtttgatt ttccttaacg    10740
ggctgatgct ggcgttaccg ctcattactc tgctgctgac actgaatctg gcattaggtt    10800
tacttaatcg tatggcccg caattatcca tttttgttat tggatttcca ttaactctga    10860
ctgtcggcat ctctttaatg gcggcattaa tgccgttaat tgcacctttt tgcgaacatt    10920
tattcagtga aatttttaat ttgctggctg atattattag tgaattgcca ttaatataa    10979
```

METHOD FOR PRODUCING ISOPRENE USING TRANSFORMED E. COLI

PRIORITY

This application claims benefit under 35 U.S.C. 119(e), 120, 121, or 365(c), and is a National Stage entry from International Application No. PCT/KR2017/000990, filed Jan. 26, 2017, which claims priority to the benefit of Korean Patent Application No. 10-2016-0009568 filed on Jan. 26, 2016 and 10-2017-0012696 filed on Jan. 26, 2017 in the Korean Intellectual Property Office, the entire contents of which are incorporated herein by reference.

TECHNICAL FIELD

The present invention relates to a method for producing isoprene.

BACKGROUND ART

Isoprene is one of major components for natural rubber, and is also a fundamental chemical compound for production of synthetic rubber. Isoprene is mostly used for manufacturing tires, medical supplies, adhesives, and the like. Isoprene is generally produced in a petroleum refining process. In recent years, due to a price change of petroleum, a refining process focusing on production of a fuel material free of isoprene and increased demand for the synthetic rubber, a price of the isoprene is steadily on an upward tendency. Further, isoprene can be used as a cargo fuel and/or a jet fuel, and has features such as higher energy efficiency and lower emission of greenhouse fuel than other bio-fuels. Therefore, isoprene may be suitably used as a drop-in biofuel.

Production of isoprene using microorganisms results in very high purity with no need for a high refining process. Further, there is advantages that isoprene is possibly produced using renewable resources and low cost materials, and can be easily changed into bio-fuels and bio-chemicals.

In biological aspects, isoprene may be produced from an isoprene synthase with a precursor, for example, DMAPP prepared in a mevalonate (MVA) pathway and a MEP pathway (see FIG. 1). Since production and release of isoprene using poplar and willow species were initially reported then till now, studies on a mechanism of discharging isoprene from plants and related enzymes have been steadily done. However, studies on a production of isoprene based on microorganisms and using microorganisms as a host is being performed only recently.

Currently, global tire manufacturers and fermentation companies are jointed and pursue an investigation in regard to a method for mass-production of isoprene from different materials other than petroleum. Representative companies among those are Du Pont and Goodyear Tire & Rubber Company. Du Pont and Goodyear first signed onto the collaboration in 2008, and have conducted the research and development for mass-production of isoprene from microorganisms. In particular, these companies tried to isolate isoprene synthases from a variety of poplar and willow species, then compare efficiencies of such isoprene synthases with one another. Further, they combined different metabolic pathways for providing precursors and conducted experiments thereof. It is now reported that about 80% of industrialization has been carried out. However, although isoprene productivity is relatively high, a great amount of carbon source is consumed to produce isoprene, thus to cause a drawback of low production efficiency.

Qingdao University of Science and Technology in China has accelerated the research on isoprene production using microorganisms since 2012. In particular, as a result of combining MVA pathways of *Populus alba* isoprene synthase and yeast (*Saccharomyces cerevisiae*), the maximum production of 6.3 g/L was accomplished by the university. Herein, this is a method of producing isoprene from an *Escherichia coli* host by introducing a combination of simple isoprene synthase and a precursor pathway. However, in order to increase isoprene production, this method lacks consideration of metabolic engineering in regard to a host microorganism-inherent metabolic pathway, which influences upon the isoprene production, thus having a drawback of lower isoprene productivity than a carbon source added to a medium.

In regard to other isoprene production, although collaborated researches between diverse bioengineering companies and petrochemical companies have been under way, specific research findings have yet to be reported.

According to prior art described above, isoprene has been produced from microorganism hosts by a method of combining isoprene synthases and mevalonate pathways as a bio-synthetic pathway of a precursor, and then simply optimizing these pathways using a metabolic engineering method. Such a technical concept as described above does not consider overall metabolic pathway efficiency of host microorganisms, thus entailing an increase in production costs due to a lower production yield of isoprene than a carbon source substrate introduced therein.

Accordingly, in consideration of great importance of substrate costs in production of bio-fuels and bio-chemicals through microorganism fermentation, other than optimization of the isoprene synthase and a biosynthetic pathway of a precursor, there is still a need for improvement of isoprene productivity through engineering a host microorganism-inherent metabolic pathway, which influences upon the isoprene productivity.

SUMMARY

It is an object of the present invention to provide a method for producing isoprene by engineering an *Escherichia coli*-inherent metabolic pathway, thereby maximizing isoprene productivity.

According to one embodiment of the present invention, there is provided a method for producing isoprene, including: culturing *E. coli*, which has isoprene productivity and in which a gene encoding a recombinase A (recA) protein is attenuated or deleted, in a medium (or culture solution) including a carbon source.

*E. coli* strains such as DH5a, MG1655, BL21 (DE), S17-1, XL1-Blue, BW25113, etc. are industrially much used for enzyme production through biotransformation. Among those, in an aspect of productivity, DH5a is mostly used. Meanwhile, DH5a strain is a strain with deletion of thiamine biosynthetic gene and thus cannot produce thiamine by itself. For this reason, when using DH5a, thiamine should be added to the medium, thus bearing burden of expenses.

Meanwhile, MG1655 has a high growth rate, whereas entails a drawback of low production rate of isoprene materials. The present inventors have studied what types of factors cause a difference in production rates of isoprene materials between *E. coli* strains, and therefore, found that the isoprene production rate is influenced by recA protein.

RecA protein is a protein having a molecular weight of about 38 kDa, which is needed for recovery of damaged DNA and preservation of the same. This protein is bound with single-stranded DNA containing ATP in the center and thus activated to exhibit ATPase activity. Further, the protein is known to form a hydrogen bond along with complementary chains in the single-strained DNA by partially rewinding double-stranded DNA, thereby inducing DNA combination.

The present inventors found that *E. coli* with deletion of recA protein exhibited a higher isoprene production amount, and therefore, the present invention has been completed on the basis of the finding.

In the present disclosure, the term "attenuation" refers to reduced expression of target gene, as compared to a parental strain. The term "deletion" represents lost expression of the target gene.

The attenuation or deletion may occur by variation of gene sequence, for example, substitution, deletion, insertion or a combination thereof. The attenuation or deletion may occur by variation of gene control sequence, for example, substitution, deletion, insertion or a combination thereof.

The *E. coli* described above may include, for example, DH5a, MG1655, BL21 (DE), S17-1, XL1-Blue, BW25113, or a combination thereof. In aspects of cell growth rate and isoprene productivity, MG1655 is preferably used.

The gene encoding a recA protein may be a gene encoding a recA protein of corresponding *E. coli* strains. This is known by NCBI genbank, and the like. For example, the gene encoding a recA protein of MG1655 strain may have a nucleotide sequence of SEQ ID NO: 76.

The *E. coli* has isoprene productivity. In the present disclosure, *E. coli* having isoprene productivity may refer to a microorganism that intrinsically expresses an enzyme required for isoprene production or introduces a gene encoding the enzyme so as to express the enzyme.

As described above, the recA protein is related to homologous recombination of DNA. According to the present invention, when introducing a gene encoding enzyme required for isoprene production, the gene represents an increased isoprene production amount although it does not have homology to *E. coli* inherent genes, thus not to induce homologous recombination. That is, it is considered that an increase in the isoprene production amount may be achieved according to an alternative pathway rather than inhibition of homologous recombination of DNA. The above results were not observed in other isoprenoids other than isoprene.

Enzymes required for isoprene production may include, for example, isoprene synthase and enzymes related to a mevalonate pathway.

More particularly, the *E. coli* may have, as a gene encoding the isoprene synthase, a gene encoding the isoprene synthase derived from *Populus trichocarpa* of SEQ ID NO: 1 intrinsically or by introduction therein.

The introduction of the gene encoding isoprene synthase may be performed by, for example, transformation of a plasmid with a strengthened ribosomal binding site into *E. coli*.

A ribosomal binding site is a site in which mRNA binds with ribosome at the start of protein biosynthesis, and if the ribosomal binding site is strengthened, an amount of isoprene synthase expression may be increased.

Strengthening the ribosomal binding site may be performed by, for example, improving a translation initiation rate (TIR) value of a ribosomal binding site sequence. More particularly, for example, the gene encoding isoprene synthase may be introduced into a plasmid having a TIR value of 3,000 au or more in a ribosomal binding site sequence corresponding thereto, preferably 5,000 au, more preferably 10,000 au, and further preferably 30,000 au. In such a case, the amount of isoprene synthase expression may be significantly increased. The upper limit is not particularly limited, but may be 100,000 au, for example.

The TIR value may be adjusted by changing a sequence between the ribosomal binding site and a translation initiation point. For example, in a case of the gene encoding isoprene synthase derived from *Populus trichocarpa* of SEQ ID NO: 1, the sequence from the ribosomal binding site to ATG as the translation initiation point may be adjusted by changing the existing AGGAAACAGACC (with TIR value of 217 au) into AGGAGGTAATAAACC (with TIR value of 39, 327 au).

The present inventors used pTrc99SN vector reinforced by changing a ribosomal binding site sequence of pTrc99A vector into AGGAGGTAATAAACC, in order to increase the isoprene synthase derived from *Populus trichocarpa* of SEQ ID NO: 1, but it is not limited thereto. Further, the sequence having a specific translation initiation rate value for a specific gene may be generated using Reverse Engineer RBSs program obtained from https://www.denovodna.com.

FIG. 1 illustrates an isoprene biosynthetic pathway including a mevalonate (MVA) pathway and a MEP pathway. Referring to FIG. 1, enzymes related to the mevalonate pathway include acetoacetyl-CoA synthase/HMG-CoA reductase, HMG-CoA synthase, mevalonate kinase, mevalonate diphosphate carboxylase, phosphomevalonate kinase and isoprenyl pyrophosphate isomerase.

The *E. coli* may express an enzyme related to a mevalonate-based pathway of, for example, *Enterococcus* genus or *Streptococcus* genus or a combination thereof.

In particular, the *E. coli* may include: as a gene encoding an enzyme related to the mevalonate pathway, a gene encoding an enzyme with functions of acetyacetyl-CoA synthase derived from *Enterococcus faecalis* and HMG-CoA reductase, simultaneously (SEQ ID NO: 2); a gene encoding HMG-CoA synthase derived from *Enterococcus faecalis* (SEQ ID NO: 3); a gene encoding mevalonate kinase derived from *Streptococcus pneumoniae* (SEQ ID NO: 4); a gene encoding mevalonate diphosphate carboxylase derived from *Streptococcus pneumoniae* (SEQ ID NO: 5); a gene encoding phosphomevalonate kinase derived from *Streptococcus pneumoniae* (SEQ ID NO: 6); and a gene encoding isoprenyl pyrophosphate isomerase derived from *Escherichia coli* MG 1655 (SEQ ID NO: 7), which are contained intrinsically or by introduction therein.

Further, a gene encoding an enzyme related to the mevalonate pathway may be amplified or introduced through a vector with being amplified. In such a case, expression of the enzyme related to the mevalonate pathway may be increased, thus sufficiently supplying DMAPP required for cell growth. Accordingly, reduction of cell growth may be prevented.

The term "amplification" refers to an increase in gene copy or in expression level of the gene. An aspect of the amplification may be accomplished by increasing the copy number of the introduced foreign genes or intrinsic genes. For the amplification, a promoter or ribosomal binding site (RBS) may be substituted so as to increase the expression level of the gene.

In addition, the *E. coli* may further include, as a gene encoding an enzyme related to a mevalonate pathway, a gene selected from a gene encoding isoprenyl pyrophosphate isomerase derived from *Synechocystis* sp. PCC6803 (SEQ ID NO: 8); a gene encoding isoprenyl pyrophosphate isomerase derived from *Streptococcus pneumoniae* (SEQ ID NO: 9); and a gene encoding isoprenyl pyrophosphate isomerase derived from *Haematococcus plavialis* (SEQ ID NO: 10), which is included intrinsically or by introduction therein. Preferably, the *E. coli* further includes the gene encoding isoprenyl pyrophosphate isomerase derived from *Synechocystis* sp. PCC6803 (SEQ ID NO: 8).

Further, the *E. coli* may include a gene encoding a fusion protein of isoprene synthase and isoprenyl pyrophosphate isomerase, instead of the gene encoding isoprene synthase. In such a case, isoprene productivity may be further improved. The corresponding gene may be obtained by a design of cloning two genes in a vector to express a single protein. An order of genes in the cloning design is not particularly limited, for example, the gene encoding isoprene synthase may be designed to be present before or after a gene encoding isoprenyl pyrophosphate isomerase.

More particularly, instead of the gene encoding isoprene synthase derived from *Populus trichocarpa* (SEQ ID NO: 1), the *E. coli* may include: a gene encoding a fusion protein of isoprene synthase derived from *Populus trichocarpa* (SEQ ID NO: 1) and isoprenyl pyrophosphate isomerase derived from *E. coli*. MG1655 (SEQ ID NO: 7), which is represented by SEQ ID NO: 11 (that is, the gene encoding isoprene synthase is positioned before the gene encoding isoprenyl pyrophosphate isomerase); a gene encoding a fusion protein of isoprenyl pyrophosphate isomerase derived from *E. coli* MG1655 (SEQ ID NO: 7) and isoprene synthase derived from *Populus trichocarpa* (SEQ ID NO: 1), which is represented by SEQ ID NO: 12 (that is, the gene encoding isoprene synthase is positioned after the gene encoding isoprenyl pyrophosphate isomerase); a gene encoding a fusion protein of isoprene synthase derived from *Populus trichocarpa* (SEQ ID NO: 1) and *Synechocystis* isoprenyl pyrophosphate isomerase (SEQ ID NO: 8), which is represented by SEQ ID NO: 13 (that is, the gene encoding isoprene synthase is positioned before the gene encoding isoprenyl pyrophosphate isomerase); or a gene encoding a fusion protein of *Synechocystis* isoprenyl pyrophosphate isomerase (SEQ ID NO: 8) and isoprene synthase derived from *Populus trichocarpa* (SEQ ID NO: 1), which is represented by SEQ ID NO: 14 (that is, the gene encoding isoprene synthase is positioned after the gene encoding isoprenyl pyrophosphate isomerase). Preferably, the *E. coli* includes the gene encoding a fusion protein of isoprenyl pyrophosphate isomerase derived from *E. coli* MG1655 (SEQ ID NO: 7) and isoprene synthase derived from *Populus trichocarpa* (SEQ ID NO: 1), which is represented by SEQ ID NO: 12.

The gene encoding isoprene synthase and an enzyme related to a mevalonate pathway may be introduced into *E. coli*, through each of plasmids or a single plasmid.

When introducing the gene encoding isoprene synthase and the enzyme related to a mevalonate pathway into microorganisms through a single-integrated plasmid, the integrated plasmid may be an ampicillin-resistant gene (bla) (SEQ ID NO: 18) substituted by kanamycin-resistant gene (nptII) (SEQ ID NO: 19). In such a case, the isoprene production amount may be increased by improvement of stability of plasmid.

To improve the isoprene production amount, if necessary, a plasmid including a gene that encodes the enzyme related to the mevalonate pathway during introduction of the integrated plasmid may be further introduced.

Further, the *E. coli* may be one in which a gene encoding an enzyme that generates a fermentation by-product ('fermentation by-product generating enzyme') is attenuated or deleted.

The fermentation by-product during isoprene production may include, for example, acetate, alcohol, lactate, acetoacetate, phosphoenol pyruvate, etc., wherein acetyl-CoA as a precursor of the mevalonate pathway is consumed by the by-product, resulting in a decrease in isoprene production efficiency. The fermentation may be fermentation to generate an organic acid mixture in addition to isoprene production.

However, if the gene encoding a fermentation by-product generating enzyme is attenuated or deleted, undesirable consumption of the precursor, that is, acetyl-CoA may be prevented while maximizing isoprene productivity.

The gene encoding the fermentation by-product generating enzyme may include, for example, dld related to lactate generation, atoD or atoA related to acetoacetate generation, pps related to phosphoenol pyruvate generation, and the like. The *E. coli* may be one in which at least one of the above genes is attenuated or deleted. Preferably, all of the above genes are attenuated or deleted.

The gene described above may have a sequence derived from corresponding *E. coli* strains. More particularly, in a case of MG1655, dld may have a nucleotide sequence of SEQ ID NO: 52, atoD may have a nucleotide sequence of SEQ ID NO: 53, and pps may have a nucleotide sequence of SEQ ID NO: 54.

Further, the gene encoding a fermentation by-product generating enzyme may further include, for example, ackA-pta, poxB, etc. related to acetate generation, adhE, related to alcohol generation, ldhA related to lactate generation. The *E. coli* may be one in which at least one of the above genes is attenuated or deleted. Preferably, all of the above genes are attenuated or deleted.

The above genes may include a sequence derived from corresponding *E. coli* strains. More particular, in a case of MG1655, ackA-pta may have a nucleotide sequence of SEQ ID NO: 48, poxB may have a nucleotide sequence of SEQ ID NO: 49, adhE may have a nucleotide sequence of SEQ ID NO: 50, and ldhA may have a nucleotide sequence of SEQ ID NO: 51.

Further, the *E. coli* may be one in which a gene encoding NudB protein is attenuated or deleted.

NudB protein is an intrinsic (or inherent) enzyme of *E. coli* and catalyzes conversion of IPP and DMAPP as precursors of isoprene into 3-methyl-3-buten-1-ol and 3-methyl-2-buten-1-ol, respectively.

That is, the isoprene precursor is decreased by action of NudB, thus to reduce an isoprene production amount. The present invention may further increase the isoprene production amount by reducing or deleting the gene encoding NudB protein.

The gene encoding NudB protein may have known NudB sequence of *E. coli*. For specific example, MG1655 strain may have a nucleotide of SEQ ID NO: 77, but it is not limited thereto.

Further, the *E. coli* may be one in which flagella are inactivated or removed.

The flagellum is a movement organ of *E. coli*, and the *E. coli* take swimming exercise through the same. The present inventor found that the isoprene production amount could be further increased by inactivating or removing the flagella, and therefore, the present invention has been completed on the bases of the above finding.

A method for inactivating or removing flagellum is not particularly limited so long as the flagellum can be inactivated or removed. For example, the flagellum may be inactivated or removed by attenuating or deleting a gene that promotes formation of flagellum, which is necessary for the formation of flagellum.

More particularly, it is possible to delete or inactivate at least one gene selected from the group consisting of fliF, fliG, fliH, fliI, fliJ and fliK.

For example, fliF may have a nucleotide sequence of SEQ ID NO: 87, fliG may have a nucleotide sequence of SEQ ID NO: 88, fliH may have a nucleotide sequence of SEQ ID NO: 89, fliI may have a nucleotide sequence of SEQ ID NO: 90, fliJ may have a nucleotide sequence of SEQ ID NO: 91, and fliK may have a nucleotide sequence of SEQ ID NO: 92.

Further, other than the sequences described above, an operon including any one of these sequences may be deleted or inactivated.

The operon including any one of the above sequences may have, for example, a nucleotide sequence of SEQ ID NO: 93.

Culture may be conducted on a synthetic, semi-synthetic or complex culture media. The culture medium may be a medium containing a carbon source, a nitrogen source, vitamins and minerals. For example, a terrific medium (TB) liquid medium, and a liquid medium in which a protein expressed material is added may be used.

The carbon source used herein may be selected from the group consisting of starch, glucose, sucrose, galactose, fructose, glycerol and a mixture thereof, and glycerol is preferably used. The nitrogen source used herein may be selected from the group consisting of ammonium sulfate, ammonium nitrate, sodium nitrate, glutamic acid, casamino acid, yeast extract, peptone, tryptone, soybean oil meal and a mixture thereof, and tryptone is preferably used.

The culture may be conducted in typical culture conditions of E. coli. For example, the culture may be conducted at a temperature of about 15-45° C. for example, 15-44° C., 15-43° C., 15-42° C., 15-41° C., 15-40° C., 15-39° C., 15-38° C., 15-37° C., 15-36° C., 15-35° C., 15-34° C., 15-33° C., 15-32° C., 15-31° C., 15-30° C., 20-45° C., 20-44° C., 20-43° C., 20-42° C., 20-41° C., 20-40° C., 20-39° C., 20-38° C., 20-37° C., 20-36° C., 20-35° C., 20-34° C., 20-33° C., 20-32° C., 20-31° C., 20-30° C., 25-45° C., 25-44° C., 25-43° C., 25-42° C., 25-41° C., 25-40° C., 25-39° C., 25-38° C., 25-37° C., 25-36° C., 25-35° C., 25-34° C., 25-33° C., 25-32° C., 25-31° C., 25-30° C., 27-45° C., 27-44° C., 27-43° C., 27-42° C., 27-41° C., 27-40° C., 27-39° C., 27-38° C., 27-37° C., 27-36° C., 27-35° C., 27-34° C., 27-33° C., 27-32° C., 27-31° C. or 27-30° C.

In order to remove the culture medium from the culture solution then recover or remove only the concentrated cells, the culture solution may be subjected to centrifugation or filtration. These steps may be performed as necessary of those skilled in the art. The concentrated cells may undergo freezing or freeze-drying (lyophilization) to preserve without losing its activity.

In one example of the culture, the culture may be conducted in a medium containing glycerol as a carbon source. Glycerol may be the sole carbon source in the medium: more particularly, the culture may be conducted in a medium containing 0.5-5.0% (w/v), for example, 0.5-4.5% (w/v) 0.5-4.0% (w/v), 0.5-3.5% (w/v), 0.5-3.0% (w/v), 0.5-2.5% (w/v), 0.5-2.0% (w/v), 1-5.0% (w/v), 1-4.5% (w/v) 1-4.0% (w/v) 1-3.5% (w/v), 1-3.0% (w/v) or 1-2.5% (w/v) of glycerol. The medium may be a TB medium containing glycerol added thereto. TB medium contains 24 g yeast extract, 12 g tryptone, 9.4 g $K_2HPO_4$, 2.2 $KH_2PO_4$ (pH 7.0) per liter.

According to one embodiment of the present invention, during the culture of E. coli, the medium may include 1 to 3.0% by volume of glycerol, the Escherichia genus microorganism is E. coli MG1655, and the culture may be conducted in 50 ml TB medium at 25 to 35° C., for 24 to 48 hours.

In addition, medium may further include an expression-inducing agent to increase an expression level of protein required for isoprene production in E. coli.

Therefore, the isoprene production amount may be further improved by including the expression-inducing agent.

The expression-inducing agent may be any one known in the art without particular limitation thereof, and includes, for example, isopropyl β-D-1-thiogalactopyranoside (IPTG) or lactose, and preferably, lactose.

The expression-inducing agent may be included in an amount of 1 g/l to 20 g/l, and particularly, 1 g/l to 10 g/l, but it is not limited thereto.

In addition, the medium may further include $Mg^{2+}$.

Therefore, the isoprene production amount may be further improved by including $Mg^{2+}$.

$Mg^{2+}$ may be included in an amount of 5 mM or more, particularly, 10 mM or more, and more particularly, 20 mM or more. The upper limit is not particularly limited but may be for example, about 30 mM. If $Mg^{2+}$ is included in an amount within the above range, isoprene productivity may be maximized.

If necessary, the culture may be conducted in a culture medium in the presence of a lipophilic material, for example, in a state in which a dodecane phase as the lipophilic material is present on a surface of the medium.

The lipophilic material may include, for example, octane, decane, dodecane, tetradecane, pyto-squalane, mineral oil, isopropyl myristate, cetylethyl hexanoate, dioctanoyl decanoyl glycerol, squalane, or a combination thereof.

The lipophilic material may not only stabilize isoprene to be produced, but also improve isoprene productivity by E. coli. The lipophilic material does not affect the growth of E. coli or has little influence.

The culture may be conducted with being stirred. The stirring may be carried out at 100 to 300 rpm, for example, 100 to 280 rpm, 100 to 260 rpm, 1.00 to 240 rpm, 100 to 220 rpm, 100 to 200 rpm, 100 to 180 rpm, 100 to 160 rpm, 100 to 140 rpm, 100 to 120 rpm, 120 to 300 rpm, 120 to 280 rpm, 120 to 260 rpm, 120 to 240 rpm, 120 to 220 rpm, 120 to 200 rpm, 120 to 180 rpm, 120 to 160 rpm, 120 to 140 rpm, 150 to 300 rpm, 150 to 280 rpm, 150 to 260 rpm, 150 to 240 rpm, 150 to 220 rpm, 150 Lo 200 rpm, 150 to 180 ram. 140 to 160 rpm, 200 to 300 rpm, 200 to 280 rpm, 200 to 260 rpm, 200 to 240 rpm, 200 to 220 rpm, or 150 rpm.

When stirring, the lipophilic material such as dodecane is dispersed in a medium to be in contact with the cells. The lipophilic material may be dispersed in the medium to have an increased area in contact with microorganisms, thus to efficiently separate isoprene from cells during culture, and thereby stabilizing and/or dissolving the same.

When culturing the microorganisms in the culture medium in the presence of the lipophilic material, for example, dodecane phase, the produced isoprene may be absorbed in the lipophilic material, that is, dodecane phase before being degraded in the cells, thereby improving the isoprene production amount.

The lipophilic material, that is, dodecane phase does not affect the growth of cells, is hydrophobic for extracting hydrophobic isoprene, and may have low volatility.

A volume ratio of the medium to the lipophilic material is not limited in a specific range. For example, when the volume ratio of the medium to the lipophilic material may range from 1:0.1-3.0, 1:0.2-3.0, 1:0.5-3.0, 1:1.0-3.0, 1:1.5-3.0, 1:2.0-3.0, 1:2.5-3.0, 1:0.2-2.5, 1:0.2-2.0, 1:0.2-1.5, 1:0.2-1.0, 1:0.2-0.5, 1:0.5-2.5, 1:0.5-2.0, 1:0.5-1.5, 1:0.5-1.0, 1:0.8-2.5, 1:0.8-2.0, 1:0.8-1.5, 1:0.8-1.2, 1:0.8-1.0 and the like.

The *E. coli* for isoprene production according to one embodiment of the present invention may have isoprene productivity, wherein a gene encoding a recombinase A (recA) protein is attenuated or deleted.

The *E. coli* may include, for example, DH5a, MG1655, BL21(DE), S17-1, XL1-Blue, BW25113, or a combination thereof. In aspects of cell growth rate and isoprene productivity, MG1655 is preferably used.

The gene encoding a recA protein may be a gene encoding a recA protein of the corresponding *E. coli* strain. This is known in NCBI genbank and the like. For example, a gene encoding a recA protein of MG1655 strain may have a nucleotide sequence of SEQ ID NO: 73.

The above-described *E. coli* may intrinsically express an enzyme required for isoprene production or express the enzyme by introducing a gene encoding the same. These genes may be introduced by the above-described plasmid.

Further, the *E. coli* may be one in which the gene encoding the above-described fermentation by-product generating enzyme is attenuated or deleted.

Further, the *E. coli* may be one in which the gene encoding NudB protein is attenuated or deleted.

Furthermore, the *E. coli* may be one in which flagella are inactivated or removed from the same.

The method for producing isoprene according to the present invention may achieve excellent isoprene productivity. Therefore, a great amount of isoprene may be produced within a short period of time, and thereby considerably decreasing production costs.

The *E. coli* for isoprene production according to the present invention may have excellent isoprene productivity, thus to produce isoprene with high purity in large quantities.

DETAILED DESCRIPTION

Figure 1:
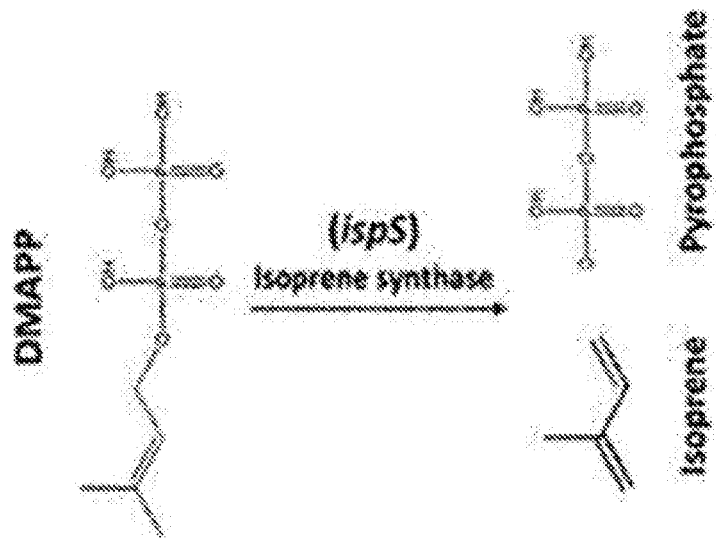
FIG. 1 illustrates an isoprene biosynthetic pathway including a mevalonate pathway and a MEP pathway.
Figure 1:
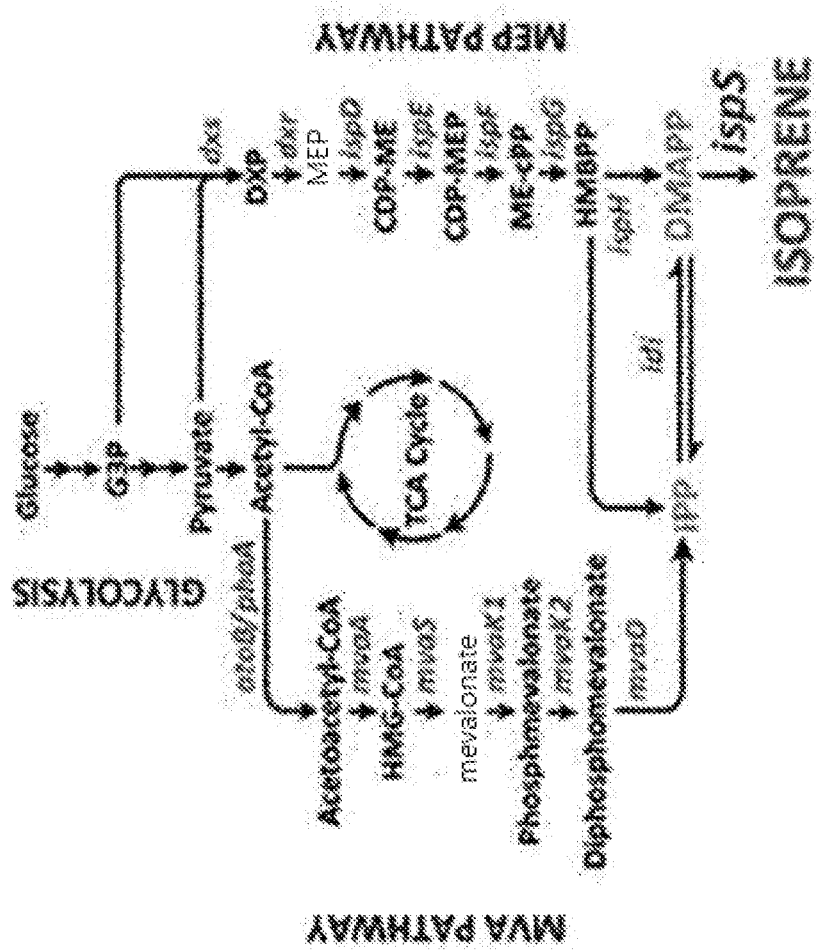

Hereinafter, the present invention will be described in detail by means of the following examples.

Example

1. Change in Increase of Isoprene Productivity According to Gene Arrangement Introduced in *E. coli* Host (1) Preparation of Plasmid for Isoprene Production Information on genes related to isoprene biosynthesis is shown in Table 1 below, while primers to amplify corresponding genes are shown in Table 2 below. The information on genes related to production of a precursor for isoprene biosynthesis is shown in Table 1 below, and a gene encoding an enzyme related to precursor biosynthesis used herein is pS-NA plasmid disclosed in Yoon et al. (2007).

TABLE 1

| SEQ ID NO. | Gene name | Enzyme name |
|---|---|---|
| 1 | ispS | Isoprene synthase derived from *Populus trichocarpa* |
| 2 | mvaE | Acetyl-CoA acetyl transferase/hydroxymethyl glutaryl (HMG)-CoA reductase derived from *Enterococcus faecalis* |
| 3 | mvaS | Hydroxymethyl glutaryl (HMG)-CoA synthase derived from *Enterococcus faecalis* |
| 4 | mvaK1 | Mevalonate kinase derived from *Streptococcus pneumoniae* |
| 5 | mvaD | Mevalonate diphosphate carboxylase derived from *Streptococcus pneumoniae* |
| 6 | mvaK2 | Phosphomevalonate kinase derived from *Streptococcus pneumoniae* |
| 7 | idi | Isoprenyl pyrophosphate isomerase derived from *Escherichia coli* MG1655 |
| 8 | idi | Isoprenyl pyrophosphate isomerase derived from *Synechocystis* sp. PCC6803 |

TABLE 1-continued

| SEQ ID NO. | Gene name | Enzyme name |
|---|---|---|
| 9 | idi | Isoprenyl pyrophosphate isomerase derived from *Streptococcus pneumoniae* |
| 10 | idi | Isoprenyl pyrophosphate isomerase derived from *Haematococcus plavialis* |
| 11 | ispS-L-Ecidi | Fusion gene of isoprene synthase derived from *Populus trichocarpa* (SEQ ID NO: 1) and isoprenyl pyrophosphate isomerase derived from *E. coli* MG1655 (SEQ ID NO: 7) |
| 12 | Ecidi-L-ispS | Fusion gene of isoprenyl pyrophosphate isomerase derived from *E. coli* MG1655 (SEQ ID NO: 7) and isoprene synthase derived from *Populus trichocarpa* |
| 13 | ispS-L-Syidi | Fusion gene of isoprene synthase derived from *Populus trichocarpa* (SEQ ID NO: 1) and isoprenyl pyrophosphate isomerase derived from *Streptococcus pneumoniae* (SEQ ID NO: 8) |
| 14 | Syidi-L-ispS | Fusion gene of isoprenyl pyrophosphate isomerase derived from *Streptococcus pneumoniae* (SEQ ID NO: 8) and isoprene synthase derived from *Populus trichocarpa* |
| 15 | pTrc99SN | Vector including strengthened ribosomal binding site sequence of pTrc99A |

For isoprene biosynthesis, the amplified gene or combined gene was introduced into pTrc99A vector (Bacterial expression vector with inducible lad promoter; amp resistance; restriction enzyme cloning) to prepare 4 types of vectors for isoprene production. *Populus trichocarpa*-derived isoprene synthase (ispS) was artificially synthesized and conformed to a codon of *E. coli* (SEQ ID NO: 1). Sequences for artificial synthesis were created using a DNA 2.0 program while artificial synthesis of gene was requested to Genescript (USA). The artificially synthesized *Populus trichocarpa* isoprene synthase was amplified through PCR using primers sPtispS-F and sPtispS-R in Table 2, cleaved by restriction enzymes NcoI and XbaI, and inserted into the same site of pTrc99A vector, thereby preparing pT-sPtispS.

TABLE 2

| SEQ ID NO. | Primer | Sequence |
|---|---|---|
| 16 | sPtispS-F | 5'-GCCATGGCTTGCTCTGTATCCAC-3' (SEQ ID NO. 16) |
| 17 | sPtispS-R | 5'-CTCTAGATTAGCGTTCGAACGGCAGAATTG-3' (SEQ ID NO. 17) |

Next, pTrc99SN was prepared by strengthening a ribosomal binding site in the pTrc99A vector (SEQ ID NO: 15) and amplified through PCR using the primers sPtispS-F and sPtispS-R in Table 2, followed by inserting the artificially synthesized *Populus trichocarpa* isoprene synthase therein, thereby preparing pTSN-sPtispS. Then, the plasmid pS-NA having the mavalonate pathway introduced therein was entirely amplified (SEQ ID NOS: 2 to 7) and introduced into an XbaI site of the above-prepared pTSN-sPtispS plasmid, thereby preparing pTSN-sPtispS-MVA. Following this, an ampicillin-resistant gene of the above-prepared pTSN-sPtispS-MVA (SEQ ID NO: 18) was removed using the restriction enzymes BglII and BspHI, followed by inserting a kanamycin-resistant gene (SEQ ID NO: 19) in the same site, thereby preparing pTSNK-sPtispS-MVA.

Transformation was executed by introducing the above-prepared plasmids for isoprene production, that is, pT-sPtispS, pTSN-sPtispS, pTSN-sPtispS-MVA and pTSNK-sPtispS-MVA, as well as pTrc99A vector as a negative control, separately, or together with pS-NA plasmid, into *E. coli* DH5. In this case, a transformation method used herein was in compliance with the typical method described in Sambrook and Russell (2001).

(2) Production of Isoprene Using *E. coli* DH5α Transformant

The present example describes that *E. coli* DH5a transformant including the above-prepared recombinant plasmids pT-sPtispS and pTSN-sPtispS, and the mevalonate pathway plasmid pS-NA (gene introduction of SEQ ID NOS: 2 to 7) introduced simultaneously therein is cultured in a medium containing glycerol to produce isoprene.

In order to investigate a difference in isoprene productivity according to the ribosomal binding strength, pT-sPtispS and pTSN-sPtispS, as well as the mevalonate pathway plasmid pS-NA were introduced into *E. coli* DH5a, separately and simultaneously.

5 ml TB medium including 100 μm/ml of ampicillin and 50 μm/ml of chloramphenicol (24 g yeast extract, 12 g tryptone, 9.4 g $K_2HPO_4$, 2.2 g $KH_2PO_4$ per liter) was inoculated with the transformant having isoprene productivity, and subjected to seed culture under conditions of 30° C. and 250 rpm. Thereafter, 50 ml TB medium including 20 g/L glycerol, 100 μm/ml of ampicillin and 50 μm/ml of chloramphenicol was inoculated with the above-seed cultured product and subjected to main culture. In order to increase an expression level of protein, an expression-inducing agent, that is, IPTG (Isopropyl β-D-1-thiogalactopyranoside) at a final concentration of 0.1 mM was added. The main culture was conducted in a 250 ml grooved conical flask under conditions of 30° C. and 150 rpm for 36 hours.

For quantitative analysis of isoprene, sampling was carried out from 6 hours to 36 hours after the culture at an interval of 2 hours. 700 μl of the cultured solution was mixed with equal amount of dodecane ($CH_3(CH_2)10CH_3$), followed by reacting the same at 30° C. for 10 minutes. Isoprene produced from the transformant for 10 minutes was entrapped in dodecane and the dodecane layer was isolated from the medium for quantitative analysis. The isoprene quantitative analysis was executed by using gas chromatography. 7890A model gas chromatograph of Agilent Co. (USA) was used. A column for sample separation used herein was 19091N-133 HP-INNOWAX column (length, 30 m; internal diameter, 0.25 mm; film thickness, 250 μm). An oven temperature started at 50° C. and, after 2 minutes, was raised up to 250° C. in a ratio of 30° C. per minute. Nitrogen was used as a carrier gas and a gas input pressure was set to be 15.345 psi. A flame ionization detector (FID) was employed at a temperature set to be 280° C. A time for separation of isoprene was 1.53 minutes and an isoprene standard material for quantification was purchased from Sigma Co. (USA).

Figure 2:
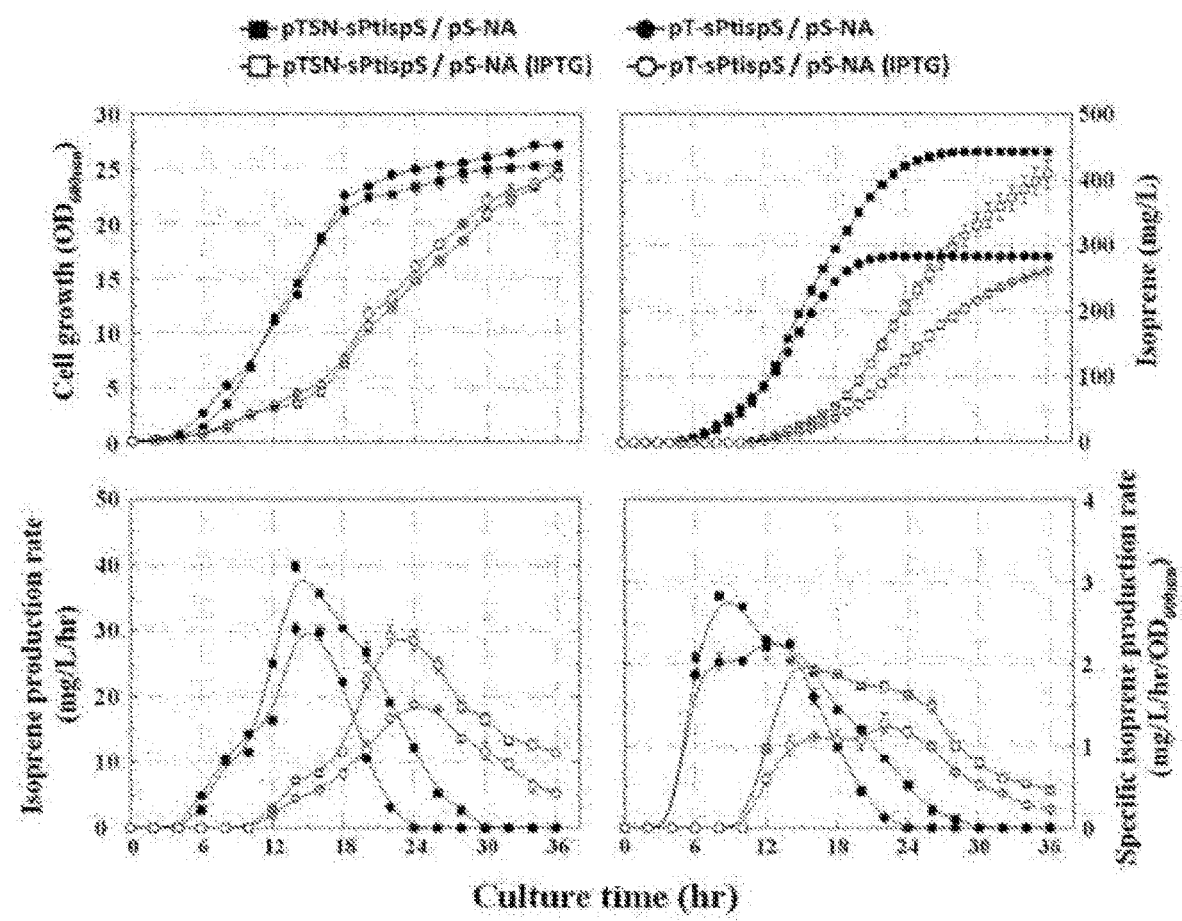
FIG. 2 illustrates the cell growth of *E. coli* strain and the isoprene production amount, wherein a plasmid including artificially synthesized *Populus trichocarpa* isoprene synthase and a plasmid including a mevalonate pathway are simultaneously introduced into the strain.

Culture results are shown in FIG. 2. Referring to FIG. 2, it was demonstrated that an isoprene production amount of about 450 mg/L was obtained in the culture without addition of IPTG, the transformant including the simultaneously introduced pTSN-sPtispS and pS-NA, which are plasmids having a strong ribosomal binding site. This value is about 1.6 times higher than the transformant including the simultaneously introduced pT-sPtispS and pS-NA that has produced about 280 mg/L of isoprene. The highest difference in the isoprene production amount per hour between the above two strains was about 10 mg/L/hr. There was little difference in the cell growth rate, and a final optical density (OD) was about 25.

For the culture having PTG added thereto, both strains exhibited inhibition of initial cell growth, however, exhibited final cell growth substantially not different from that in the culture without addition of IPTG. Further, due to the inhibition of initial cell growth, initial isoprene production amount was relatively lower than the culture without addition of IPTG. However, from 18 hours after the culture, the isoprene production amount was also increased along with the cell growth. As a result, 420 mg/L of isoprene was produced in the transformant including the simultaneously introduced pTSN-sPtispS and pS-NA, which is 1.6 times higher than the transformant including the simultaneously introduced pT-sPtispS and pS-NA (260 mg/L).

Consequently, the transformant including the plasmids having a strong ribosomal binding site, that is, pTSN-sPtispS and pS-NA, simultaneously introduced therein, demonstrated excellent isoprene productivity, as compared to the transformant including pT-sPtispS and pS-NA. This is considered as a result of increasing the expression level of isoprene synthase due to the strong ribosomal binding site.

In the culture having IPTG added thereto for increasing the protein expression level, causes of inhibiting initial cell growth are as follows. An expression level of the isoprene synthase cloned in a vector including a strong promoter and having a high plasmid copy number is far higher than the mevalonate pathway cloned in a vector that include relatively weak promoter and has a low plasmid copy number. Thereby, it is considered that DMAPP as a precursor is excessively consumed and causes a lack of DMAPP required for cell growth, resulting in inhibition of initial cell growth.

(3) Improved Isoprene Productivity According to Increase of Expression Level of Precursor Production Pathway The present example describes that, in order to solve the problem of cell growth inhibition due to lack of DMAPP described in Example 1-(2), a plasmid with increased expression level of mevalonate pathway is utilized to improve the isoprene productivity. The plasmid with increased expression level of mevalonate pathway, that is, pTSN-sPtispS-MVA integrated plasmid was prepared. In order to improve stability of this plasmid, pTSNK-sPtispS-MVA was prepared by replacing the ampicillin-resistant gene with a kanamycin-resistant gene.

The method of preparing these two plasmids was already described in Example 1-(1).

First, E. coli DH5α transformant introduced with pTSN-sPtispS-MVA having an increased expression level of mevalonate pathway was prepared. Further, a transformant simultaneously introduced with pTSN-sPtispS and pS-NA was used as a control group. Then, these were cultured to investigate whether isoprene productivity is improved or not.

The culture medium, culture conditions and isoprene quantitation were the same as those described in the method according to Example 1-(2), except that IPTG was not added.

Figure 3:
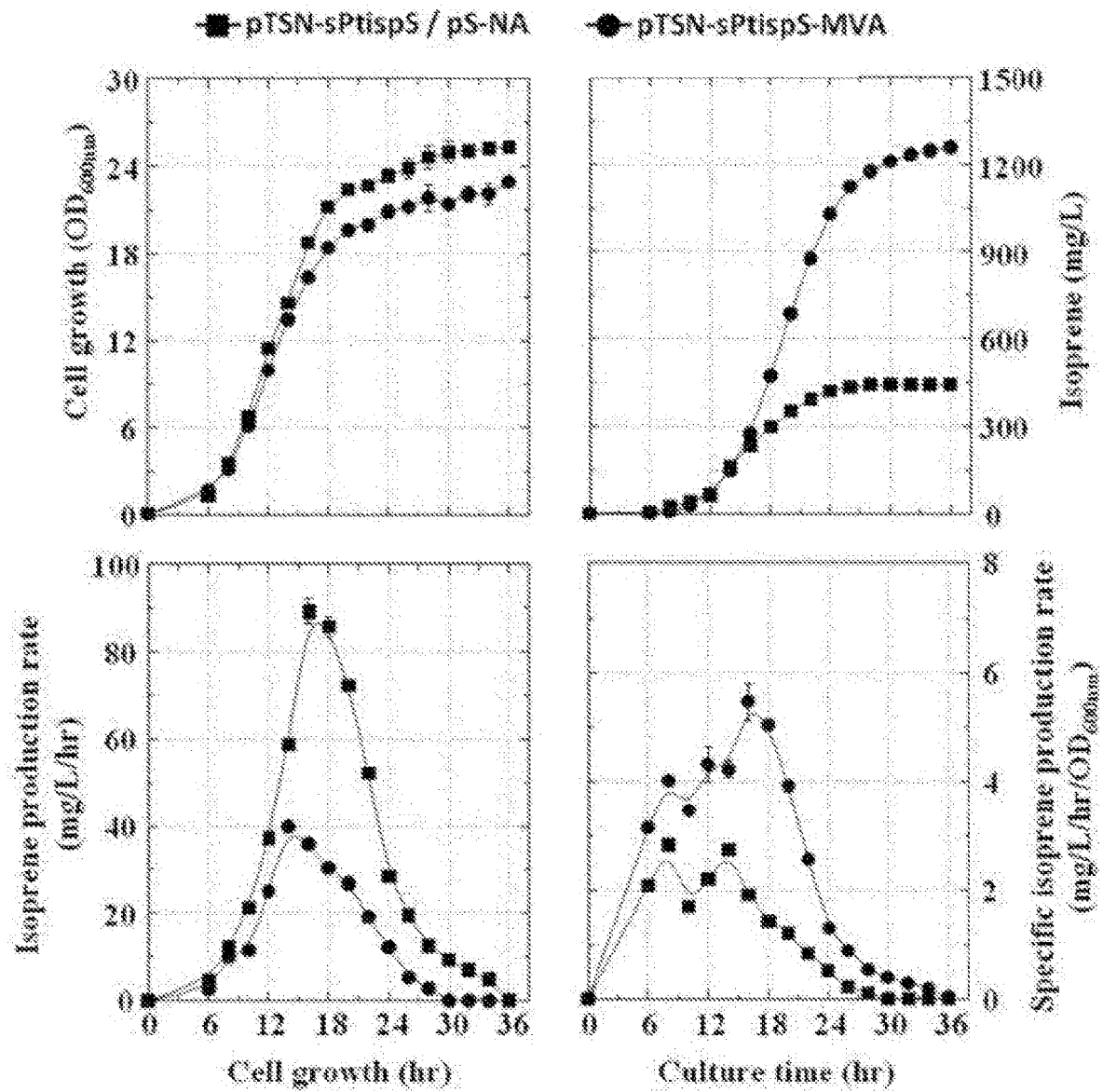
FIG. 3 illustrates isoprene productivity by integrated plasmid having isoprene synthase and a mevalonate pathway, simultaneously.

Culture results are shown in FIG. 3. Referring to FIG. 3, it was demonstrated that an isoprene production amount of 1.25 g/L was obtained in the strain introduced with the integrated plasmid having an increased expression level of mevalonate pathway, which is about 3 times higher than that of the control group. Further, an isoprene production amount per time (maximum about 90 mg/L/hr) and an isoprene production amount per unit cell (maximum about 5.5 mg/L/hr/OD 600 nm) in the strain were also far higher than those of the control group. However, inhibition of cell growth was not observed.

The improvement of isoprene productivity is considered as a result of solving the problem entailed in lack of DMAPP indicated in Example 1-(2) by increasing the expression of mevalonate pathway which is a pathway for production of precursor. Further, it is also considered that the above result may be obtained by improving the isoprene productivity due to the balanced expression of IspS and MVA pathway.

(4) Improved Isoprene Productivity by Improvement of Plasmid Stability

The present example describes that, in order to solve a problem of losing the integrated plasmid during culture in Example 1-(3), bla (SEQ ID NO: 18) encoding an ampicillin-resistant gene in the integrated plasmid is replaced with nptII (SEQ ID NO: 19) encoding a kanamycin-resistant gene to produce another plasmid, which is utilized to improve isoprene productivity.

During culture of E. coli including the integrated plasmid, it was investigated whether the plasmid was lost or not. In order to identify stability of plasmid, a culture solution under culturing was diluted with the medium and then spread on a solid medium without antibiotics and another solid medium containing antibiotics, respectively, with the same amount, followed by performing measurement in every 6 hours. In order to determine the plasmid stability, the number of colonies in the medium containing antibiotics was denoted by % to 100% of the number of colonies in the medium without antibiotics.

Figure 4:
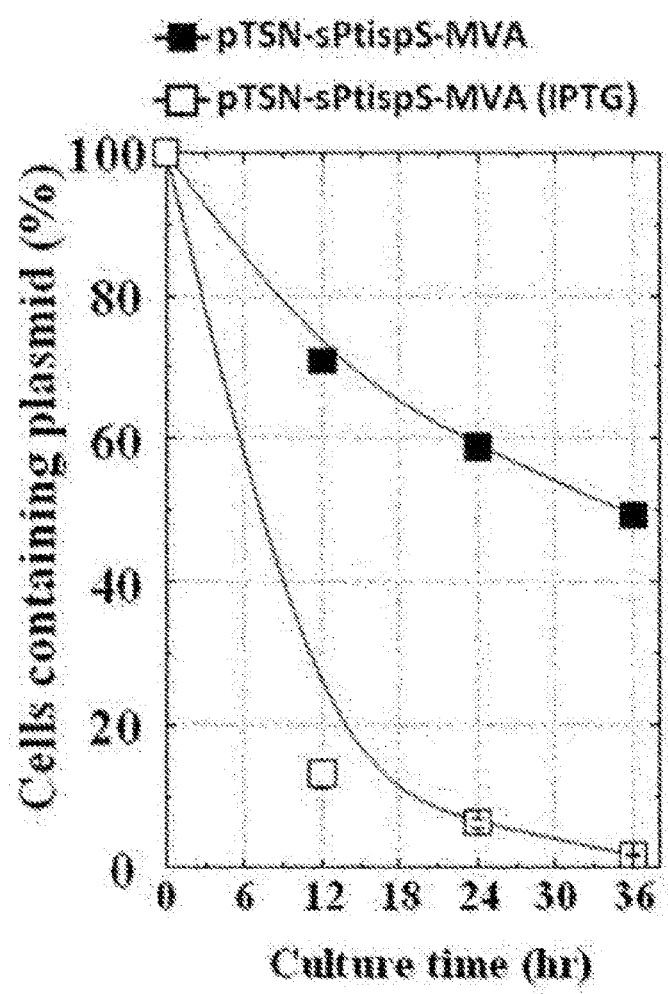
FIG. 4 illustrates plasmid stability in *E. coli* of integrated plasmid having isoprene synthase and a mevalonate pathway, simultaneously.

Identified results of plasmid stability are shown in FIG. 4. Referring to FIG. 4, as a result of identifying the plasmid stability, it was found that the number of E. coli containing plasmid at the end of culture, that is, after 36 hours, was 50% or less, while a loss rate of plasmid in the culture with the addition of IDTG was far higher than the culture without addition thereof.

In order to solve the problem of low plasmid stability, bla encoding ampicillin-resistant gene in the integrated plasmid was replaced with nptII encoding kanamycin-resistant gene thus to prepare a new pTSNK-sPtispS-MVA plasmid. In order to investigate a variation in the isoprene productivity according to the improved plasmid stability, the strains were cultured.

The culture medium, culture conditions and isoprene quantitation were the same as those described in the method according to Example 1-(2), except that IPTG was not added.

Figure 5:
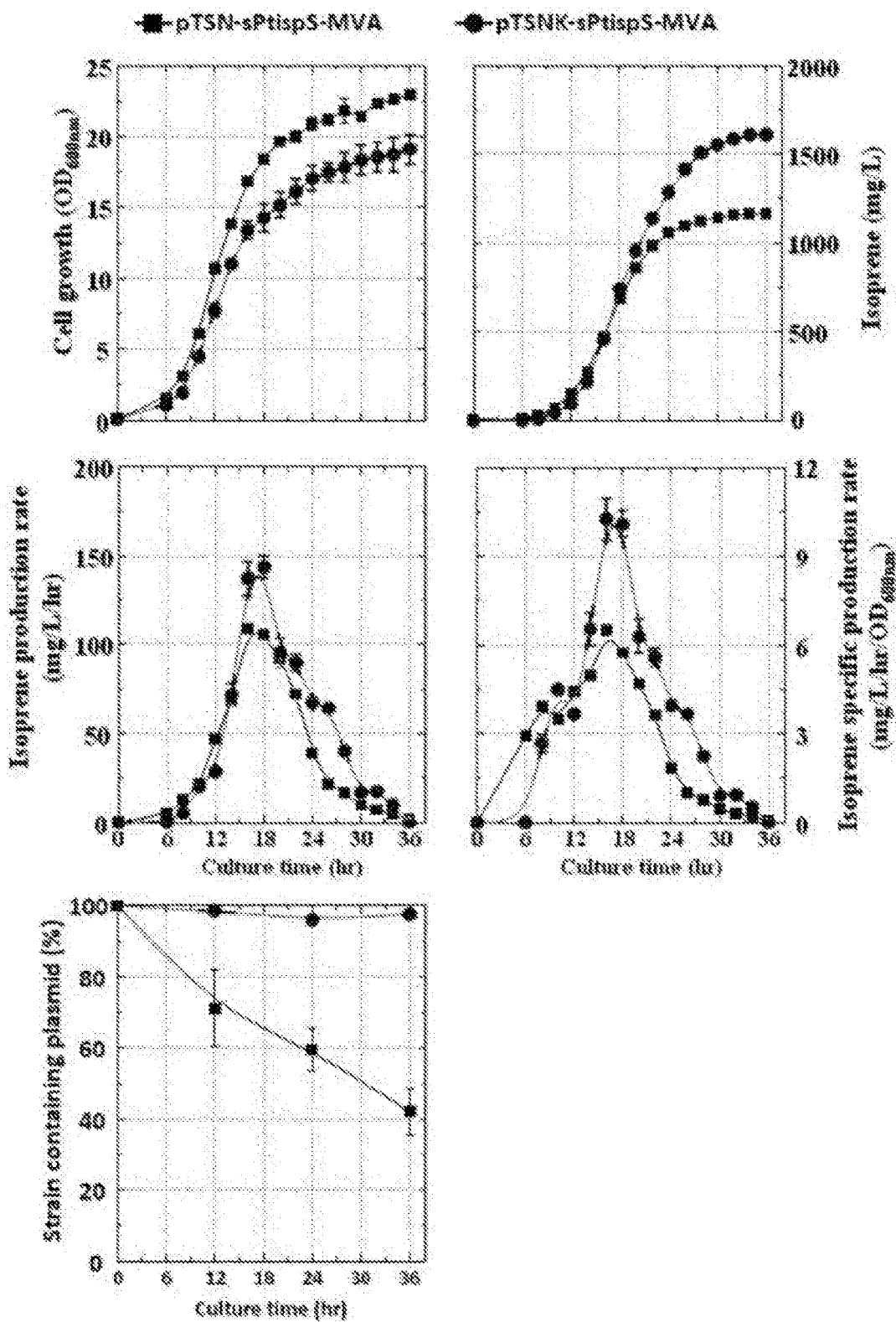
FIG. 5 illustrates cell growth, isoprene productivity and plasmid stability of *E. coli* transformant into which a plasmid with improved stability of integrated plasmid is introduced.

Culture results are shown in FIG. 5. Referring to FIG. 5, it was found that about 1.6 g/L of isoprene was produced in the strain introduced with plasmid having the improved stability, which is about 1.3 times higher than the control group. Plasmid stability was also far superior, compared to the control group. Further, it was found that about 90% or more plasmid was remaining at the end point of culture, that is, 36 hours after the culture. From 14 hours after the culture, in the strain introduced with plasmid having the kanamycin-resistant gene, it could be seen that the isoprene production amount per hour and the isoprene production amount per unit cell were increased. It is considered that such an improvement is a result of the improved stability of the plasmid.

2. Improved Isoprene Productivity by Improvement of E. Coli Host Strain (1) Change in Isoprene Productivity According to E. Coli Strain The E. coli strain used in Example 1, that is, DH5α is a thiamine biosynthetic gene-deleted strain and cannot produce thiamine by itself. For this reason, thiamine should be added to the medium, thus bearing burden of expenses.

Further, the above strain has a disadvantage of lower growth rate than *E. coli* MG1655 strain which is mostly used in industrial applications.

The present example compares isoprene production abilities between the host *E. coli* mentioned in Example 1, that is, DH5α and MG1655 strains, investigates gene factors influencing on isoprene productivity in these two host strains and describes utility of MG1655 more applicable in the industry as a host strain for isoprene production.

First, pTSNK-sPtispS-MVA was introduced into DH5α and MG1655 strains, respectively, to prepare *E. coli* transformants, followed by performing comparison of isoprene productivity.

The culture medium, culture conditions and isoprene quantitation were the same as those described in the method according to Example 1-(2), except that IPTG was not added.

Figure 6:
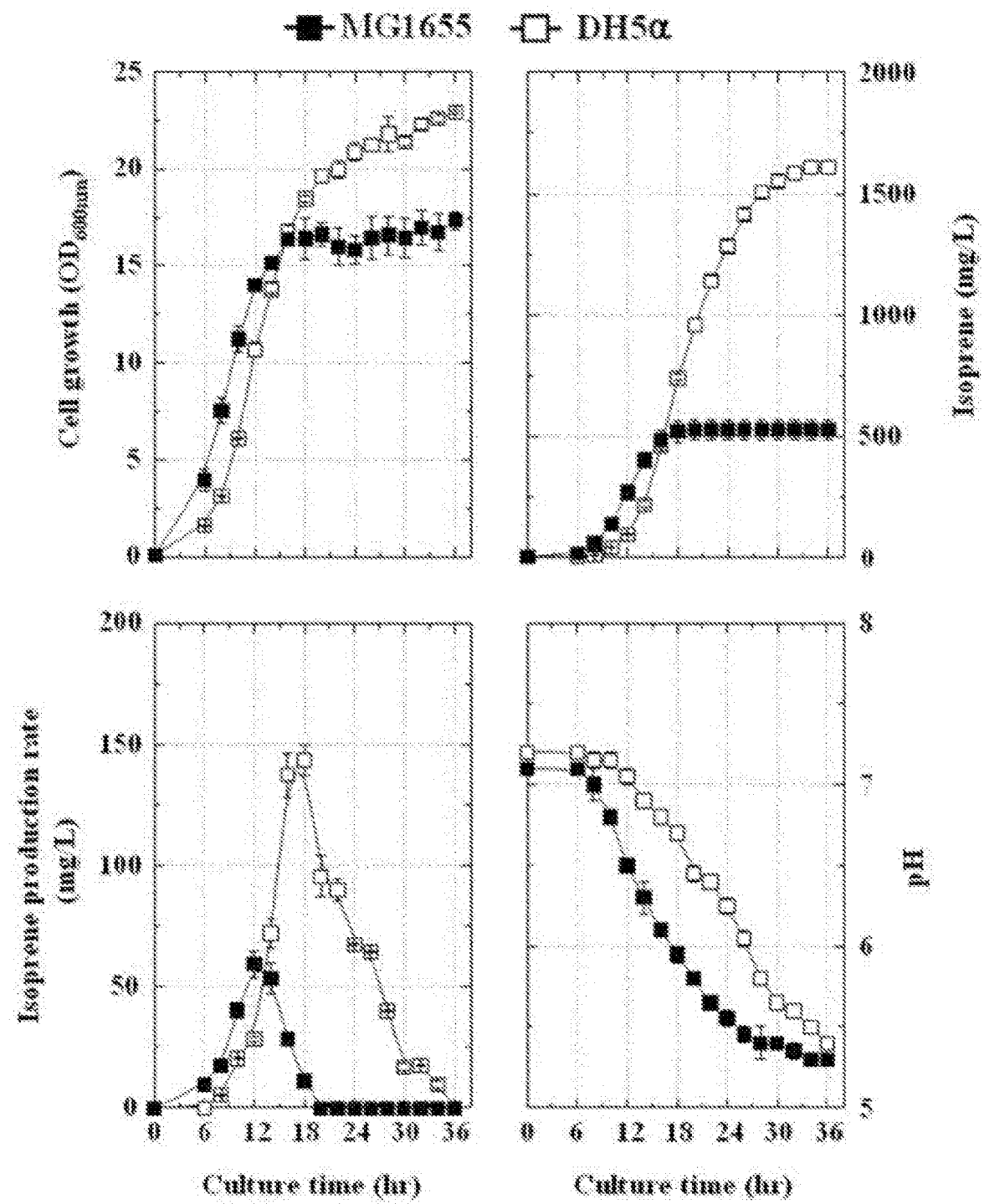
FIG. 6 illustrates a difference in isoprene productivity between *E. coli* DH5a and MG1655.

Culture results are shown in FIG. 6. Referring to FIG. 6, it can be seen that *E. coli* DH5α transformant exhibited an isoprene production amount of 3.2 times higher than that of MG1655 transformant. Although MG1655 transformant had faster cell growth, and a final cell growth amount was a little lower with a fast reduction in pH, than *E. coli* DH5α transformant.

It is considered that such a difference in the isoprene productivity is a result of genetic features between the *E. coli* strains. In addition, for MG1655 strain, it quickly consumes a carbon source while generating and accumulating fermentation by-product such as an organic acid. Therefore, it is determined that pH was rapidly decreased to cause a reduction in the isoprene productivity.

(2) Identification of Factor Showing Difference in Isoprene Productivity Between *E. coli* Strains Based on the results in Example 2-(1), the present example investigates a gene factor to cause a difference in the isoprene productivity between the host *E. coli* DH5α and the MG1655 strain, and therefore, describes that a result of isoprene productivity similar to or more improved than that of *E. coli* DH5α strain may be obtained by changing a gene form of the *E. coli* MG1655 strain.

MG1655 ΔrecA and MG1655 ΔrelA strains, in which a gene deleted from the *E. coli* DH5α strain, that is, recA (SEQ ID NO: 76) and relA were deleted from wild type MG1655 strain, respectively, were prepared. Deletion of genes was conducted by means of a gene deletion kit (Quick & Easy *E. coli* Gene Deletion Kit by Red®/ET® Recombination, Gene Bridges, Germany) and the gene was deleted using the kit according the instruction for use of the kit.

After simultaneously introducing pTSNK-sPtispS-MVA and pS-NA into each of the gene-deleted *E. coli* strains to form an *E. coli* transformant, isoprene productivity of the transformant was compared to that of the control group, that is, the wild type *E. coli* MG1655 and DH5α transformants.

The culture medium, culture conditions and isoprene quantitation were the same as those described in the method according to Example 1-(2), except that IPTG was not added.

Figure 7:
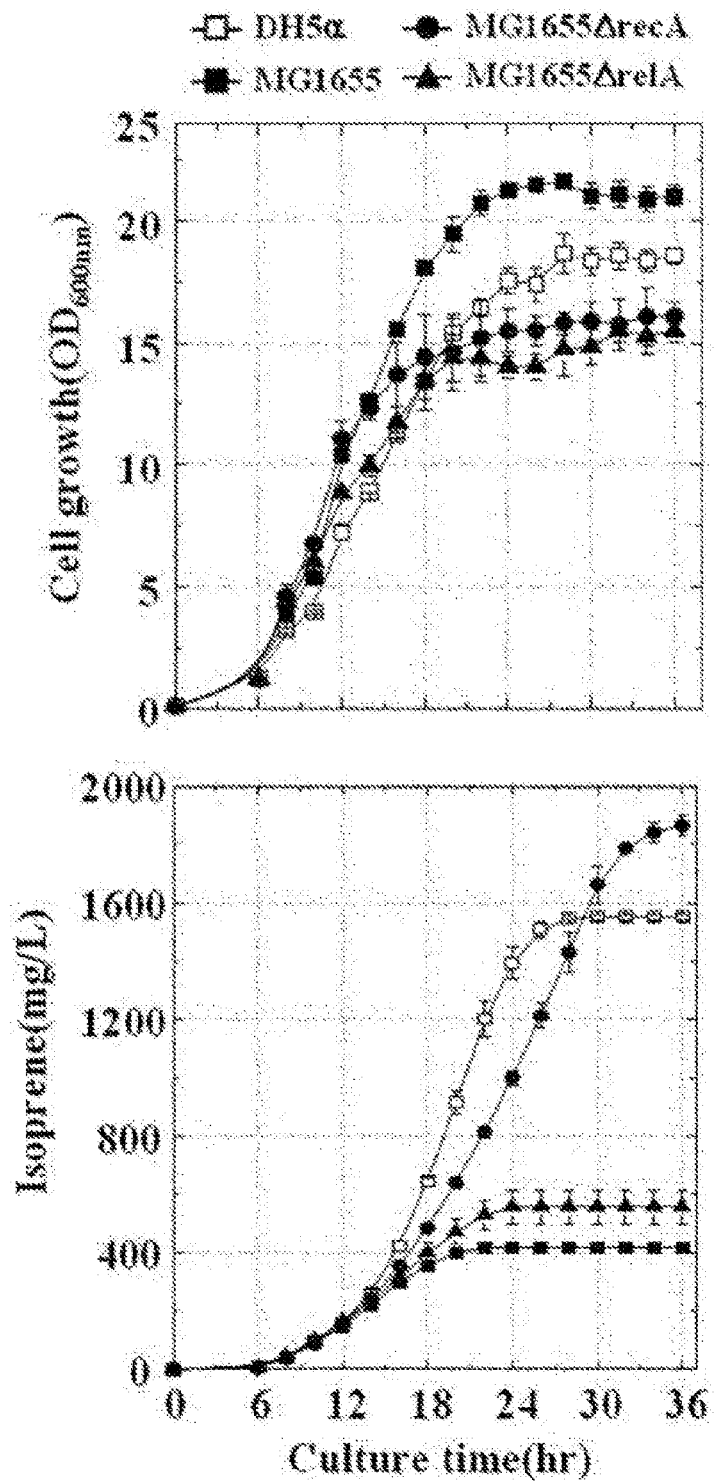
FIG. 7 illustrates a result of comparing isoprene productivity between recA and relA-deleted strain of MG 1655.

Culture results are shown in FIG. 7. Referring to FIG. 7, it was found that the MG1655 recA strain exhibited an isoprene production amount of 4.6 times and 1.3 times higher than those of the wild type MG1655 and the DH5α strains, respectively. However, relA-deleted strain did not have a difference in the isoprene productivity, compared to the wild type MG1655 strain.

Based on the above study results, it was identified that the gene factor, which shows a difference in the isoprene productivity between DH5α and MG1655 (DE3), is recA.

(3) Increase of Isoprene Productivity by nudB Deletion

The present example concretely describes that the isoprene productivity is improved by deleting nudB which is a gene for transforming isoprene precursors, that is, IPP and DMAPP into 3-methyl-3-buten-1-ol and 3-methyl-2-buten-1-ol, respectively, as well as results thereof.

In order to prevent undesirable consumption of DMAPP as a precursor of isoprene synthase so as to improve the isoprene productivity, a strain with deletion of NudB gene (SEQ ID NO: 77) from the wild type MG1655 strain was prepared.

PCR primers for gene deletion are shown in Table 3 below. The gene-deleted strain was prepared by the same method according to Example 2-(2), and the above-prepared strain was named MG1655ΔnudB.

After introducing pTSNK-sPtispS-MVA into MG1655ΔnudB strain to form a *E. coli* transformant, isoprene productivity of the transformant was compared to that of the control group, that is, the wild type *E. coli* MG1655 transformant.

5 ml TB medium including 50 μm/ml of kanamycin (24 g yeast extract, 12 g tryptone, 9.4 g $KH_2PO_4$, 2.2 g $KH_2PO_4$ per liter) was inoculated with the transformant having isoprene productivity, and subjected to seed culture under conditions of 37° C. and 250 rpm. Thereafter, 50 ml TB medium including 20 g/L of glycerol and 50 μm/ml of kanamycin was inoculated with the seed cultured product and subjected to main culture. In order to increase a protein expression level, an expression-inducing agent, that is, lactose at a final concentration of 5 g/l was added. The main culture was conducted in 250 ml grooved conical flask under conditions of 30° C. and 150 rpm for 36 hours. The isoprene quantitation was performed according to the same procedures as described in the method according to Example 1-(2), except that IPTG was not added.

Figure 8:
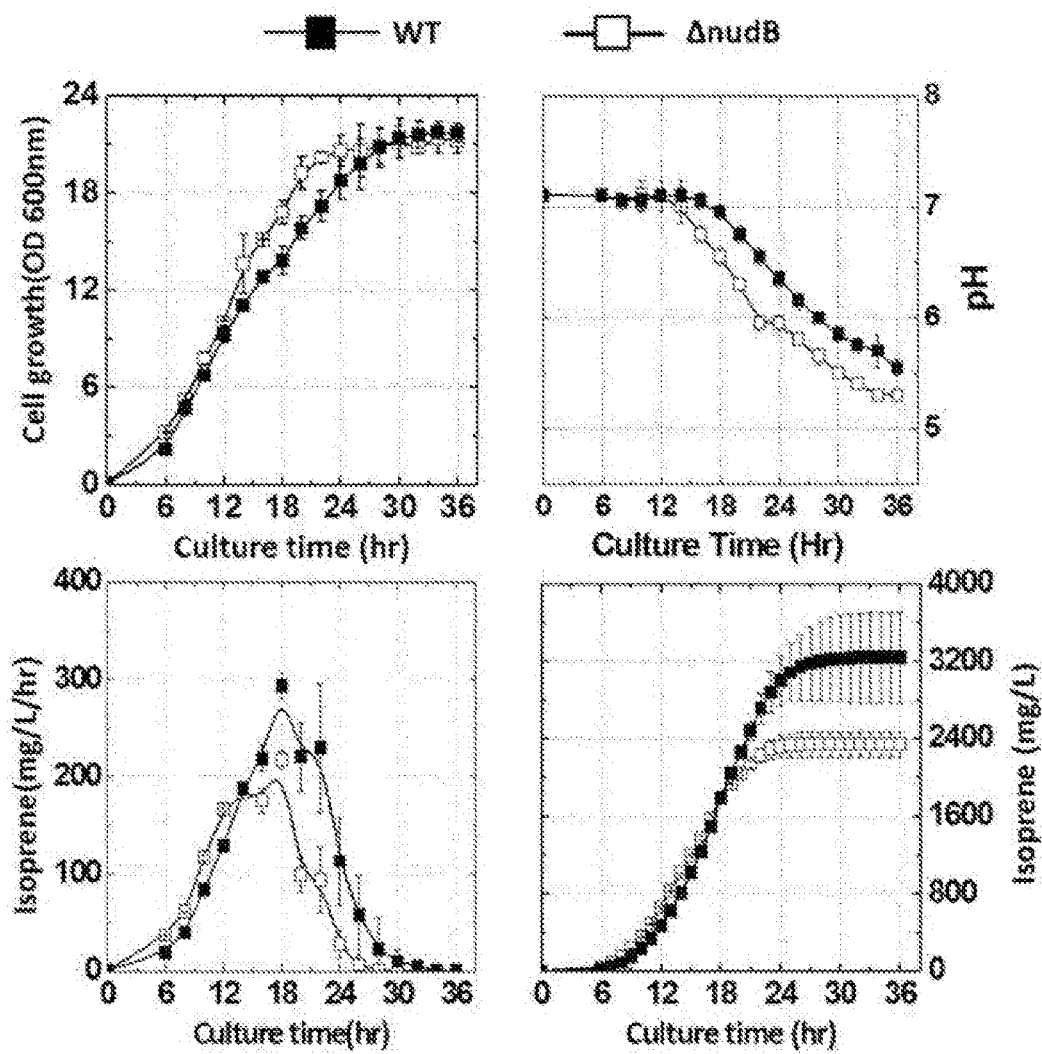
FIG. 8 illustrates a result of comparing isoprene productivity between MG1655 and nudB-deleted strain of MG1655.

Culture results are shown in FIG. 8. Referring to FIG. 8, it was found that the MG1655 nudB strain had an isoprene production amount of about 1.35 times higher than that of the wild type MG1655 strain. From the result, it could be confirmed that nudB deletion was helpful for improving the isoprene productivity.

TABLE 3

| SEQ ID NO. | Primer | Sequence |
|---|---|---|
| 78 | ΔnudB-F | ATAACTATGTGAATGGGATGAGCGAAGGCAG TCAACGAAGAGGCAGCGTGCATATTTATTAC CTCCTTGTAGGC (SEQ ID NO. 78) |
| 79 | ΔnudB-R | TAAAAATATCTCCAGATAGCCCTGCCTGTTC AGGCAGCGTTAATTACAAACATATGAATATC CTCCTTAGTTCC (SEQ ID NO. 79) |
| 80 | nudB-CF-F1 | CAGGACCGTAACCTTCGTAGATG (SEQ ID NO. 80) |
| 81 | nudB-CF-F2 | CAAACTCTACCGTGCGCTGAC (SEQ ID NO. 81) |
| 82 | nudB-CF-R | GACCGTCTGACCATGCTGCTG (SEQ ID NO. 82) |
| 83 | Δflagella-F | TTCCACTTTGCCAATAACGCCGTCCATAATC AGCCACGAGGTGCGCGATGGGGGATCCGTCG ACCTGCAG (SEQ ID NO. 83) |

TABLE 3-continued

| SEQ ID NO. | Primer | Sequence |
|---|---|---|
| 84 | Δflagella-R | AGACGCGGATTACGGTGCTACCTCTGACGTT AGGCGAAAATATCAACGCCCATATTTATTAC CTCCTTGTAGGCTGGAGC (SEQ ID NO. 84) |
| 85 | FlaCF-F | GAGTGAATTTTTCTGCCTGCG (SEQ ID NO. 85) |
| 86 | FlaCF-R | GCTTGCTTTTCTTGCTTATCGC (SEQ ID NO. 86) |

(4) Increase of Isoprene Productivity by Simultaneous Deletion of nudB and recA

Based on the results of Examples 2-(2) and 2-(3), the present example describes that the isoprene productivity is improved by simultaneously deleting nudB and recA, as well as results thereof.

MG1655ΔnudB strain was integrated with MG1655ΔrecA strain through P1 transduction, thereby preparing MG1655ΔnudB and recA strains. Then, after introducing pTSNK-sPtispS-MVA into MG1655ΔnudB and recA strains to prepare an E. coli transformant, isoprene productivity of this transformant was compared to that of the control group, that is, MG1655ΔrecA and MG1655ΔnudB strain transformants.

The culture medium and culture conditions are the same as those in Example 2-(3), and isoprene quantitation is the same as the method according to Example 1-(2).

Figure 9:
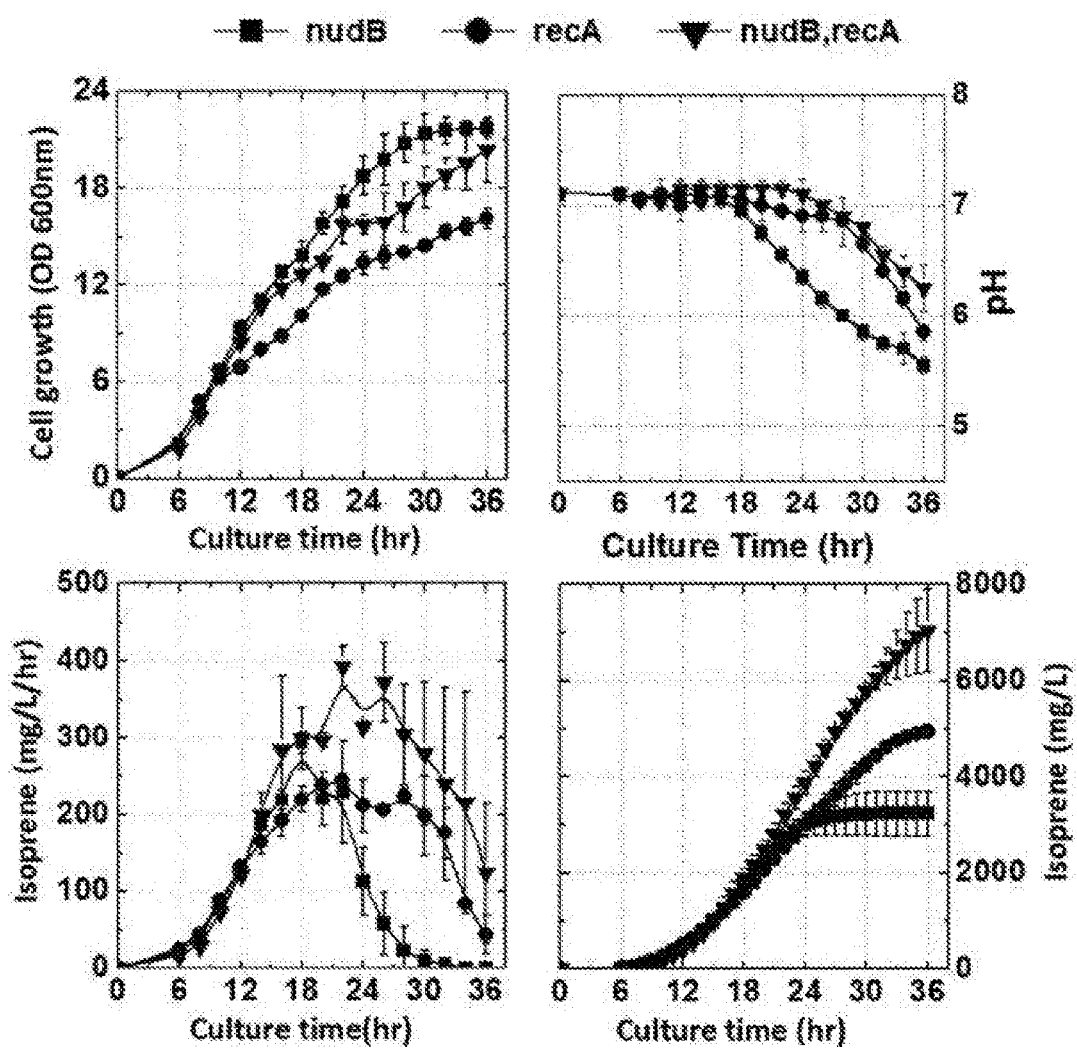
FIG. 9 illustrates a result of comparing isoprene productivity between nudB-deleted strain, recA-deleted strain, nudB and recA-co-deleted strain of MG1655.

Culture results are shown in FIG. 9. Referring to FIG. 9, it was found that MG1655 nudB and recA strains exhibited an isoprene production amount of 1.4 times and 2.15 times higher than those of MG1655ΔrecA and MG1655ΔnudB strains, respectively. From the result, it could be confirmed that simultaneous deletion of nudB and recA was helpful for improving the isoprene productivity.

(5) Identification of Isoprene Productivity by Removal of Flagella

The present example describes that isoprene productivity is improved by deleting operon (SEQ ID NO: 93) which includes genes related to the formation of flagellar (e.g., fliF (SEQ ID NO: 87), fliG (SEQ ID NO: 88), fliH (SEQ ID NO: 89), fliI (SEQ ID NO: 90), fliJ (SEQ ID NO: 91), and fliK (SEQ ID NO: 92), as well as results thereof.

A great amount of ATP is consumed for activating flagella. However, in a culture circumstance suitable for microorganism growth, which is artificially controlled, instead of the wild condition, movement of flagella is not necessary. Therefore, the isoprene productivity was improved by preventing undesirable consumption of ATP, and flagellum-deleted MG1655 strain was prepared by deleting the operon of genes related to the formation of flagella in the MG1655 strain.

PCR primers for gene deletion are shown in Table 3. The gene-deleted strain was prepared by the same method according to Example 2-(2), and the above-prepared strain was named MG1655Δfli operon.

After introducing pTSNK-sPtispS-MVA into the MG1655Δfli operon strain to prepare an E. coli transformant, isoprene productivity of the transformant was compared to that of the control group, that is, the wild type E. coli MG1655 transformant.

5 ml 2YT medium including 50 μm/ml of kanamycin (10 g yeast extract, 16 g tryptone, 5 g NaCl per liter) was inoculated with the transformant having isoprene productivity, and subjected to seed culture under conditions of 37° C. and 250 rpm. Thereafter, 50 ml MR medium including 20 g/L of glycerol and 50 μm/ml of kanamycin (KH$_2$PO$_4$ 22 g, (NH4)2HPO4 3 g, MgSO4·7H2O 0.7 g, Citrate 0.8 g, Trace metal solution (ZnSO4·7H2O 0.55 g, MnSO4·H2O 1.25 g, Na2B4O7·10H2O 0.05 g, FeSO4·7H2O 50 g, CuSO4.5H2O 2.5 g, CaCl2 5 g, (NH4)6Mo7O24·4H2O 0.25 g per liter) 2 ml per liter) was inoculated with the seed cultured product and subjected to main culture. In order to increase a protein expression level, an expression-inducing agent, that is, lactose at a final concentration of 5 g/l was added. The main culture was conducted in 250 ml grooved conical flask under conditions of 30° C. and 150 rpm for 48 hours. The isoprene quantitation was performed according to the same procedures as described in the method according to Example 1-(2), except that IPTG was not added.

Figure 10:
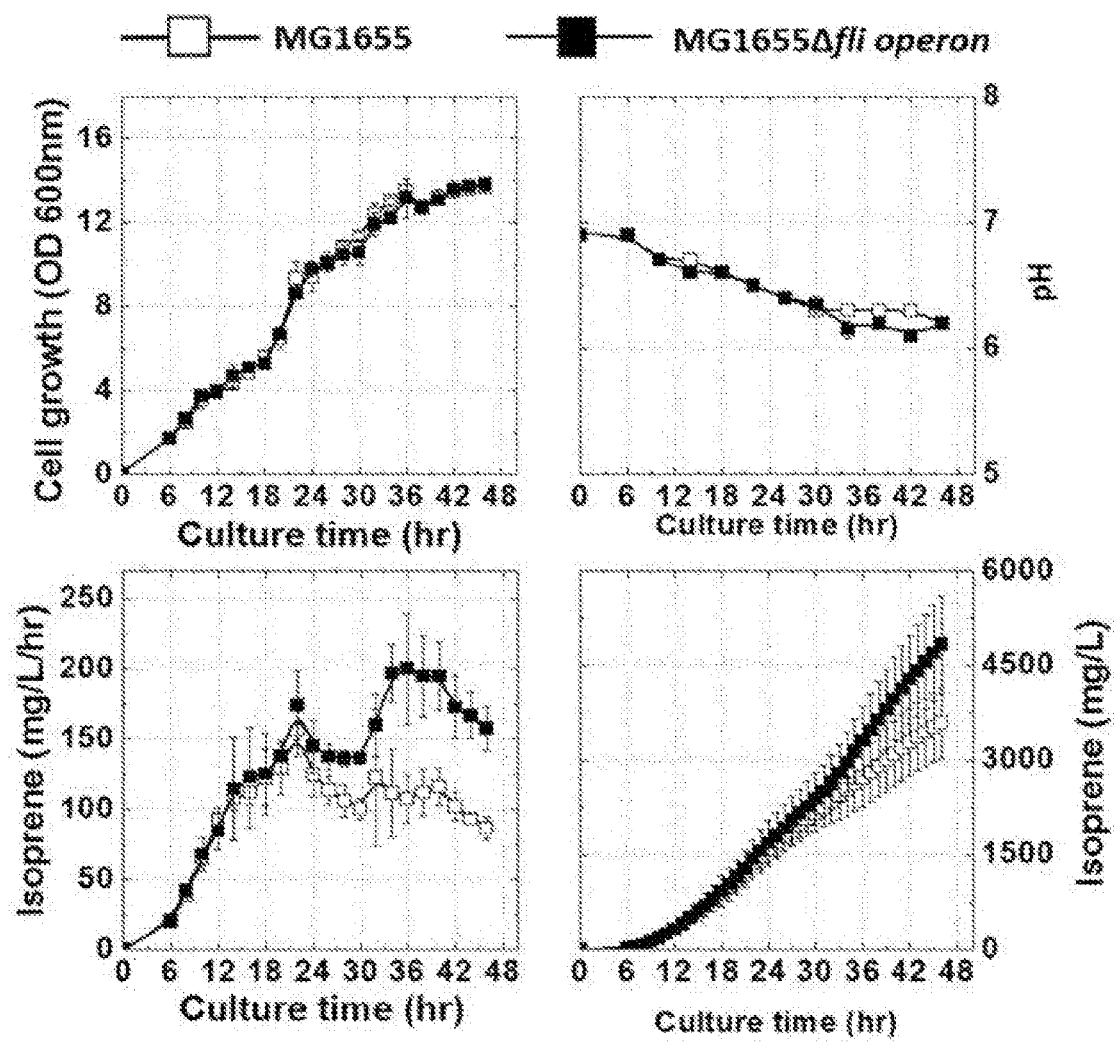
FIG. 10 illustrates a result of comparing isoprene productivity between MG1655 and fli operon-deleted strains of MG1655.

Culture results are shown in FIG. 10. Referring to FIG. 10, it was found that the MG1655fli operon strain exhibited an isoprene production amount of about 1.3 times higher than the wild type MG1655 strain. From the result, it could be confirmed that removal of flagella was helpful for improving the isoprene productivity.

3. Increase of Isoprene Productivity According to Improvement of Carbon Source Use Efficiency (1) Preparation of Strain with Improved Carbon Source Use Efficiency The present example describes preparation of E. coli MG1655 strain with improved carbon source use efficiency.

In order to prevent undesirable consumption of a mevalonate pathway precursor, that is, acetyl-CoA, and improve isoprene productivity and carbon source use efficiency, a strain with deletion of 9 genes related to biosynthesis of organic acid and alcohol from the wild type MG1655 strain was prepared.

Figure 11:
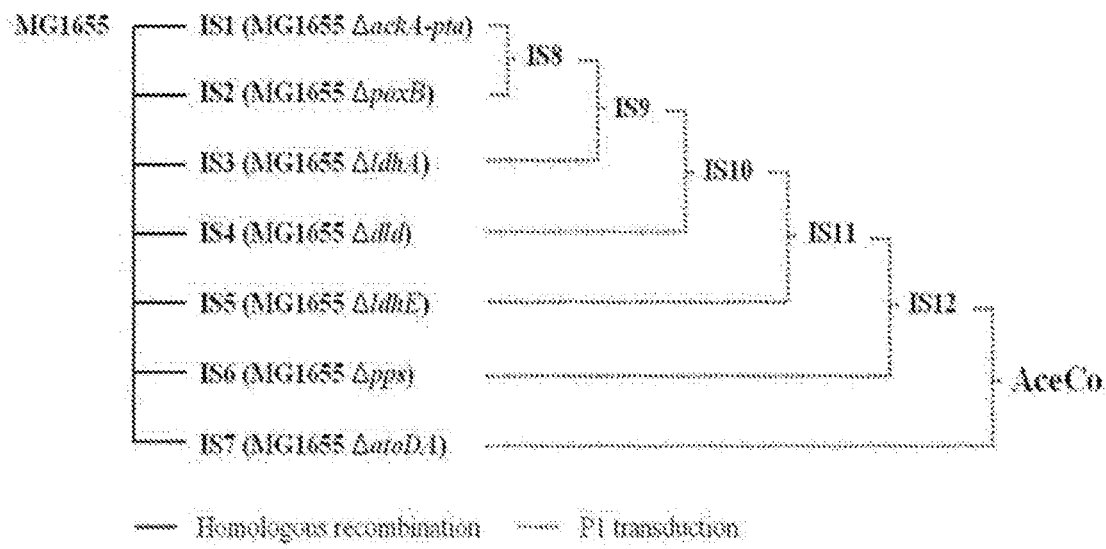
FIG. 11 illustrates a process of preparing AcoCo strains in diagram form, to exhibit a gene to be removed for acetyl-CoA and pyruvate metabolic pathway and for preparing AceCo strains.
Figure 11:
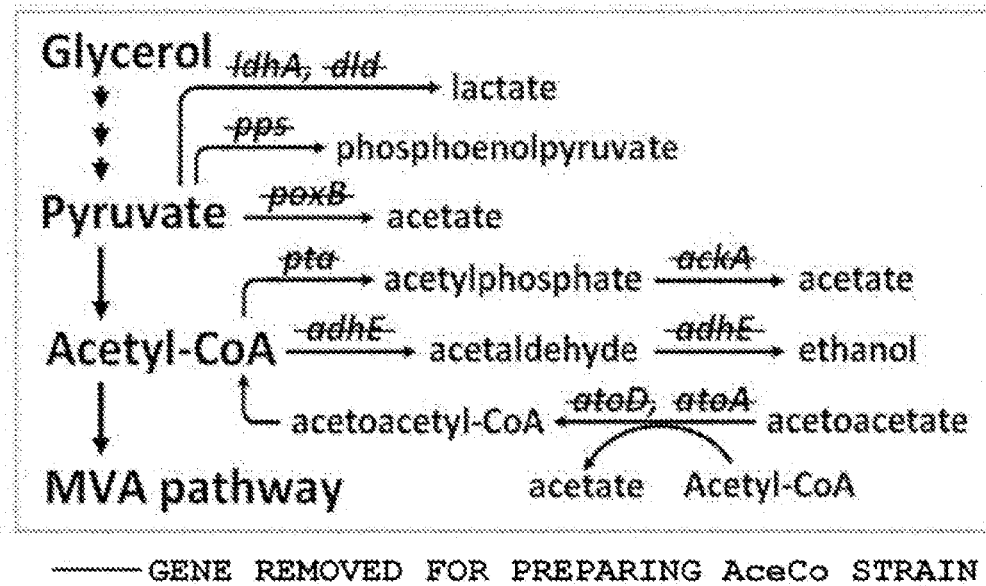

PCR primers for gene deletion, a list of deletion strains and a deletion process are shown in Table 4 and FIG. 11.

TABLE 4

| Name | SEQ ID NO. | Sequence |
|---|---|---|
| Primer | | |
| ΔackA-pta-F | 20 | TGGCTCCCTGACGTTTTTTAGCCACGTATCAATTATAGGTACTTCC ATGAATTAACCCTCACTAAAGGGCG (SEQ ID NO. 20) |
| ΔackA-pta-R | 21 | GCAGCGCAAAGCTGCGGATGATGACGAGATTACTGCTGCTGTCAG ACTGTAATACGACTCACTATAGGGCTC (SEQ ID NO. 21) |
| ackA-ptaCF-F | 22 | TGTCATCATGCGCTACGCTC (SEQ ID NO. 22) |

TABLE 4-continued

| Name | SEQ ID NO. | Sequence |
|---|---|---|
| ackA-ptaCF-R | 23 | CAGTTAAGCAAGATAATCAG (SEQ ID NO. 23) |
| ΔpoxB-F | 24 | GATGAACTAAACTTGTTACCGTTATCACATTCAGGAGATGGAGAAC CATGAATTAACCCTCACTAAAGGGCG (SEQ ID NO. 24) |
| ΔoxB-R | 25 | CCTTATTATGACGGGAAATGCCACCCTTTTTACCTTAGCCAGTTTGT TTTTAATACGACTCACTATAGGGCTC (SEQ ID NO. 25) |
| poxBCF-F | 26 | TTACGTACTGGCCTGCTCCTGC (SEQ ID NO. 26) |
| poxBCF-R | 27 | GTCGGGTAACGGTATCACTGCG (SEQ ID NO. 27) |
| ΔldhA-F | 28 | ATTTTTAGTAGCTTAAATGTGATTCAACATCACTGGAGAAAGTCTTA TGAAATTAACCCTCACTAAAGGGCG (SEQ ID NO. 28) |
| ΔldhA-R | 29 | CTCCCCTGGAATGCAGGGGAGCGGCAAGATTAAACCAGTTCGTTCG GGCATAATACGACTCACTATAGGGCTC (SEQ ID NO. 29) |
| ldhACF-F | 30 | TCATCAGCAGCGTCAACGGC (SEQ ID NO. 30) |
| ldhACF-R | 31 | CGCTGGTCACGGGCTTACCG (SEQ ID NO. 31) |
| ΔadhE-F | 32 | CGAGCAGATGATTTACTAAAAAAGTTTAACATTATCAGGAGAGCAT TATGAATTAACCCTCACTAAAGGGCG (SEQ ID NO. 32) |
| ΔadhE-R | 33 | CCGTTTATGTTGCCAGACAGCGCTACTGATTAAGCGGATTTTTTCGC TTTTAATACGACTCACTATAGGGCTC (SEQ ID NO. 33) |
| adhECF-F | 34 | CCGCACTGACTATACTCTCG (SEQ ID NO. 34) |
| adhECF-R | 35 | TGATCGGCATTGCCCAGAAG (SEQ ID NO. 35) |
| ΔatoDA-F | 36 | CTATTGCCTGACTGTACCCACAACGGTGTATGCAAGAGGGATAAAA AATGAATTAACCCTCACTAAAGGGCG (SEQ ID NO. 36) |
| ΔatoDA-R | 37 | ACGCGTCATAAAAACGCGATATGCGACCAATCATAAATCACCCCGTT GCGTTTAATACGACTCACTATAGGGCTC (SEQ ID NO. 37) |
| atoDACF-F | 38 | TGGCGAGGTAAAAACAGCCCC (SEQ ID NO. 38) |
| atoDACF-R | 39 | AAGCGCGATCACGAATGTTAGC (SEQ ID NO. 39) |
| Δdld-F | 40 | CGCTATTCTAGTTTGTGATATTTTTTCGCCACCACAAGGAGTGGAAA ATGAATTAACCCTCACTAAAGGGCG (SEQ ID NO. 40) |
| Δdld-R | 41 | GGATGGCGATACTCTGCCATCCGTAATTTTTACTCCACTTCCTGCCA GTTTAATACGACTCACTATAGGGCTC (SEQ ID NO. 41) |
| dldCF-F | 42 | CAGACTCACCGCGATTCCTACTG (SEQ ID NO. 42) |
| dldCF-R | 43 | CGGTAAAGTGATGCCTGTGCC (SEQ ID NO. 43) |
| Δpps-F | 44 | AGAAATGTGTTTCTCAAACCGTTCATTTATCACAAAAGGATTGTTCG ATGAATTAACCCTCACTAAAGGGCG (SEQ ID NO. 44) |
| Δpps-R | 45 | CGGCGACTAAACGCCGCCGGGGATTTATTTTATTTCTTCAGTTCAGC CAGTTAATACGACTCACTATAGGGCTC (SEQ ID NO. 45) |
| ppsCF-F | 46 | GCAGATTTGCGCAACGCTGG (SEQ ID NO. 46) |
| ppsCF-R | 47 | CTGCCGTATGGATGAGGCTG (SEQ ID NO. 47) |
| Strain | | |
| IS1 | | *E. coli* MG1655 ΔackA-pta |
| IS2 | | *E. coli* MG1655 ΔpoxB |
| IS3 | | *E. coli* MG1655 ΔldhA |
| IS4 | | *E. coli* MG1655 Δdld |
| IS5 | | *E. coli* MG1655 ΔadhE |

TABLE 4-continued

| Name | SEQ ID NO. | Sequence |
|---|---|---|
| IS6 | | E. coli MG1655 Δpps |
| IS7 | | E. coli MG1655 ΔatoDA |
| IS8 | | E. coli MG1655 ΔackA-pta, poxB (IS1 + IS2) |
| IS9 | | E. coli MG1655 ΔackA-pta, poxB, ldhA (IS8 + IS3) |
| IS10 | | E. coli MG1655 ΔackA-pta, poxB, ldhA, dld (IS9 + IS4) |
| IS11 | | E. coli MG1655 ΔackA-pta, poxB, ldhA, dld, adhE (IS10 + IS5) |
| IS12 | | E. coli MG1655 ΔackA-pta, poxB, ldhA, dld, adhE, pps (IS11 + IS6) |
| Aceco | | E. coli MG1655 ΔackA-pta, poxB, ldhA, dld, adhE, pps, atoDA (IS12 + IS7) |

From the wild type MG1655 strain, ackA-pta (SEQ ID NO: 48) and poxB (SEQ ID NO: 49) related to the generation of acetate, adhE (SEQ ID NO: 50) related to the generation of alcohol, ldhA (SEQ ID NO: 51) and dld (SEQ ID NO: 52) related to the generation of lactate, atoDA (SEQ ID NO: 53) related to the generation of acetoacetate, and pps (SEQ ID NO: 54) related to the generation of phosphoenolpyruvate were removed. With regard to preparation of the gene-deleted strain, each gene was deleted from a strain by homologous recombination using λ-Red recombinase. Then, in a case in which a further gene-deleted strain is prepared on the basis of the above-prepared gene-deleted strain, the same promoter, terminator, FRT site, etc. are already present in the strain and thus the above recombination method could not be applied. Instead, a method of combining respective gene deletions through P1 transduction was used. Finally, a strain with deletion of 9 genes related to the generation of fermentation by-product was prepared and named MG1655 AceCo.

PCR primers used for preparation of AceCo strain and a process of preparing the final AceCo are shown in Table 4 and FIG. 11. For example, a process of preparing IS1 strain will be described below. A gene group including a promoter, a marker gene, FRT site and a terminator (SEQ ID NO: 55) was amplified through PCR using ΔackA-pta-F and ΔackA-pta-R, which are primers containing peripheral 50 bp of ackA-pta gene (SEQ ID NO: 48) of E. coli, respectively, and the amplified DNA fragments were introduced into the E. coli to induce homologous recombination through λ-Red recombinase, thereby preparing IS1 strain. Screening of the gene-deleted strains was performed in a solid antibiotic medium corresponding to an antibiotic-resistant gene, which was primarily introduced. Further, with regard to the final strain with gene deletion, gene deletion was identified through PCR using ackA-ptaCF-F and ackA-ptaCF-R primers.

Referring to Table 4 and FIG. 11, strains with deletion of one gene or operon such as IS1 to IS7 were prepared by homologous recombination, separately. Then, IS1 and IS2 were combined through P1 transduction to prepare IS8 strain. To the above-prepared IS8 strain, IS3 to IS6 were integrated in sequential order through P1 transduction to prepare IS9 to IS12 strains. Lastly, the IS7 strain was integrated into the finally prepared IS12 strain, thereby preparing AceCo strain.

(2) Identification of Improved Isoprene Productivity and Prevention of Excessive Fermentation by-Product Using Strain Having Improved Carbon Source Use Efficiency The present example describes that isoprene productivity is improved and generation of fermentation by-product is prevented by introducing pTSNK-sPtispS-MVA plasmid in Example 1-(4) into the MG1655 AceCo strain prepared in Example 3-(1), as well as identified results thereof.

As a control group, MG1655 and the strain with deletion of ackA-pta gene, which is an acetic acid biosynthetic pathway gene, from the wild type E. coli MG1655, were used. The strain with deletion of ackA-pta gene from E. coli MG1655 was prepared by homologous recombination using λ-Red recombinase mentioned in Example 3-(1). Primers used in the above preparation are shown in Table 4.

The culture medium, culture conditions, and isoprene quantitation were the same as those described in the method according to Example 1-(2), except that IPTG was not added. The fermentation by-product was analyzed using a liquid chromatograph (HPLC, LC-20A) manufactured by Shimadzu Corp. A column for separation of a material used herein is an ion-exchange column (AminexR, HPX-87H, 7.8×300 mm) manufactured by BIO-RAD Co., wherein a mobile phase was 5 mM sulfuric acid and was transferred at a rate of 0.6 ml per minute. A temperature of the oven was maintained at 40° C. The residual glycerol in the medium was analyzed by the RID detector. Further, a column for separation of a material used herein was a hydrophobic column (100-5NH2, 250×4.6 mm) manufactured by Chromacyl Co. wherein a mobile phase was 75% acetonitrile and transferred at a rate of 1.5 ml per minute. A standard material for quantitative analysis was a product manufactured by Sigma Co.

Figure 12:
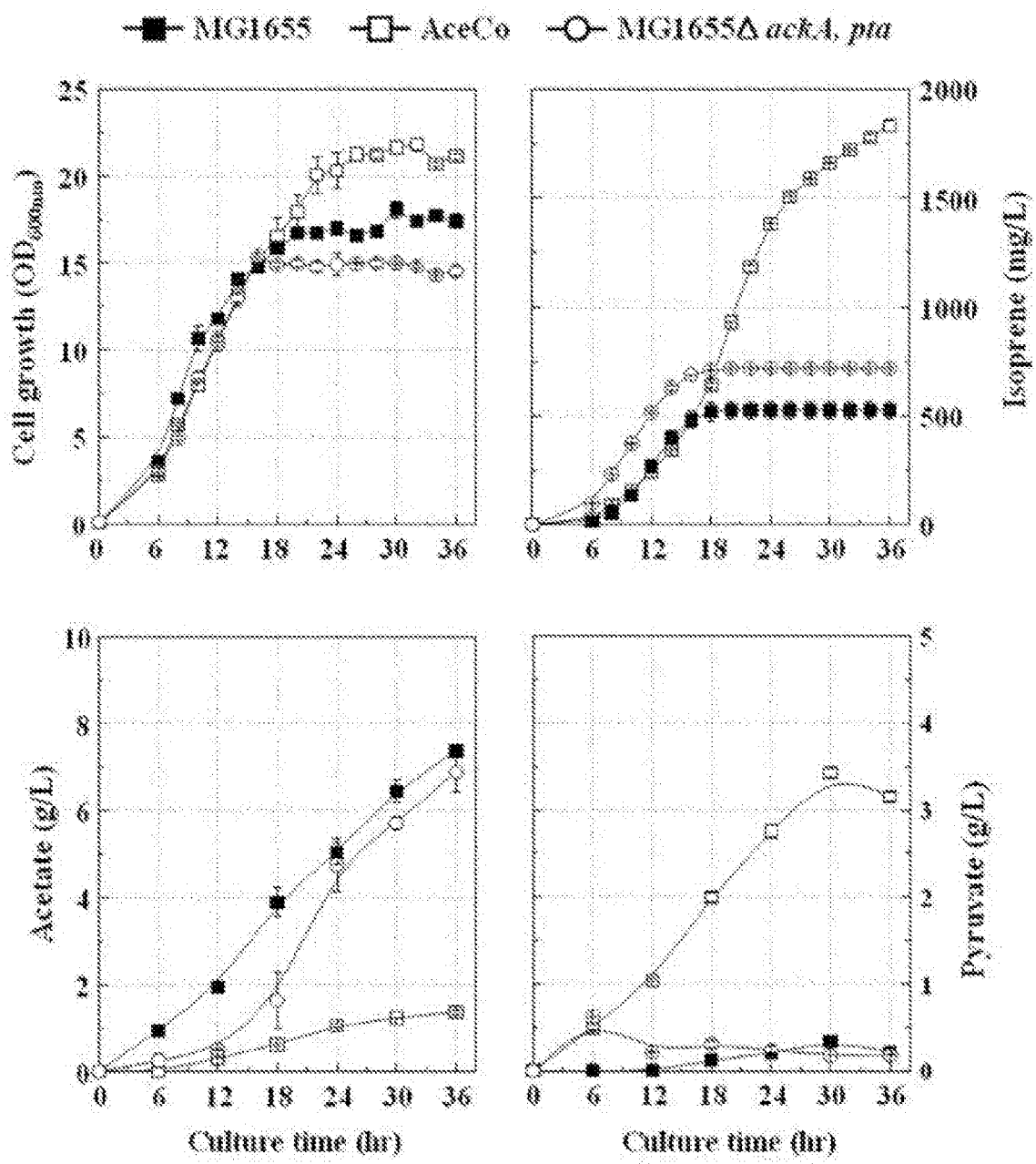
FIG. 12 illustrates results of comparing cell growth, isoprene productivity and organic acid productivity between AceCo strain having improved carbon source use efficiency, wild type strain as a control group, and ackA-pta gene-deleted strain as an acetic acid biosynthetic pathway.

Culture results are shown in FIG. 12. Referring to FIG. 12, in terms of the isoprene production amount, the AceCo strain exhibited an isoprene production amount about 3.5 times and 2.6 times higher than the wild type MG1655 and ackA-pta deleted strains as control groups, respectively. On the other hand, an acetic acid production amount as the fermentation by-product was 1.3 g/L, which is 5.6 times and 5.0 times smaller than those generated by the wild type MG1655 and ackA-pta deleted strains as control groups, respectively. As a measurement criterion for intercellular concentration of acetyl-CoA, a concentration of a precursor, that is, pyruvate in AceCo strain was determined as 3.1 g/L, which is far superior compared to the control groups, that is, the wild type MG1655 and the ackA-pta deleted strains.

Therefore, it was demonstrated from the study results that isoprene productivity may be remarkably improved if undesirable consumption of acetyl-CoA as the precursor of MVA pathway is prevented by blocking a fermentation by-product biosynthetic pathway, while improving carbon source use efficiency. Further, it was found that, when only ackA and pta genes related to acetic acid biosynthesis were deleted, there is no effect of suppressing the production of acetic acid. Furthermore, there is no advantageous effect of helping to improve isoprene productivity.

4. Improvement of Isoprene Productivity by Efficient Conversion of Isoprene Precursor to Isoprene (1) Improvement of Isoprene Productivity by Further Introducing Idi Gene Derived from Various Microorganisms The present example describes a new plasmid prepared by further introducing idi gene derived from various microorganisms into the plasmid prepared in Example 1, as well as culture results to identify improvement of isoprene productivity using the same.

*Escherichia* genus (SEQ ID NO: 7), *Haematococcus* genus (SEQ ID NO: 10), *Synechocystis* genus (SEQ ID NO: 8), *Streptococcus* genus (SEQ ID NO: 9) idi genes were inserted into XbaI restriction enzyme site of pTSN-sPtispS plasmid prepared in Example 1-(1). For example, the preparation of pTSN-sPtispS-Ecidi plasmid will be concretely described below. The gene from genome of *E. coli* was amplified using primers Ecidi-F and Ecidi-R, and the amplified gene was introduced into an XbaI site of pTSN-sPtispS to finally complete the preparation. As a result of the preparation in the same manner using the above four types of idi genes, pTSN-sPtispS-Ecidi, pTSN-sPtispS-HPidi, pTSN-sPtispS-Syidi and pTSN-sPtispS-Snidi plasmids were prepared. PCR primers used for additional introduction of idi genes are shown in Table 5.

TABLE 5

| SEQ ID NO. | Primer | Sequence |
|---|---|---|
| 56 | Ecidi-F | 5'-C<u>GAATTC</u>AGGAGGAGAAATTATGCAAACG GAACACGTC-3'<br>(SEQ ID NO. 56) |
| 57 | Ecidi-R | 5'-C<u>CTGCAG</u>GTCGAAATTCTTATTTAAGCTG GGTAAA-3'<br>(SEQ ID NO. 57) |
| 58 | Hpidi-F | 5'-G<u>GAATTC</u>AGGAGGTAATAAAATATGCTTC GTTCGTTGCTCAG-3'<br>(SEQ ID NO. 58) |
| 59 | Hpidi-R | 5'-C<u>AAGCTT</u>GATCACTAGTTACGCTTCGTTG ATGTG-3'<br>(SEQ ID NO. 59) |
| 60 | Syidi-F | 5'-G<u>GAATTC</u>AGGAGGATTCACTGATGGATAG CACCCCCAC-3'<br>(SEQ ID NO. 60) |
| 61 | Syidi-R | 5'-C<u>CTGCAG</u>GTCGACTCTAGTTAAGGTTTAG TTAACC-3'<br>(SEQ ID NO. 61) |
| 62 | Snidi-F | 5'-<u>TCTAGA</u>GGAGGATAGGACATGACGACAAA TCGTAAG-3'<br>(SEQ ID NO. 62) |

TABLE 5-continued

| SEQ ID NO. | Primer | Sequence |
|---|---|---|
| 63 | Snidi-R | 5'-<u>GTCGAC</u>TCTAGTTACGCCTTTTTCATCTG ATC-3'<br>(SEQ ID NO. 63) |

These plasmids were introduced along with pS-NA into *E. coli* MG1655 AceCo ΔrecA strain to form a transformant, and were investigated whether isoprene productivity was improved or not.

The culture medium, culture conditions and isoprene quantitation were the same as those described in the method according to Example 1-(2), and 0.5 mM IPTG was added to the culture medium.

Figure 13:
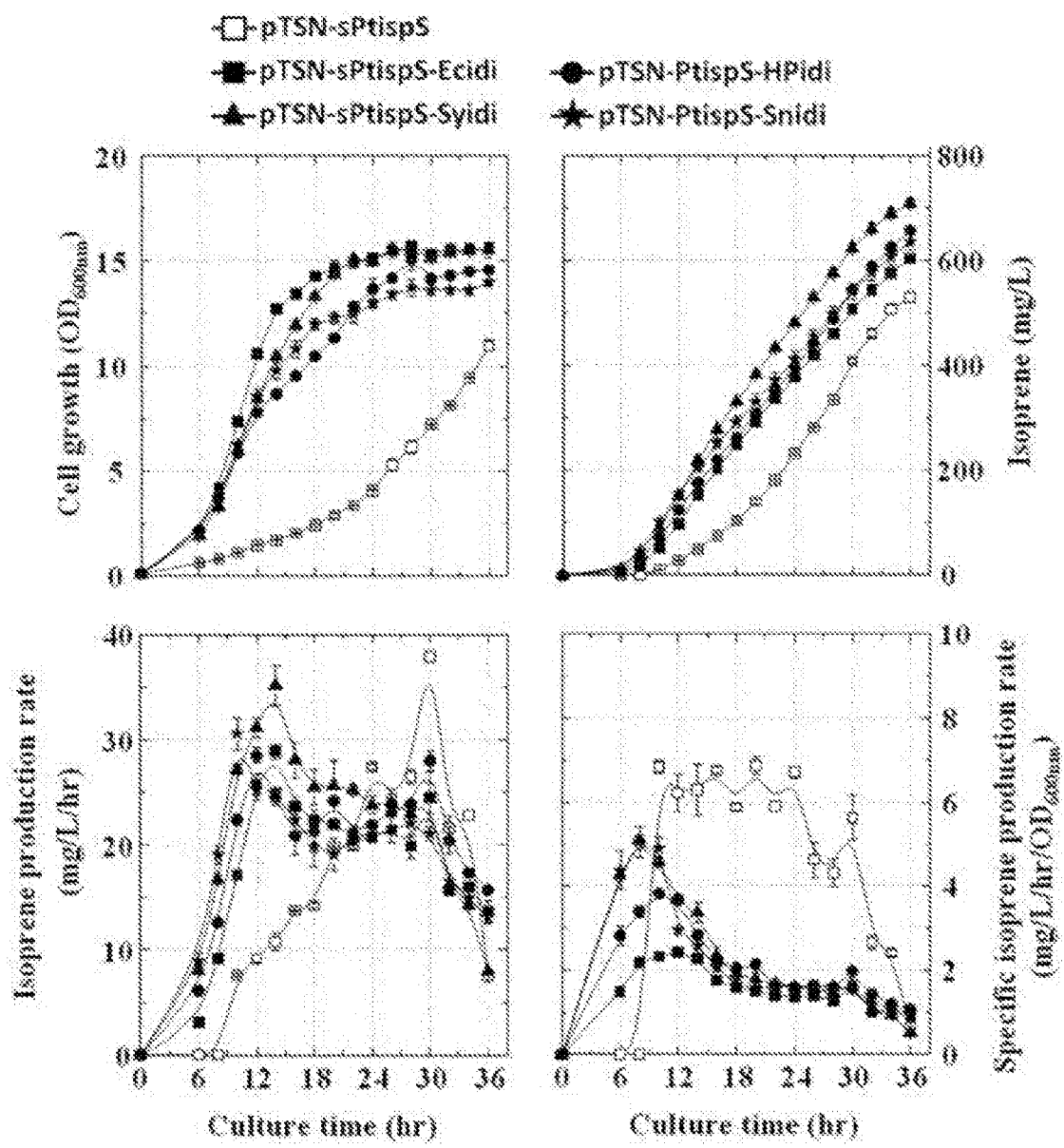
FIG. 13 illustrates a result of identifying improved isoprene productivity by introducing additional idi gene into isoprene producing plasmid.

Culture results are shown in FIG. 13. Referring to FIG. 13, the strain with additional introduction of *Synechocystis* genus idi gene showed the highest isoprene production amount. Further, others with additional introduction of the remaining idi genes also exhibited a higher isoprene production amount than the control group.

From the results, it was demonstrated that additional introduction of idi gene was helpful for improving the isoprene productivity, and *Synechocystis* genus idi is the most efficient among the genes described above.

(2) Identification of Improved Isoprene Productivity According to Preparation and Application of Fusion Protein Based on the results in Example 4-(1), the present example describes preparation of a fusion protein by combining *Synechocystis* genus idi, which exhibited the improved isoprene productivity, and *E. coli*-specific *Escherichia* genus idi with isoprene synthase in a fusion form, as well as results of improving isoprene productivity using the same.

After removing a stop codon of isoprene synthase (amplified through PCR using primers FispS-F and FispS-R) and thus cloning the same at NcoI and XbaI sites of pTrc99SN vector, it was designed to insert idi gene having a serine-glycine linker (amplified through PCR using primers REcidi-F and REcidi-R or RSyidi-F and RSyidi-R) at the back of the isoprene synthase using an XbaI site, so that two genes are expressed as a single protein. The prepared plasmids were named pTSN-sPtispS-L-Sydid and pTSN-sPtispS-L-Ecidi, respectively. Further, after cloning idi (amplified through PCR using primers FEcidi-F and FEcidi-R or FSyidi-F and FSyidi-R) at NcoI and XbaI sites of pTrc99SN vector, the isoprene synthase having a serine-glycine linker (amplified through PCR using primers RispS-F and RispS-R) was inserted at the back of idi gene using the XbaI site, so as to prepare pTSN-Syidi-L-sPtispS and pTSN-Ecidi-L-sPtispS, respectively. PCR primers used for the preparation of genes encoding fusion proteins are shown in Table 6.

TABLE 6

| SEQ ID NO. | Primer | Sequence |
|---|---|---|
| 64 | FispS-F | 5'-<u>GAATTC</u>GAGCTCAGGAGGTAATAAATAT GGCTTGCTCTGTATCC-3'<br>(SEQ ID NO. 64) |

TABLE 6-continued

| SEQ ID NO. | Primer | Sequence |
|---|---|---|
| 65 | FispS-R | 5'-GGATCCGCCGCCACCCGAGCCACCGCCACCGCGTTCGAACGGCAGAATTG-3' (SEQ ID NO. 65) |
| 66 | RispS-F | 5'-GGATCCATGGCTTGCTCTGTATCCACTGAG-3' (SEQ ID NO. 66) |
| 67 | RispS-R | 5'-CTGCAGGTCGACTTAGCGTTCGAACGGCAG-3' (SEQ ID NO. 67) |
| 68 | FEcidi-F | 5'-GAATTCGAGCTCAGGAGGTAATAAATATGCAAACGGAACACGTC-3' (SEQ ID NO. 68) |
| 69 | FEcidi-R | 5'-GGATCCGCCGCCACCCGAGCCACCGCCACCTTTAAGCTGGGTAAATGC-3' (SEQ ID NO. 69) |
| 70 | REcidi-F | 5'-GGATCCATGCAAACGGAACACGTCATTTTATTG-3' (SEQ ID NO. 70) |
| 71 | REcidi-R | 5'-CTGCAGGTCGACTTATTTAAGCTGGGTAAATG-3' (SEQ ID NO. 71) |
| 72 | FSyidi-F | 5'-GAATTCGAGCTCAGGAGGTAATAAATATGGATAGCACCCCCCACCG-3' (SEQ ID NO. 72) |
| 73 | FSyidi-R | 5'-GGATCCGCCGCCACCCGAGCCACCGCCACCAGGTTTAGTTAACCTTTGTC-3' (SEQ ID NO. 73) |
| 74 | RSyidi-F | 5'-GGATCCATGGATAGCACCCCCCACCGTAAG-3' (SEQ ID NO. 74) |
| 75 | RSyidi-R | 5'-CTGCAGGTCGACTTAAGGTTTAGTTAACCTTTG-3' (SEQ ID NO. 75) |

In order to identify whether isoprene productivity was improved or not, the plasmids which include genes encoding four types of fusion proteins were introduced into pS-NA and E. coli DH5α, simultaneously, and cultured.

The culture medium, culture conditions and isoprene quantitation were the same as those described in the method according to Example 1-(2), except that IPTG was not added.

Figure 14:
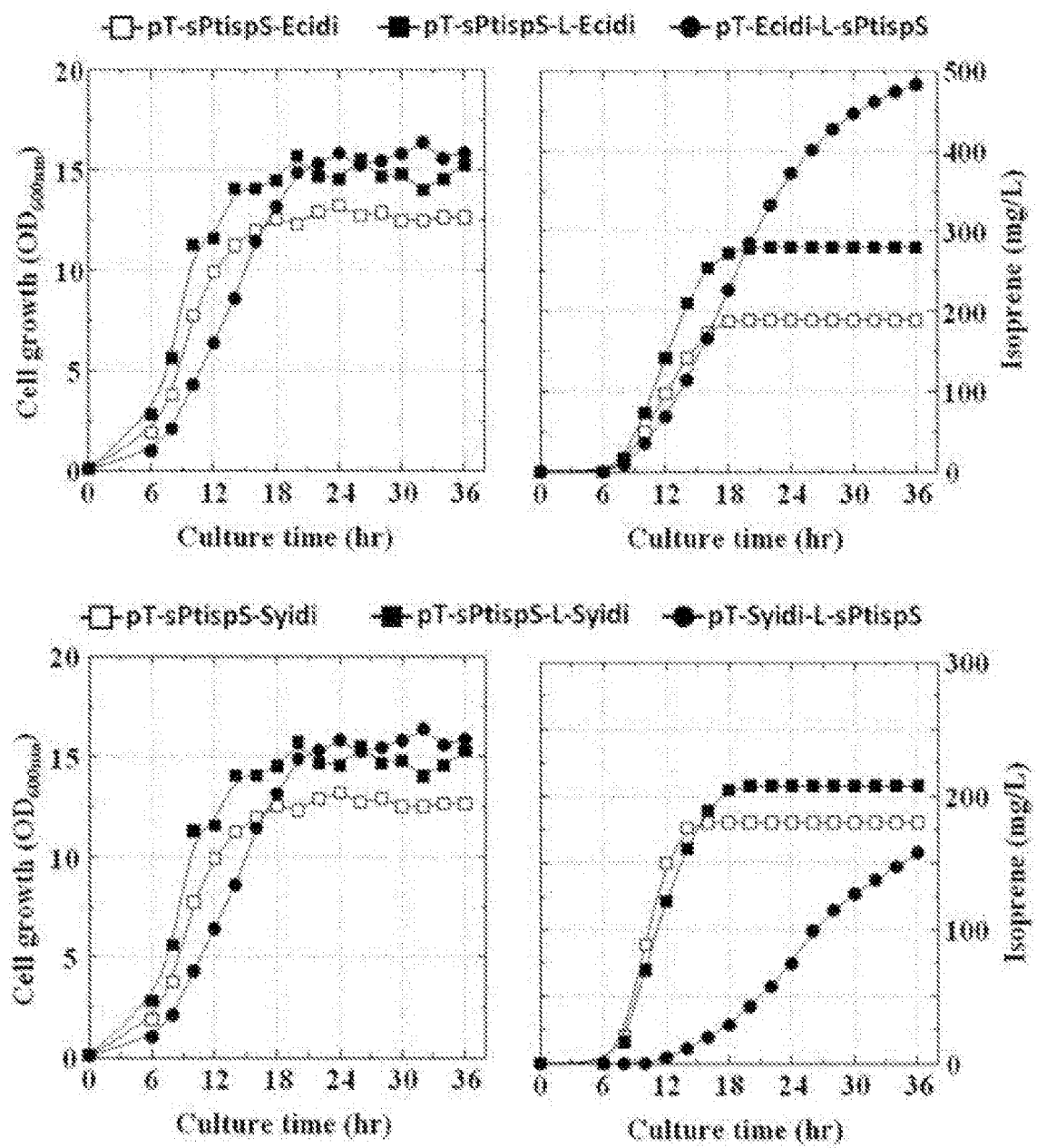
FIG. 14 illustrates a result of improving isoprene productivity using a fusion protein of IspS and IDI.

Culture results are shown in FIG. 14. Referring to FIG. 14, as a result of the culture, the fusion protein of IspS and Escherichia genus IDI exhibited a higher isoprene production amount than Synechocystis genus IDI fusion protein. In particular, the fusion form in which Escherichia genus IDI is fused at the front of IspS exhibited the highest isoprene productivity and an isoprene production amount of about 2.4 times higher than the control group.

Based on the above results, it could be confirmed that the fusion protein of IspS and IDI might more efficiently convert IPP to isoprene.

5. Identification of Isoprene Productivity According to Culture Condition (1) Identification of Isoprene Productivity According to Types of Inducing Materials The present example describes results of identification of isoprene productivity according to types of inducing agents to increase a protein expression level.

Lactose is degraded into glucose and galactose by β-galactosidase. Further, glucose and galactose may be synthesized into lactose by a reverse reaction of β-galactosidase. In this case, allolactose may be generated at a predetermined probability and this allolactose acts as an expression-inducing agent. Based on this fact, it is expected that an expression level of β-galactosidase is increased in proportion to increase in an amount of cells, which in turn proportionally increases an amount of allolactose. In order to properly control the expression of isoprene biosynthesis-related genes, isoprene productivity was investigated by adding lactose.

After introducing pTSNK-sPtispS-MVA into MG1655ΔrecA strain to form an E. coli transformant, 5 ml TB medium including 50 μm/ml of kanamycin (24 g yeast extract, 12 g tryptone, 9.4 g $K_2HPO_4$, 2.2 g $KH_2PO_4$ per liter) was inoculated with the transformant having isoprene productivity and then subjected to seed culture under conditions of 37° C. and 250 rpm. Thereafter, 50 ml TB medium including 20 g/L of glycerol and 50 μm/ml of kanamycin was inoculated with the seed-cultured product and then subjected to main culture. In order to increase a protein expression level, as the expression-inducing agents, IPTG at a final concentration of 0.03 mM and lactose at final concentrations of 5 g/l, 10 g/l and 20 g/l, respectively, were added. In a condition of adding 20 g/l of lactose, glycerol was not added. The main culture was conducted in 250 ml grooved conical flask under conditions of 30° C. and 150 rpm for 36 hours. The isoprene quantitation was performed according to the same procedures as described in the method according to Example 1-(2), except that IPTG was not added.

Figure 15:
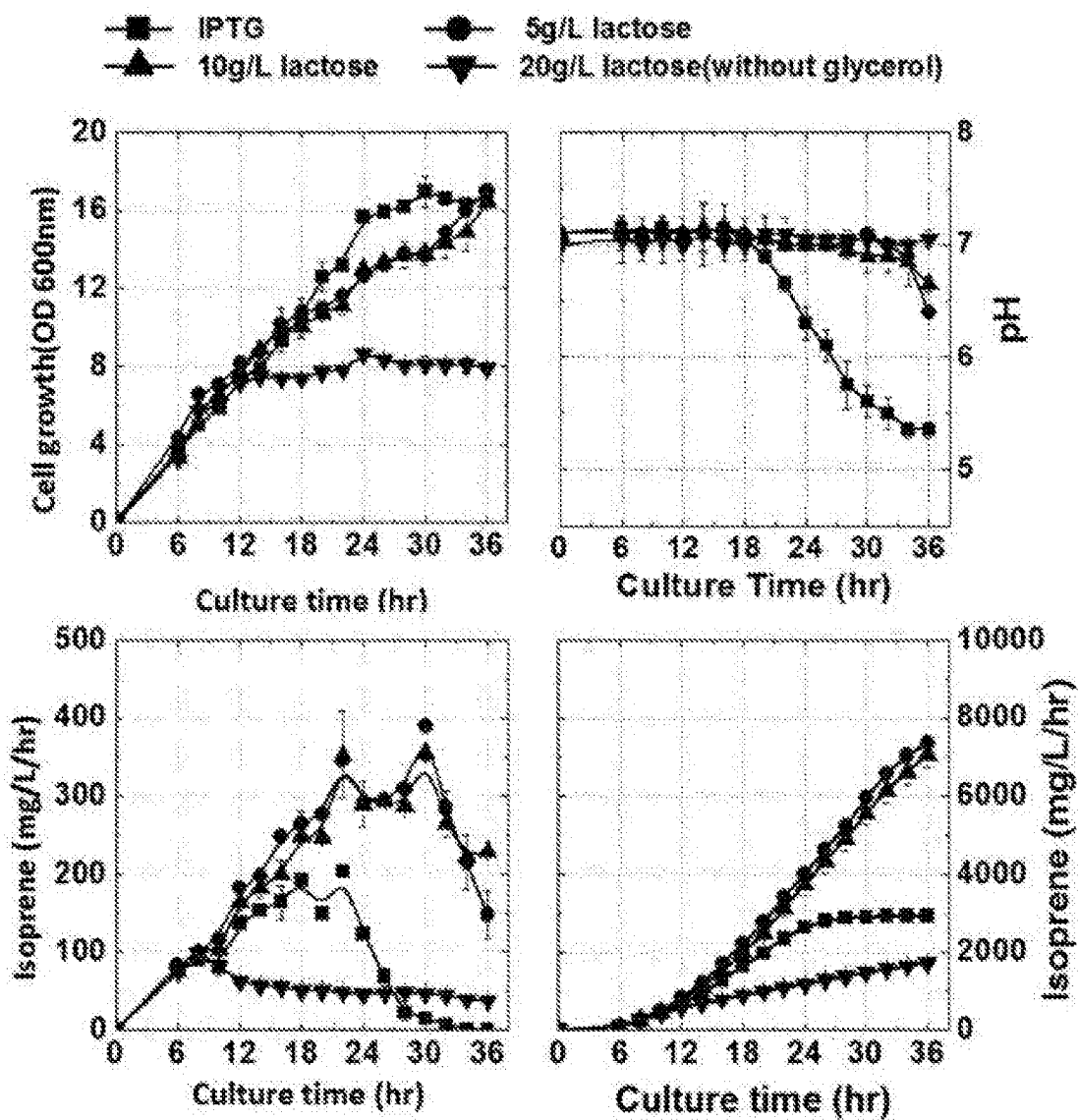
FIG. 15 illustrates a result of comparing isoprene productivity using IPTG and lactose as an expression-inducing agent for expressing a biosynthetic pathway of isoprene.

Culture results are shown in FIG. 15. Referring to FIG. 15, it was found that, when adding lactose along with glycerol, an isoprene production amount was about 2.3 times higher than the condition of addition of IPTG. Based on this result, it could be confirmed that addition of lactose as an expression-inducing agent was helpful for improving the isoprene productivity.

(2) Identification of Isoprene Productivity According to Addition of Auxiliary Factor $Mg^{2+}$ The present example describes results of identification of isoprene productivity when further adding an auxiliary factor of isoprene synthase, $Mg^{2+}$.

It was reported that the isoprene synthase had optimum activity in the presence of 20 mM $Mg^{2+}$ as an auxiliary factor. Therefore, isoprene productivity was investigated by adding excessive amount of $Mg^{2+}$.

After introducing pTSNK-sPtispS-MVA into MG1655ΔrecA strain to form an E. coli transformant, 5 ml 2YT medium including 50 μm/ml of kanamycin (10 g yeast extract, 16 g tryptone, 5 g NaCl per liter) was inoculated with the transformant having isoprene productivity and then subjected to seed culture under conditions of 37° C. and 250 rpm. Thereafter, 50 ml MR medium including 20 g/L of glycerol and 50 μm/ml of kanamycin ($KH_2PO_4$ 40.6 g, $MgSO_4·7H_2O$ 0.492 g, $Na_2HPO_4O_7·2H_2O$ 2.56 g, NaCl 20.1 g, $NH_4Cl$ 0.2 g per liter) was inoculated with the seed cultured product and subjected to main culture. In order to increase a protein expression level, an expression-inducing agent, that is, lactose at a final concentration of 5 g/l was added. Further, 30 mM $Mg^{2+}$ as an auxiliary factor was added. The main culture was conducted in 250 ml grooved conical flask under conditions of 30° C. and 150 rpm for 60 hours. The isoprene quantitation was performed according to the same procedures as described in the method according to Example 1-(2), except that IPTG was not added.

Figure 16:
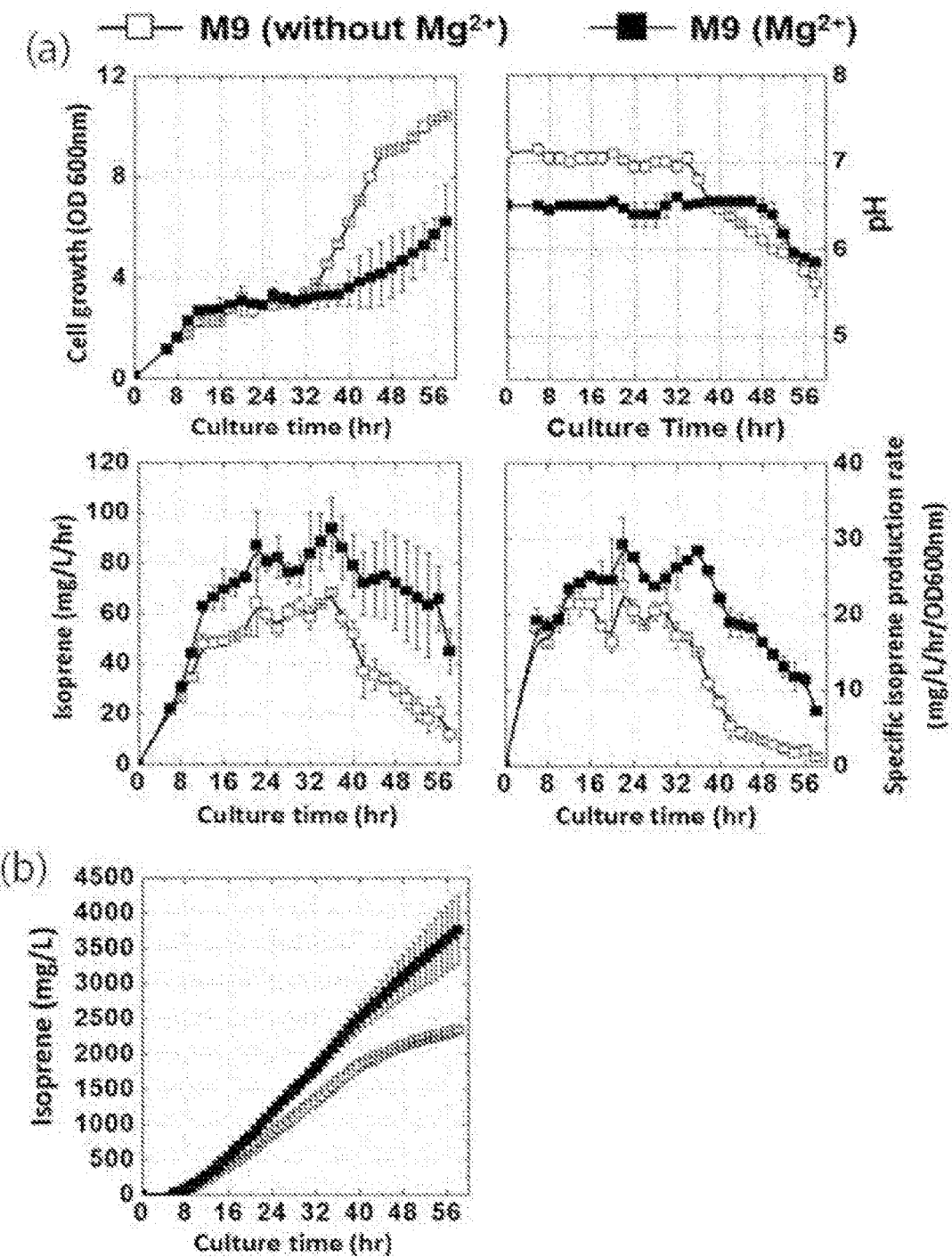
FIG. 16 illustrates a result of comparing isoprene productivity according to whether or not to add $Mg^{2+}$ to a culture medium for isoprene production.

Culture results are shown in FIG. 16. Referring to FIG. 16, it was found that, when 30 mM $Mg^{+2}$ was further added to MR medium containing a predetermined amount of $Mg^{2+}$, isoprene production was about 1.65 times higher than the same medium without further addition of $Mg^{2+}$. Based on this result, it could be confirmed that addition of $Mg^{2+}$ as an auxiliary factor was helpful for improving the isoprene productivity.

The invention claimed is:

1. An *E. coli* transformant comprising:
foreign genes which are introduced into the *E. coli* to make the *E. coli* capable of producing the isoprene, the foreign genes comprising:
   a first foreign gene encoding isoprene synthase;
   a second foreign gene encoding an enzyme with function of acetyacetyl-CoA synthase;
   a third foreign gene encoding an enzyme with function of HMG-CoA reductase, wherein the second foreign gene and the third foreign gene are optionally a single gene encoding an enzyme with functions of both the acetyacetyl-CoA synthase and the HMG-CoA reductase;
   a fourth foreign gene encoding HMG-CoA synthase;
   a firth foreign gene encoding mevalonate kinase;
   a sixth foreign gene encoding mevalonate diphosphate carboxylase;
   a seventh foreign gene encoding phosphomevalonate kinase; and
   an eighth foreign gene encoding isoprenyl pyrophosphate isomerase; and
wherein, in the *E. coli* transformant, a gene encoding a recA protein is attenuated or deleted in the *E. coli* to reduce or remove expression of the gene encoding the recA protein; and
the *E. coli* transformant produces increased amounts of the isoprene, compared to wild type *E. coli*.

2. The *E. coli* according to claim 1, wherein the *E. coli* is DH5a, MG1655, BL21(DE), S17-1, XL1-Blue, BW25113 or a combination thereof.

3. The *E. coli* according to claim 1, wherein the *E. coli* is MG1655.

4. The *E. coli* according to claim 1, wherein the gene encoding the recA protein has the nucleotide sequence of SEQ ID NO: 76.

5. The *E. coli* according to claim 1, wherein the foreign gene comprises:
   the first foreign gene which is the nucleotide sequence of SEQ ID NO: 1 encoding isoprene synthase derived from *Populus trichocarpa*;
   the second foreign gene and the third foreign gene are a single gene which is the nucleotide sequence of SEQ ID NO: 2 encoding the enzyme with functions of acetyacetyl-CoA synthase derived from *Enterococcus faecalis* and HMG-CoA reductase, simultaneously;
   the fourth foreign gene which is the nucleotide sequence of SEQ ID NO: 3 encoding HMG-CoA synthase derived from *Enterococcus faecalis*;
   the fifth foreign gene which is the nucleotide sequence of SEQ ID NO: 4 encoding mevalonate kinase derived from *Streptococcus pneumoniae*;

the sixth foreign gene which is the nucleotide sequence of SEQ ID NO: 5 encoding mevalonate diphosphate carboxylase derived from *Streptococcus pneumoniae;* the seventh foreign gene which is the nucleotide sequence of SEQ ID NO: 6 encoding phosphomevalonate kinase derived from *Streptococcus pneumoniae;* and the eighth foreign gene which is the nucleotide sequence of SEQ ID NO: 7 encoding isoprenyl pyrophosphate isomerase derived from *Escherichia coli* MG 1655.

6. The *E. coli* according to claim 1, wherein the *E. coli* includes:

the first foreign gene and the eight foreign gene are a single gene which is the nucleotide sequence of SEQ ID NO: 11 encoding a fusion protein of isoprene synthase derived from *Populus trichocarpa* and isoprenyl pyrophosphate isomerase derived from *E. coli* MG1655;

the first foreign gene and the eight foreign gene are a single gene which is the nucleotide sequence of SEQ ID NO: 12 encoding a fusion protein of isoprenyl pyrophosphate isomerase derived from *E. coli* MG1655 and isoprene synthase derived from *Populus trichocarpa;* the first foreign gene and the eight foreign gene are a single gene which is the nucleotide sequence of SEQ ID NO: 13 encoding a fusion protein of isoprene synthase derived from *Populus trichocarpa* and *Synechocystis* isoprenyl pyrophosphate isomerase; or the first foreign gene and the eight foreign gene are a single gene which is the nucleotide sequence of SEQ ID NO: 14 encoding a fusion protein of *Synechocystis* isoprenyl pyrophosphate isomerase and isoprene synthase derived from *Populus trichocarpa.*

7. The *E. coli* according to claim 1, wherein the *E. coli* is characterized in that at least one gene selected from the group consisting of dld, atoD, atoA and pps is attenuated or deleted.

8. The *E. coli* according to claim 1, wherein the *E. coli* is characterized in that a gene encoding NudB protein is attenuated or deleted.

9. The *E. coli* according to claim 1, wherein the gene has a nucleotide sequence of SEQ ID NO: 77.

10. The *E. coli* according to claim 1, wherein the *E. coli* is characterized in that flagella are inactivated or removed.

11. The *E. coli* according to claim 1, wherein the *E. coli* is characterized in that at least one gene selected from the group consisting of fliF, fliG, fliH, fliI, fliJ and fliK is deleted or inactivated.

12. The *E. coli* according to claim 1, wherein the *E. coli* expresses isoprene synthase.

13. An *E. coli* transformant comprising a deletion of the gene encoding a recA protein and comprising the nucleotide sequence of SEQ ID NO: 1 encoding isoprene synthase, the nucleotide sequence of SEQ ID NO: 2 encoding an enzyme with functions of acetoacetyl-CoA synthase and HMG-CoA reductase, the nucleotide sequence of SEQ ID NO: 3 encoding HMG-CoA synthase, the nucleotide sequence of SEQ ID NO: 4 encoding mevalonate kinase, the nucleotide sequence of SEQ ID NO: 5 encoding mevalonate diphosphate carboxylase, the nucleotide sequence of SEQ ID NO: 6 encoding phosphomevalonate kinase, and the nucleotide sequence of SEQ ID NO: 7 encoding isoprenyl pyrophosphate isomerase, where the *E. coli* transformant produces increased amounts of isoprene compared to wild type *E. coli.*

14. A method for producing isoprene, comprising:
culturing the *E. coli* transformant of claim 1 in a medium containing a carbon source,
wherein the cultured *E. coli* transformant produces the isoprene.

15. The method according to claim 14, wherein the *E. coli* is DH5a, MG1655, BL21(DE), S17-1, XL1-Blue, BW25113 or a combination thereof.

16. The method according to claim 14, wherein the *E. coli* is MG1655.

17. The method according to claim 14, wherein the gene encoding the recA protein has a nucleotide sequence of SEQ ID NO: 76.

18. The method according to claim 14, wherein the *E. coli* expresses the isoprene synthase and an enzyme of *Enterococcus* genus or *Streptococcus* genus mevalonate pathway.

19. The method according to claim 14, wherein the *E. coli* has the gene encoding the isoprene synthase derived from *Populus trichocarpa* of SEQ ID NO: 1 intrinsically or by introduction therein.

20. The method according to claim 6, wherein the foreign gene is introduced into a plasmid having a translation initiation rate value of 3,000 au or more in a ribosomal binding site sequence corresponding thereto.

21. The method according to claim 14, wherein the *E. coli* includes:

a gene of SEQ ID NO: 2 encoding an enzyme with functions of acetyacetyl-CoA synthase derived from *Enterococcus faecalis* and HMG-CoA reductase, simultaneously;

a gene of SEQ ID NO: 3 encoding HMG-CoA synthase derived from *Enterococcus faecalis;* a gene of SEQ ID NO: 4 encoding mevalonate kinase derived from *Streptococcus pneumoniae;* a gene SEQ ID NO: 5 encoding mevalonate diphosphate carboxylase derived from *Streptococcus pneumoniae;* a gene of SEQ ID NO: 6 encoding phosphomevalonate kinase derived from *Streptococcus pneumoniae;* and a gene SEQ ID NO: 7 encoding isoprenyl pyrophosphate isomerase derived from *Escherichia coli* MG 1655, which are contained intrinsically or by introduction therein.

22. The method according to claim 21, wherein the *E. coli* further includes a gene selected from the group consisting of:

a gene of SEQ ID NO: 8 encoding isoprenyl pyrophosphate isomerase derived from *Synechocystis* sp. PCC6803;

a gene of SEQ ID NO: 9 encoding isoprenyl pyrophosphate isomerase derived from *Streptococcus pneumoniae;* and a gene of SEQ ID NO: 10 encoding isoprenyl pyrophosphate isomerase derived from *Haematococcus plavialis,* which is included intrinsically or by introduction therein.

23. The method according to claim 14, wherein the *E. coli* includes:

a gene of SEQ ID NO: 11 encoding a fusion protein of isoprene synthase derived from *Populus trichocarpa* and isoprenyl pyrophosphate isomerase derived from *E. coli* MG1655;

a gene of SEQ ID NO: 12 encoding a fusion protein of isoprenyl pyrophosphate isomerase derived from *E. coli* MG1655 and isoprene synthase derived from *Populus trichocarpa;* a gene of SEQ ID NO: 13 encoding a fusion protein of isoprene synthase derived from *Populus trichocarpa* and *Synechocystis* isoprenyl pyrophosphate isomerase; or a gene of SEQ ID NO: 14 encoding a fusion protein of *Synechocystis* isoprenyl pyrophosphate isomerase and isoprene synthase derived from *Populus trichocarpa*.

24. The method according to claim 14, wherein the *E. coli* is characterized in that at least one gene selected from the group consisting of dld, atoD, atoA and pps is attenuated or deleted.

25. The method according to claim 14, wherein the *E. coli* is characterized in that at least one gene selected from the group consisting of ackA-pta, poxB, adhE and ldhA is attenuated or deleted.

26. The method according to claim 14, wherein the *E. coli* is characterized in that a gene encoding NudB protein is attenuated or deleted.

27. The method according to claim 26, wherein the gene has a nucleotide sequence of SEQ ID NO: 77.

28. The method according to claim 14, wherein the *E. coli* is characterized in that flagella are inactivated or removed.

29. The method according to claim 28, wherein the *E. coli* is characterized in that at least one gene selected from the group consisting of fliF, fliG, fliH, fliI, fliJ and fliK is deleted or inactivated.

30. The method according to claim 14, wherein the medium contains lactose.

31. The method according to claim 14, wherein the medium contains $Mg^{2+}$.

* * * * *